US010786150B2

(12) United States Patent
Durr et al.

(10) Patent No.: US 10,786,150 B2
(45) Date of Patent: *Sep. 29, 2020

(54) APPARATUS AND METHOD OF DETERMINING AN EYE PRESCRIPTION

(71) Applicants: Massachusetts Institute of Technology, Cambridge, MA (US); Consejo Superior de Investigaciones Cientificas, Madrid (ES)

(72) Inventors: Nicholas James Durr, Baltimore, MD (US); Eduardo Lage Negro, Madrid (ES); Shivang R. Dave, Boston, MA (US); Carlos Dorronsoro Diaz, Madrid (ES); Susana Marcos Celestino, Madrid (ES); Daryl Lim, Boston, MA (US)

(73) Assignees: Massachusetts Institute of Technology, Cambridge, MA (US); Consejo Superior de Investigaciones Cientificas, Madrid (ES)

( * ) Notice: Subject to any disclaimer, the term of this patent is extended or adjusted under 35 U.S.C. 154(b) by 238 days.

This patent is subject to a terminal disclaimer.

(21) Appl. No.: 15/809,488

(22) Filed: Nov. 10, 2017

(65) Prior Publication Data
US 2018/0078131 A1    Mar. 22, 2018

Related U.S. Application Data

(63) Continuation of application No. 14/900,691, filed as application No. PCT/US2014/045261 on Jul. 2, 2014, now abandoned.
(Continued)

(51) Int. Cl.
*A61B 3/103* (2006.01)
*A61B 3/10* (2006.01)
(Continued)

(52) U.S. Cl.
CPC ............ *A61B 3/103* (2013.01); *A61B 3/0025* (2013.01); *A61B 3/0041* (2013.01);
(Continued)

(58) Field of Classification Search
CPC ..... A61B 3/103; A61B 5/7455; A61B 3/0091; A61B 3/0025; A61B 3/152; A61B 3/18;
(Continued)

(56) References Cited

U.S. PATENT DOCUMENTS 5,684,561 A * 11/1997 Yancey ................. A61B 3/103
351/209
6,988,801 B2   1/2006 Yoon
(Continued)

FOREIGN PATENT DOCUMENTS

JP      2003-536404       9/2003
WO    WO 01/06914 A1    2/2001
(Continued)

OTHER PUBLICATIONS

Japanese Patent Office, Official Action, Japanese Application No. 2016-524353, 5 pages, Mar. 8, 2018.
(Continued)

*Primary Examiner* — Jade R Chwasz
*Assistant Examiner* — Rahman Abdur
(74) *Attorney, Agent, or Firm* — Sunstein LLP

(57) ABSTRACT

Eye prescriptions may be determined by providing a simple, easy to use, portable device with a specially configured targeting light source that aligns the eye, mitigates accommodation, and provides accurate results. Unlike stationary, closed view autorefractors, this device typically is portable, self-usable, relatively inexpensive, enabling more widespread use across the world.

18 Claims, 41 Drawing Sheets

Related U.S. Application Data

(60) Provisional application No. 61/842,190, filed on Jul. 2, 2013, provisional application No. 61/972,058, filed on Mar. 28, 2014, provisional application No. 61/972,191, filed on Mar. 28, 2014.

(51) Int. Cl.
| | |
|---|---|
| *A61B 3/113* | (2006.01) |
| *A61F 9/008* | (2006.01) |
| *A61B 3/00* | (2006.01) |
| *A61B 5/00* | (2006.01) |
| *A61B 3/18* | (2006.01) |
| *A61B 3/14* | (2006.01) |
| *A61B 3/15* | (2006.01) |

(52) U.S. Cl.
CPC .......... *A61B 3/0091* (2013.01); *A61B 3/1015* (2013.01); *A61B 3/113* (2013.01); *A61B 5/7415* (2013.01); *A61B 5/7455* (2013.01); *A61F 9/008* (2013.01); *A61B 3/145* (2013.01); *A61B 3/152* (2013.01); *A61B 3/18* (2013.01); *A61B 2560/0425* (2013.01)

(58) Field of Classification Search
CPC ..... A61B 5/7415; A61B 3/145; A61B 3/0041; A61B 3/1015; A61B 2560/0425; G02C 7/028; G02C 7/027
USPC ......................................................... 351/205
See application file for complete search history.

(56) References Cited

U.S. PATENT DOCUMENTS

| | | | |
|---|---|---|---|
| 7,131,727 B2* | 11/2006 | Jones | A61B 3/0285 351/159.11 |
| 9,427,156 B1 | 8/2016 | Steven et al. | |
| 9,629,541 B2 | 4/2017 | Zhou | |
| 2003/0071969 A1 | 4/2003 | Levine et al. | |
| 2003/0107703 A1 | 6/2003 | Cox et al. | |
| 2003/0151721 A1 | 8/2003 | Lai et al. | |
| 2004/0174495 A1 | 9/2004 | Levine | |
| 2004/0218142 A1 | 11/2004 | Wakil et al. | |
| 2005/0001981 A1 | 1/2005 | Anderson et al. | |
| 2005/0007551 A1 | 1/2005 | Wakil et al. | |
| 2005/0174535 A1 | 8/2005 | Lai et al. | |
| 2005/0243276 A1 | 11/2005 | Van Heugten et al. | |
| 2005/0280777 A1 | 12/2005 | Dai | |
| 2008/0198331 A1 | 8/2008 | Azar et al. | |
| 2008/0284979 A1 | 11/2008 | Yee et al. | |
| 2009/0002632 A1 | 1/2009 | Vogelsang et al. | |
| 2011/0149239 A1 | 6/2011 | Neal et al. | |
| 2013/0033593 A1 | 2/2013 | Chinnock et al. | |
| 2013/0085459 A1 | 4/2013 | Voss et al. | |
| 2014/0268037 A1* | 9/2014 | Siminou | A61B 3/0083 351/205 |
| 2014/0300868 A1 | 10/2014 | Zhou | |

FOREIGN PATENT DOCUMENTS

| | | |
|---|---|---|
| WO | WO 2005/052538 | 6/2005 |
| WO | WO 2015/102703 | 7/2015 |

OTHER PUBLICATIONS

Japanese Patent Office, Official Action, Japanese Application No. 2016-524353, 7 pages, Mar. 8, 2018 (English Translation).
European Patent Office, European Search Report, Application No. EP 18 17 5052, 7 pages, Sep. 10, 2018.
AIT Industries, Grand Seiko WAM-5500, http://www.aitindustries.com/ophthalmic-instruments/autorefractors/wam5500-binocular-autorefractor.html, 2 pages, Jun. 2013.
Beverage, et al., "A Shack-Hartmann-Based Autorefractor," Journal of Refractive Surgery, vol. 22, pp. 932-937, Nov. 2006 (Abstract).
Boston University, "Partioned aperture wavefront imaging," http://biomicroscopy.bu.edu/research/partioned-aperture-wavefront-imaging 2 pages, 2014.
Cerviño, et al., "Wavefront Analyzers Induce Instrument Myopia," Journal of Refractive Surgery, vol. 22, issue 8, pp. 795-803, Oct. 2006, posted online Jul. 15, 2006 (Abstract).
Coleman, "Therapeutic treatments will be the first application, but high-definition scans and new-technology topography may eventually be incorporated into routine cases," 2013.
Durrie, "Using Wavefront Aberrometry as a Primary Diagnostic Tool," Ophthalmology Management, 4 pages, Apr. 2004.
European Patent Office, Supplementary European Search Report, Application No. EP 14819857, 6 pages, Nov. 23, 2016.
European Patent Office, Supplementary European Search Report, Application No. EP 14820078.5, 7 pages, Dec. 6, 2016.
European Patent Office, Communication pursuant to Rules 70(2) and 70a(2) EPC, Application No. EP 14820078.5, 1 page, Jan. 9, 2017.
International Searching Authority, FIPS Russia, International Search Report together with the Written Opinion of the International Searching Authority for International Application No. PCT/US2014/045305, 11 pages, Oct. 30, 2014.
International Searching Authority, FIPS Russia, International Search Report together with the Written Opinion of the International Searching Authority for International Application No. PCT/US2014/045261, 8 pages, Nov. 6, 2014.
Imagine Eyes, "Frequently asked questions (FAQ) about wavefront aberrometry," http://www.imagine-eyes.com/applications/wavefront_aberrometry/faq-2/, 4 pages, 2013.
Kendall, Nikon Retinomax 2 Autorefractor Usage Instructions, 32 pages, Jan. 17, 2003.
Maeda, "Clinical applications of wavefront aberrometry—a review," Clinical and Experimental Ophthalmology, vol. 37, pp. 118-129, 2009.
Nidek, "Refractive Power / Corneal Analyzer, OPD-Scan III," 6 pages, 2011.
Nidek "Wavefront Aberrometer: Refractive Power / Corneal Analyzer," https://web.archive.org/web/20131217075854/http://usa.nidek.com/products/wavefront-aberrometer, Dec. 2013.
Ophthalmictechnician.org, "To fog or not to fog?," http://www.ophthalmictechnician.org/index.php/tech-tips/160-to-fog-or-not-to-fog, 2 pages, Jan. 2014.
Tracey Technologies, Corp., Ophthalmic Diagnostic Products, http://www.traceytechnologies.com/products_iTrace.htm, 1 page, 2013.
Vessel, "Wavefront Technology in Eye Exams," http://www.allaboutvision.com/eye-exam/wavefront.htm, 5 pages, 2011.
Visser, et al., "Evaluation of the Comparability and Repeatability of Four Wavefront Aberrometers," Investigative Ophthalmology & Visual Science, vol. 52, No. 3, 10 pages, Mar. 2011.
WaveFront Sciences, COAS-VR Wavefront Aberrometer Technical Description, 2 pages, Apr. 19, 2010.
WaveTec Vision, "The ORA System Get ORA System," http://getorasystem.com/, 1 page, 2013.
WelchAllyn, Welch Allyn SureSight™ Autorefractor, 4 pages, 2006.
Wikipedia, "Accomodation (eye)," https://en.wikipedia.org/wiki/Accomodation_(eye), 5 pages, Aug. 5, 2012.
Wikipedia, "Autorefractor," https://en.wikipedia.org/wiki/Autorefractor, 2 pages, Oct. 29, 2012.
Wikipedia, "Cycloplegia," https://en.wikipedia.org/wiki/Cycloplegia, 2 pages, Jun. 28, 2012.
Wikipedia, "Eyeglass prescription," https://en.wikipedia.org/wiki/Eyeglass_prescription, 13 pages, May 28, 2012.
Wikipedia, "Shack-Hartmann wavefront sensor," https://en.wikipedia.org/wiki/Shack-Hartmann_wavefront_sensor, 2 pages, Apr. 9, 2012.
Win-Hall, et al., "Objective accommodation measurements in prepresbyopic eyes using an autorefractor and an aberrometer," Journal of Cataract & Refractive Surgery, vol. 34, pp. 774-784, May 2008.

* cited by examiner

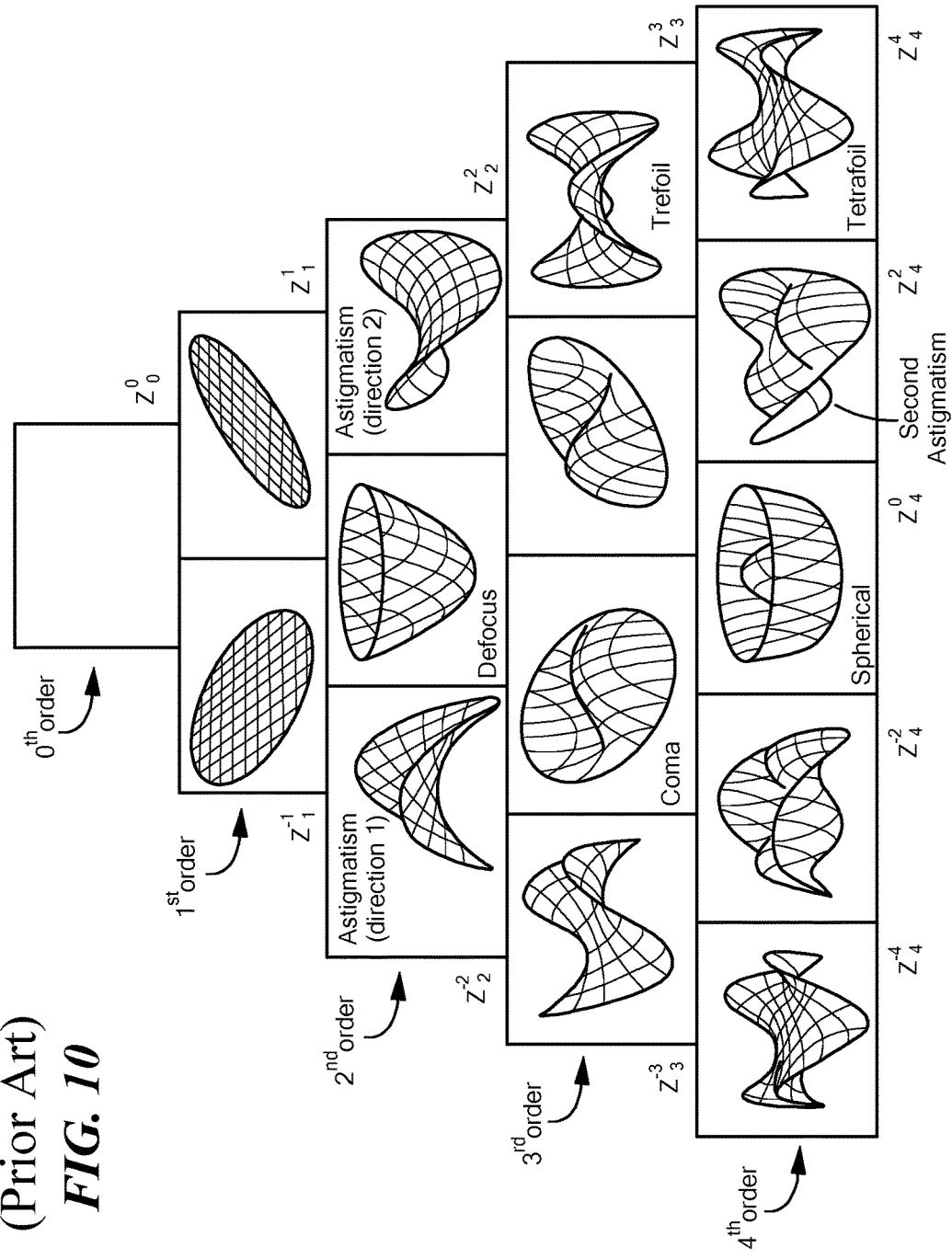
(Prior Art) FIG. 10

APPARATUS AND METHOD OF DETERMINING AN EYE PRESCRIPTION

CROSS REFERENCE TO RELATED APPLICATIONS

This application is a continuation of U.S. patent application Ser. No. 14/900,691, filed Dec. 22, 2015, titled "Apparatus and Method of Determining an Eye Prescription," which claims the benefit of U.S. Provisional Patent Application No. 61/842,190, filed Jul. 2, 2013, titled "System and Method for Optical Alignment of an Eye with a Device for Measurement of Optical Properties of the Eye," U.S. Provisional Patent Application No. 61/972,058, filed Mar. 28, 2014, titled "Apparatus and Method for Determining an Eye Prescription" and U.S. Provisional Patent Application No. 61/972,191, filed Mar. 28, 2014, titled "Apparatus and Method for Determining an Eye Prescription," the entire contents of each of which are hereby incorporated by reference herein, for all purposes.

TECHNICAL FIELD

The invention generally relates to optical or ophthalmologic methods and apparatus and, more particularly, the invention relates to methods and devices for facilitating the process of determining optical properties of an eye.

BACKGROUND ART

"Refractive errors" are low-order aberrations, such as in an eye of a human. A "refractive prescription" is a prescription for corrective lenses (eyeglasses) that correct refractive errors. As described in more detail herein, eyes may also or instead suffer from higher-order aberrations.

Autorefractors automatically estimate a refractive prescription for a patient's eyes. While widely used in the United States and Europe for many years, autorefractors have a number of drawbacks. For example, autorefractors typically are quite expensive, often costing more than ten thousand dollars. In addition, autorefractors generally are large and immobile, and they require extensive assistance by an ophthalmologist, optometrist or her trained staff. Accordingly, for these and other related reasons, autorefractors are used much less frequently in low-resource settings, such as parts of Africa, Asia and even rural portions of the United States. Wavefront aberrometers are a complex and expensive type of autorefractor. Wavefront aberrometers are also used to guide laser surgery, such as for cataracts and vision correction.

Prescriptions may be expresses in optometric notation, power vectors notation and their equivalence.

SUMMARY OF EMBODIMENTS

An embodiment of the present invention provides a method of determining optical properties of an eye system. The method includes enabling an expected user to support the entire weight of an open view optical apparatus with a hand of the expected user. The apparatus has a first proximal port and a distal port. The first proximal port and the distal port together form a visual channel from the first proximal port through the distal port. The expected user has full physical control of all degrees of freedom of movement of the apparatus. The method includes positioning the expected user's eye proximate the first proximal port. The eye is focused at effective infinity. An optical property of the eye is measured.

Focusing the eye may include focusing the eye at effective infinity by viewing target indicia external to the apparatus.

Focusing the eye may include focusing the eye at effective infinity at least partially through the visual channel.

The method may also include illuminating the eye to produce a wavefront through the proximal port and determining a wavefront error.

The method may also include calculating a refractive prescription from the wavefront error.

Viewing target indicia external to the apparatus may include viewing target indicia through the distal port.

The method may also include generating a target light beam by a target light source coupled to the apparatus and producing the target indicia with the target light beam.

Viewing target indicia may include viewing target indicia at least about 20 feet from the distal port.

Measuring the optical property of the eye may include measuring the optical property of the eye with a wavefront aberrometer within the apparatus.

The apparatus may include a second proximal port that, together with the first proximal port, forms a binocular configuration. The method may further include positioning the expected user's other eye proximate the second proximal port.

The method may further include focusing the other eye at effective infinity and measuring an optical property of the other eye.

The apparatus may include a handle. The method may include holding the handle by a hand of the expected user.

The method may include disposing a lens between the expected user's eye and the first proximal port and calculating whether a prescription of the eyeglass lens is correct, within a predetermined range, for the user's eye.

Calculating whether a prescription of the eyeglass lens is correct may include calculating whether a prescription of the eyeglass lens is correct, based on a determination of a wavefront error.

Disposing the lens between the expected user's eye and the first proximal port may include disposing at least two lenses between the expected user's eye and the first proximal port.

Disposing the lens between the expected user's eye and the first proximal port may include disposing a lens with known optical properties between the expected user's eye and the first proximal port. Calculating whether a prescription of the eyeglass lens is correct may include measuring the optical property of the eye using the known optical properties of the disposed lens.

Another embodiment of the present invention provides an optical apparatus that includes a non-stationary body having a proximal port configured to receive an eye. The body further has a distal port and forms a visual channel from the proximal port through the distal port. The visual channel is open view to enable the eye to see target indicia external to and spaced away from the body. Processing components within the body are configured to receive a wavefront received through the proximal port to contribute to determining optical properties of an eye system.

The optical apparatus may also include a battery, within the body, for powering the processing components.

The body may be free of a chin support.

The body may further include a handle for gripping by at least one hand of an expected user.

The body may be configured to make the apparatus portable.

The processing components may be configured to contribute to determining a prescription without operator interaction.

The body may be in a binocular configuration.

The processing components may be configured to calculate whether a prescription of an eyeglass lens disposed between the eye and the proximal port is correct, within a predetermined range, for the eye.

Yet another embodiment of the present invention provides an optical apparatus that includes a body having a proximal port. The proximal port is configured to receive an eye. The body further has a distal port and forms a visual channel from the proximal port through the distal port. The distal port at least in part defines an optical axis. A target light source is coupled with the body of the apparatus. The target light source is configured to generate a target light beam that produces target indicia on a target outside of the body. The target light source is configured to substantially align the target indicia with the optical axis. The optical apparatus also includes optics for determining a prescription for the eye.

The visual channel may be substantially linear.

The visual channel may have a plurality of diverging sub-channels.

The target light source may include a laser or a light emitting diode.

The target light source may include a laser or a light emitting diode with a spatially filtering element to project a pattern.

The target light source may include a laser or a light emitting diode with a spatially filtering element to project a pattern that varies in time.

The target light source may be fixedly coupled and stationary relative to the body.

The apparatus may also include optics within the body. The optics may have target indicia intersecting the optical axis.

The apparatus may also include a retinal light source that is configured to at least in part produce the fixed target indicia. The target light source may be configured to produce a retinal light beam through the proximal port.

The target indicia may include light.

The target indicia may include a physical object.

The target light source may be configured to coaxially substantially align at least a portion of the target light beam with the optical axis.

The target light source may be configured to cause at least a portion of the target light beam to form an angle with the optical axis.

The target light source may be configured to cause at least a portion of the target light beam to be generally parallel with and spaced from the optical axis.

The body may form a second channel having a second proximal port and a second distal port. The body may form a binocular configuration.

The second channel may be free of optics for determining the eye's prescription.

An embodiment of the present invention provides a method of determining an eye prescription or ocular aberrations of an optical system. The method includes providing an optical apparatus having a proximal port and a distal port that together form a visual channel. The distal port at least in part defines an optical axis. The optical apparatus also has a target light source configured to generate a target light beam that produces target indicia. The optical system is substantially aligned with the proximal port. The target indicia are formed on a target outside of the optical apparatus. The target indicia are substantially aligned with the optical axis. An eye of the optical system is illuminated with a retinal light source that produces a wavefront. Wavefront aberrometry is used to determine ocular aberrations of the eye.

The optical system being characterized may be an eye of a living being.

The optical system being characterized may be an eye of a living being and a corrective lens.

The ocular aberrations for the eye may be obtained after aligning the target indicia with the optical axis.

Forming the target indicia may include forming visual indicia that is visible to the eye through the distal port. The visual indicia may be formed from another light source. Aligning the target indicia with the optical axis may include aligning the visual indicia with the optical axis.

Forming the target indicia may include forming visual indicia from a physical object that is visible to the eye. Aligning the target indicia with the optical axis comprises aligning the visual indicia with the optical axis.

The target may be at least about 20 feet from the apparatus.

Aligning the target indicia with the optical axis may include moving closer to, or farther away from, the target.

The target may be a known distance from the apparatus. The method may include using the known distance to estimate the ocular aberration, based on an assumption that the eye was focusing at a target greater than 20 feet away.

An embodiment of the present invention provides an optical method that includes providing an optical apparatus. The optical apparatus has a proximal port and a distal port that together form a visual channel. The distal port at least in part defines an optical axis. A living being's eye is aligned with the proximal port. The eye views through the distal port to target indicia exterior of the apparatus. Orientation of the eye is determined, relative to the optical axis. A cue is generated, as a function of the orientation of the eye relative to the optical axis. The cue is perceptible to a human being.

The cue may include a visual cue, an acoustic cue and/or a mechanical cue.

Generating the cue may include producing a sound that changes in amplitude, as a function of the orientation of the eye relative to the optical axis.

Generating the cue may include producing a sound that changes in frequency, as a function of the orientation of the eye relative to the optical axis.

Generating the cue may include producing a sound that changes in duty cycle, as a function of the orientation of the eye relative to the optical axis.

Determining the orientation of the eye may include using wavefront aberrometry techniques.

The optical apparatus may include a plurality of target light sources. Each target light source may be configured to selectively generate the target indicia. The method may also include alternatively illuminating one or more of the target light sources to direct the eye toward alignment with the optical axis.

The optical apparatus may include a target light source that is configured to produce a light beam for forming the target indicia. The method may also include moving the target light source to direct the eye toward alignment with the optical axis.

The eye may move toward alignment with the optical axis in response to generation of a cue.

Yet another embodiment of the present invention provides an optical apparatus for measuring ocular aberrations of an eye of a living being. The apparatus includes a proximal port and a distal port that together form a visual channel from the proximal port through the distal port. The distal port at least in part defines an optical axis. A cue generator is configured to generate a cue perceptible to a human being. Orientation logic is operatively coupled to the cue generator and the visual channel and is configured to determine orientation of the living being's eye relative to the optical axis and to cause operation of the cue generator as a function of the orientation.

The cue generator may be configured to produce a visual cue, an acoustic cue and/or a mechanical cue.

The optical apparatus may also include an open-view visual channel.

The visual channel may have a conic shape, with a vertex of the conic shape toward the proximal port and a base of the conic shape toward the distal port.

The optical apparatus may also include a wavefront aberrometer.

The optical apparatus may also include a body in a binocular configuration.

The optical apparatus may also include a plurality of target light sources. Each target light source may be configured to selectively generate target indicia. A controller may be configured to alternatively illuminate one or more of the target light sources to direct the eye toward alignment with the optical axis.

The optical apparatus may also include a target light source configured to generate target indicia. The target light source may be configured to illuminate a light beam that is movable relative to the distal port.

Illustrative embodiments of the invention may be implemented as a computer program product having a computer usable medium with computer readable program code thereon. The computer readable code may be read and utilized by a computer system in accordance with conventional processes.

BRIEF DESCRIPTION OF THE DRAWINGS

The invention will be more fully understood by referring to the following Detailed Description of Specific Embodiments in conjunction with the Drawings, of which:

FIG. 10 provides perspective views of surface shapes defined by 1st to 4th order Zernike polynomials, according to the prior art.

FIG. 15-1 is a schematic diagram illustrating an eye properly aligned with the device of FIGS. 11-15, as well as a view as seen by the eye through the device, according to an embodiment of the present invention.

FIG. 15-2 is a schematic diagram illustrating an eye slightly misaligned with the device of FIGS. 11-15, as well as a hypothetical view as seen by the eye through the device, according to an embodiment of the present invention.

FIG. 15-3 is a schematic diagram illustrating an eye grossly misaligned with the device of FIGS. 11-15, as well as a view as seen by the eye through the device, according to an embodiment of the present invention.

FIG. 23-1 illustrates a binocular lightweight portable hand-held automatic device that includes a Hartmann-Shack wavefront aberrometer, according to another embodiment of the present invention.

DETAILED DESCRIPTION OF SPECIFIC EMBODIMENTS

In accordance with preferred embodiments of the present invention, methods and apparatus are disclosed for calculating a prescription to correct refractive errors with a relatively inexpensive, light-weight, portable instrument that does not require a professional clinician, cycloplegic agent, fogging or virtual images. Some embodiments also calculate prescriptions to correct higher-order aberrations in an eye and/or additional optical properties of the eye. Some embodiments may be used to calculate prescriptions for corrective lenses (eyeglasses) and/or to check whether an existing eyeglass has a correct prescription of a patient.

INTRODUCTION

Figure 1:
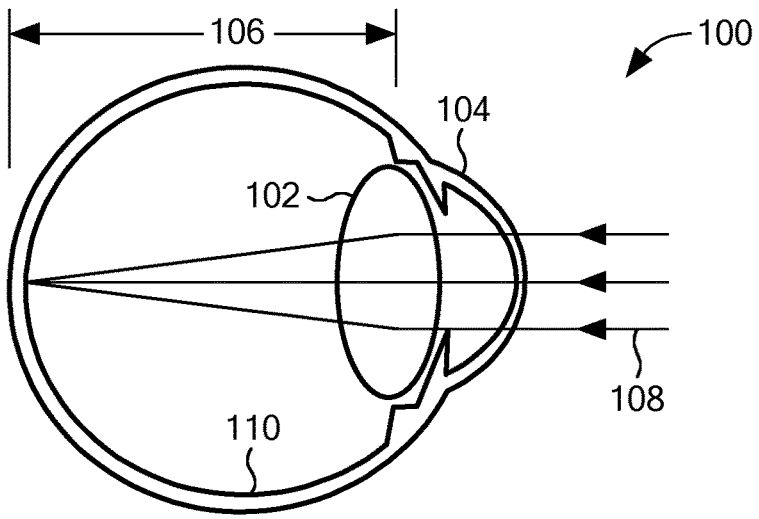
FIG. 1 is a schematic cross-sectional diagram of an emmetropic human eye imaging a distant object.

FIG. 1 is a schematic cross-sectional diagram of a normal emmetropic human eye 100. Emmetropia describes a state of vision where an object at infinity is in sharp focus, with the eye's crystalline lens 102 in a neutral (relaxed or "unaccommodated") state. This condition of the normal eye 100 is achieved when the refractive optical power of the cornea 104 and lens 102 balance the axial length 106 of the eye 100, thereby focusing rays 108 from a distant object (not shown) exactly on the retina 110, resulting in perfect vision. Here "distant" means more than 20 feet (6 meters) away. An eye in a state of emmetropia requires no correction.

Figure 2:
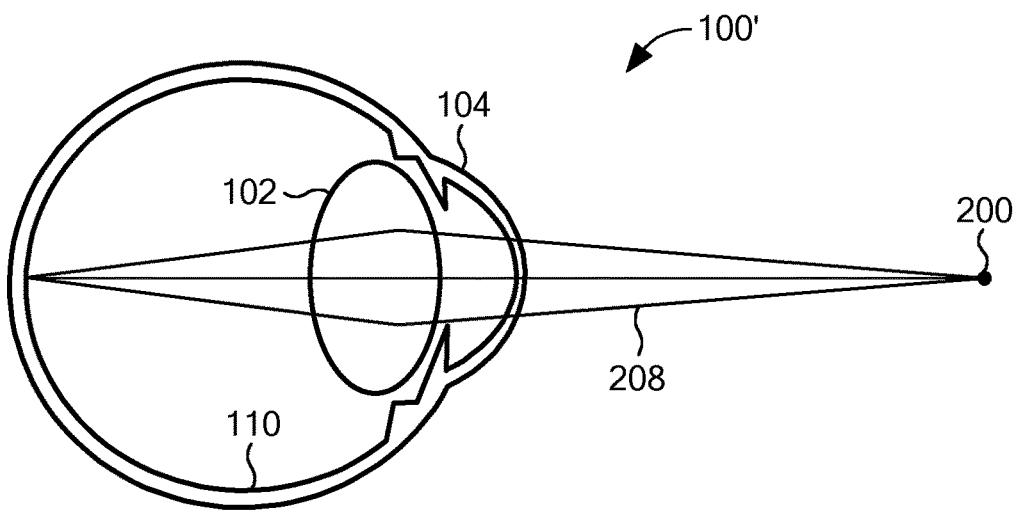
FIG. 2 is a schematic cross-sectional diagram of an emmetropic human eye imaging a close object.

If gaze shifts to a close object 200, as shown schematically in FIG. 2, ciliary muscles (not shown) change the shape of the lens 102, thickening it, thereby increasing its optical power, so the eye 100 focuses the rays 208 on the retina 110. This process is referred to as "accommodation." Thus, absent effort by the ciliary muscles, the eye 100 automatically focuses on objects in the distance. However, focusing on close objects requires effort. Humans naturally, and typically unconsciously, automatically focus on objects of interest. However, with age, the lens 102 becomes increasingly stiff and the ciliary muscles loose some degree of contractility, thereby making it progressively more difficult to focus on close objects. Typically by age 45 to 50 it becomes impossible to focus on objects at book-reading distance, thereby requiring reading glasses.

Figure 3:
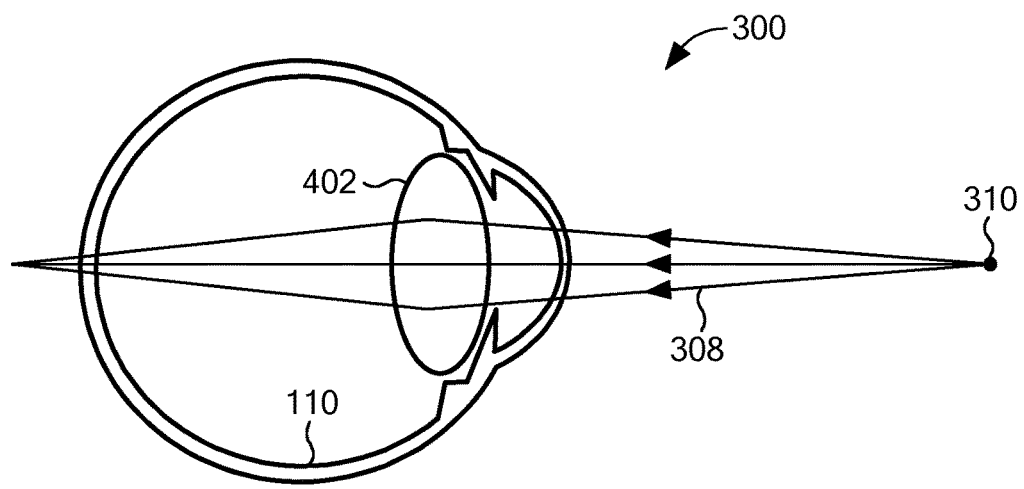
FIG. 3 is a schematic cross-sectional diagram of a hyperopic human eye imaging a close object.
Figure 4:
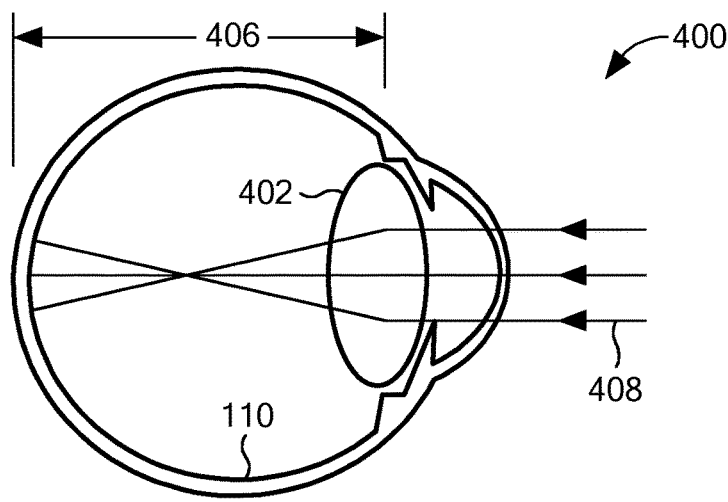
FIG. 4 is a schematic cross-sectional diagram of a myopic human eye imaging a distant object.

FIGS. 1 and 2 illustrate normal eyes. However, various imperfections in the shape or composition of the lens 102, cornea 104, retina 110 or the eye 100 in general can prevent the eye 100 from perfectly focusing the rays 108 or 208 on the retina 110, even in young people. These imperfections prevent the eye 100 from bending (refracting) light rays as a normal eye would, thereby causing "refractive errors." For example, FIG. 3 schematically illustrates a hyperopic (farsighted) eye 300, in which light rays 308 from a close object 310 are too divergent to focus on the retina 110, leading to blurry vision. Similarly, FIG. 4 schematically illustrates a myopic (nearsighted) eye 400, in which light rays 408 from a distant object (not shown) focus in front of the retina 110, causing the distant object to appear blurry. Essentially, the lens 402 of a myopic eye has too much optical power, relative to the axial length 406 of the eye 400. Myopic eyes can, however, focus well on near objects. In both myopia and hyperopia, an inability to create a sharp image of an object on the retina is referred to as a "defocus error." Imperfections in eyes can be congenital or result from other factors such as an injury or a disease.

Figure 5:
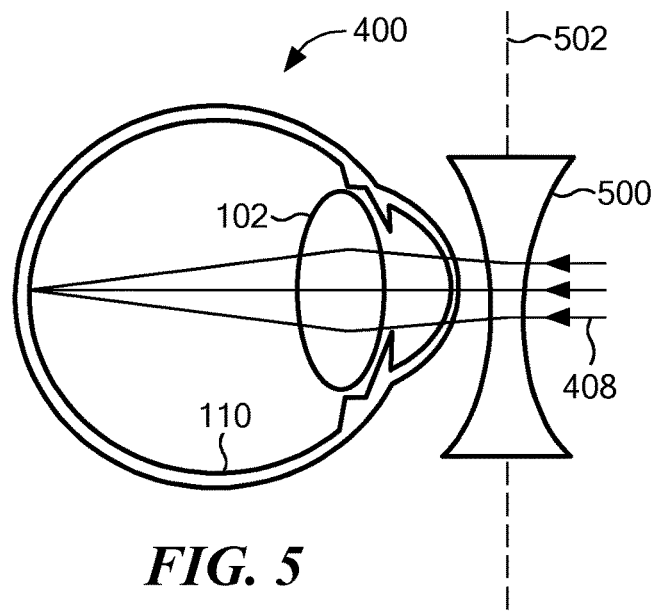
FIG. 5 schematically illustrates a corrective lens disposed in front of the myopic eye of FIG. 4 to correct the myopia.

These and other imperfections in eyes can be treated by prescribing eyeglasses ("spectacles") or contact lenses, which introduce corrective lenses in front of the eyes. FIG. 5 schematically illustrates a corrective lens 500 disposed in front of the myopic eye 400 of FIG. 4 to correct the myopia. The lens 500 is disposed in a "spectacle plane" 502 located a small distance away from the eye 400. The spectacle plane 502 defines where eyeglasses are worn, relative to the eye 400. In the case of a contact lens, the spectacle plan is close to the outer layer of the cornea. A lens to correct myopia has a negative optical power, i.e., it has a net concave effect, which counteracts the excessive positive optical power of the myopic eye. For simplicity, the following descriptions refer to eyeglasses or spectacles, although they also apply to contact lenses.

A prescription for corrective eyeglasses specifies all aspects of the lenses of the eyeglasses. Some eye imperfections are simpler to correct than others. For example, if an eye is only hyperopic or only myopic, a spherical lens can be used to correct the defocus errors of the eye. A spherical lens includes a surface that is a portion of a sphere. However, if the crystalline lens 102 (FIG. 1), the cornea 104, the retina 110 or the eye 100 in general is not properly shaped, for example if the focusing power of the eye is different along different axes, a simple spherical lens cannot fully correct the eye. In this case, the eye is referred to as having "astigmatism." Corrective eyeglasses that have a spherical and a cylindrical component are used to correct astigmatism. Spherical and cylindrical imperfections account for most, but not all, of the eye's imperfections. Spherical and cylindrical imperfections are referred to as low-order aberrations.

Thus, most prescriptions include a spherical component and a cylindrical component to correct low-order aberrations. The spherical component corrects the defocus error and is described in terms of the optical power, positive or negative, of the corrective lens, typically expressed as a number of diopters. A diopter is a unit of measurement of optical power of a lens, which is equal to a reciprocal of the focal length (f) of the lens measured in meters, i.e., 1/f. The cylindrical component is described in terms of power and axis of a cylindrical lens. Typically, one or two axes are specified, corresponding to one or two cylindrical lenses. Each axis is specified as an angle. The resulting corrective lens has a compound surface shape that includes spherical and cylindrical components, as described by the prescription, to compensate for the defocus and astigmatism imperfections in the eye.

An "aberration" is a departure of the optical performance of an eye from a perfect eye. Thus, defocus and astigmatism imperfections are examples of aberrations. However, eyes may suffer from more complex imperfections, which are commonly referred to as "higher-order aberrations." Examples of higher-order aberrations include coma and spherical aberration (not to be confused with the low-order spherical imperfections that cause defocus errors, as described above). Coma causes an off-axis point source to appear distorted, appearing to have a tail. Spherical aberrations cause collimated rays entering the eye far from the optical axis to focus at a different position than collimated rays entering the eye close to the optical axis. Some prescriptions at least partially correct for higher order aberrations, although determining these prescriptions requires large, heavy, expensive, fixed (such as to a desk) diagnostic equipment and highly skilled clinicians.

Optical professionals use various tools and methods to generate eyeglass prescriptions. Some methods are subjective, others are objective. For example, a phoropter allows a clinician to position various combinations of lenses, at various angles, in front of a patient and ask the patient whether one combination is better than a different combination for visualizing a target. Based on reports from the patient, a skilled clinician can achieve progressively better combinations, eventually arriving at a good, although not necessarily perfect, prescription. However, the accuracy of the prescription depends in large part on the patient's reporting accuracy. Phoropters are relatively inexpensive, but the above-described process is time consuming.

An aberrometer (wavefront sensor) objectively measures how light is changed by an eye, thereby identifying and quantifying refractive errors caused by the eye. Aberrometers are usually classified into three types: (1) outgoing wavefront aberrometers, such as a Hartmann-Shack sensor; (2) ingoing retinal imaging aberrometers, such as a cross-cylinder aberrometer or Tscherning aberrometer or as used in a sequential retinal ray tracing method; and (3) ingoing feedback aberrometers, such as a spatially-resolved refractometer or as used in an optical path difference method.

Figure 6:
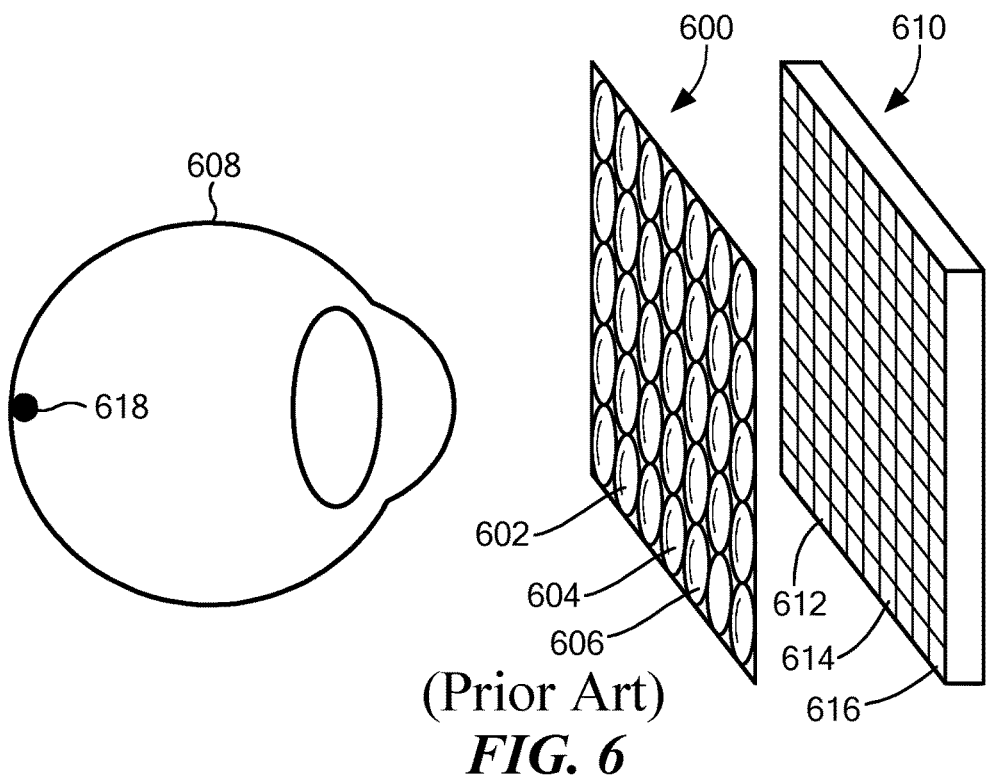
FIG. 6 schematically illustrates a Hartmann-Shack wavefront aberrometer adjacent an emmetropic human eye, according to the prior art.

As schematically illustrated in FIG. 6, a Hartmann-Shack wavefront aberrometer includes an array 600 of lenses ("lenslets"), exemplified by lenslets 602, 604 and 606. All the lenslets 602-606 have identical sizes and focal lengths, within some manufacturing tolerances. The lenslet array 600 is disposed optically between an eye 608 and an optical sensor 610, such as a pixelated charge-coupled device (CCD), pixelated complementary metal oxide semiconductor (CMOS) device or an array of quadrant photodiode detectors. Each lenslet 602-606 is focused onto a portion of the optical sensor 610. Thus, light from a single point source is focused by the lenslet array 600 onto the optical sensor 610 to create an array of spots of light.

Each lenslet 602-606 may, but need not, be focused on the center of a respective pixel of a pixelated CCD array or on the center of a respective quadrant sensor. The optical sensor 610 is configured to have sufficient spatial resolution to enable a circuit or processor to measure displacement of each spot of the array of spots from a position directly in line with the center of the corresponding lenslet, as described in more detail below. A point 618 within the eye 608 is illuminated by shining a light, typically from a laser or a superluminescent diode (SLED or SLD), into the eye 608, thereby creating a "virtual point light source" within the eye 608. The term "virtual light source" is a term of art used in wavefront aberrometry, and as used herein, the term means a place where light appears to emanate, although no light is actually generated there. In the case of point 618, the laser or SLED creates the virtual light source. As used herein, unless context indicates otherwise, "virtual" should not be confused with that term as used in optics, where "virtual" means a physical source that is imaged to another location.

Figure 7:
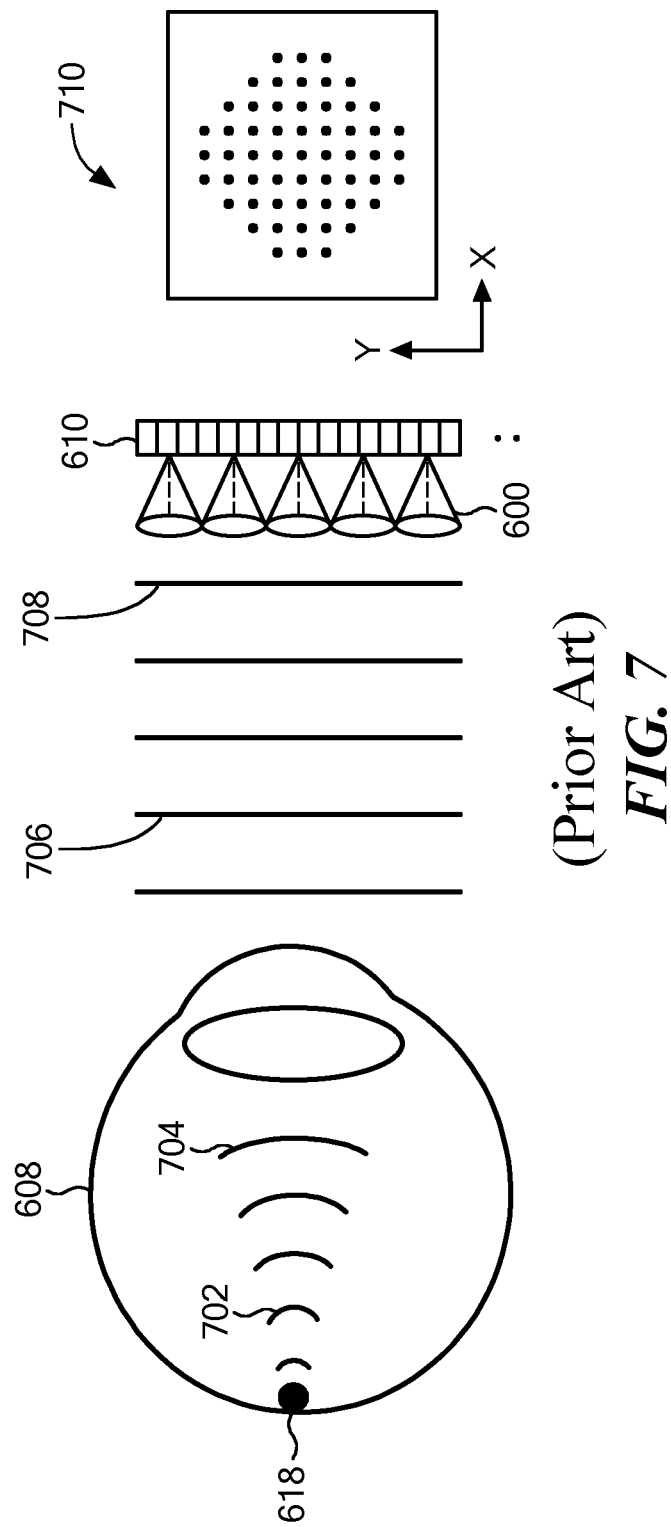
FIG. 7 schematically illustrates wavefronts from a virtual light source exiting the eye of FIG. 6 and received by the Hartmann-Shack wavefront aberrometer, as well as a hypothetical spot diagram generated by the Hartmann-Shack wavefront aberrometer, according to the prior art.

As schematically illustrated in FIG. 7, light reflects from the point 618 and exits the eye 608. Wavefronts 702, 704, 706, and 708 represent the exiting light. Each lenslet of the array of lenslets 600 focuses a respective portion of each wavefront 700-706 onto a corresponding portion of the optical sensor 610, creating a circular array of spots. A hypothetical array of spot 710 (also referred to herein as a "spot diagram") is shown, although the array of lenslets 600 may include more or fewer lenslets than are shown and, therefore, the spot diagram 710 may include more or fewer spots than are shown. If the eye 608 is perfectly shaped (emmetropic) and unaccommodated, the wavefronts 706-708 are planar, and the spots of the spot diagram 710 are equally displaced from the center of each individual lenslet. The outer perimeter of the spot diagram is a projection of the pupil of the eye 608, thus the diameter of the outer perimeter of the spot diagram indicates the pupil diameter.

Figure 8:
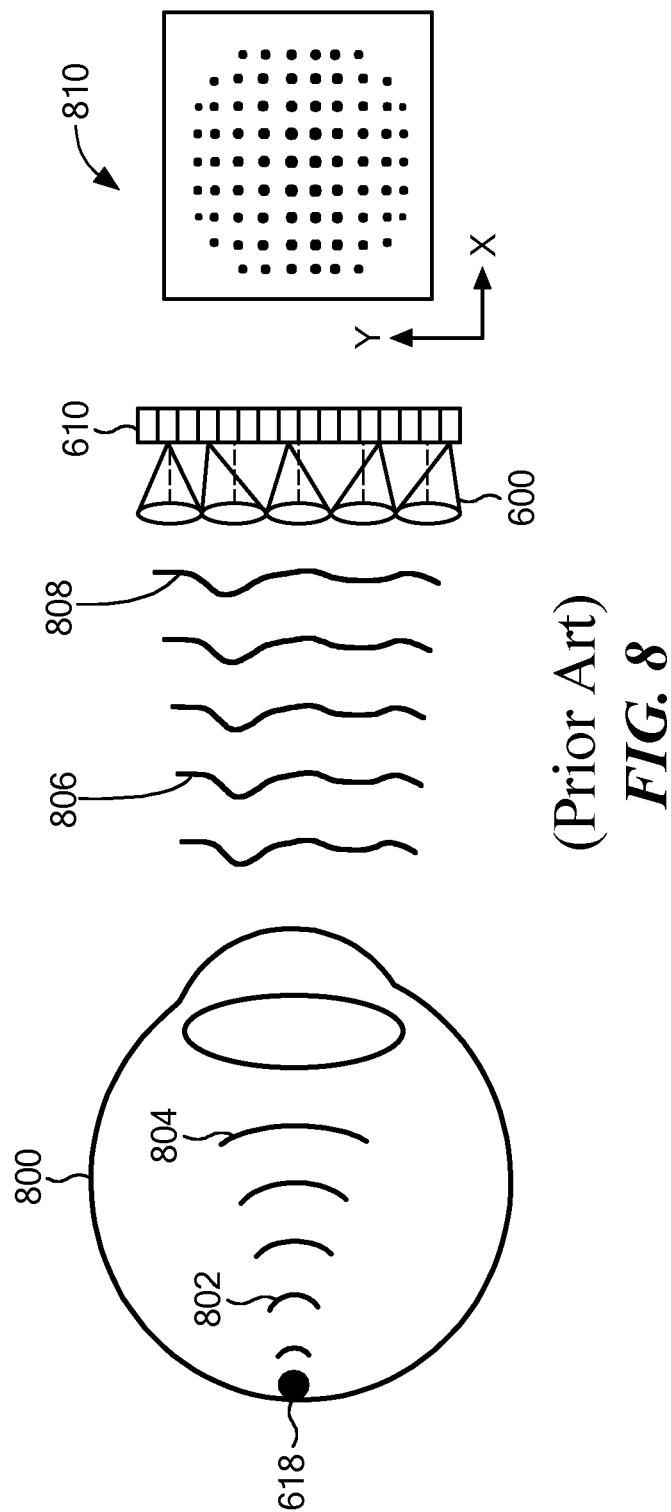
FIG. 8 schematically illustrates wavefronts from a virtual light source exiting a non-emmetropic eye and received by a Hartmann-Shack wavefront aberrometer, as well as a hypothetical spot diagram generated by the Hartmann-Shack wavefront aberrometer, according to the prior art.
Figure 9:
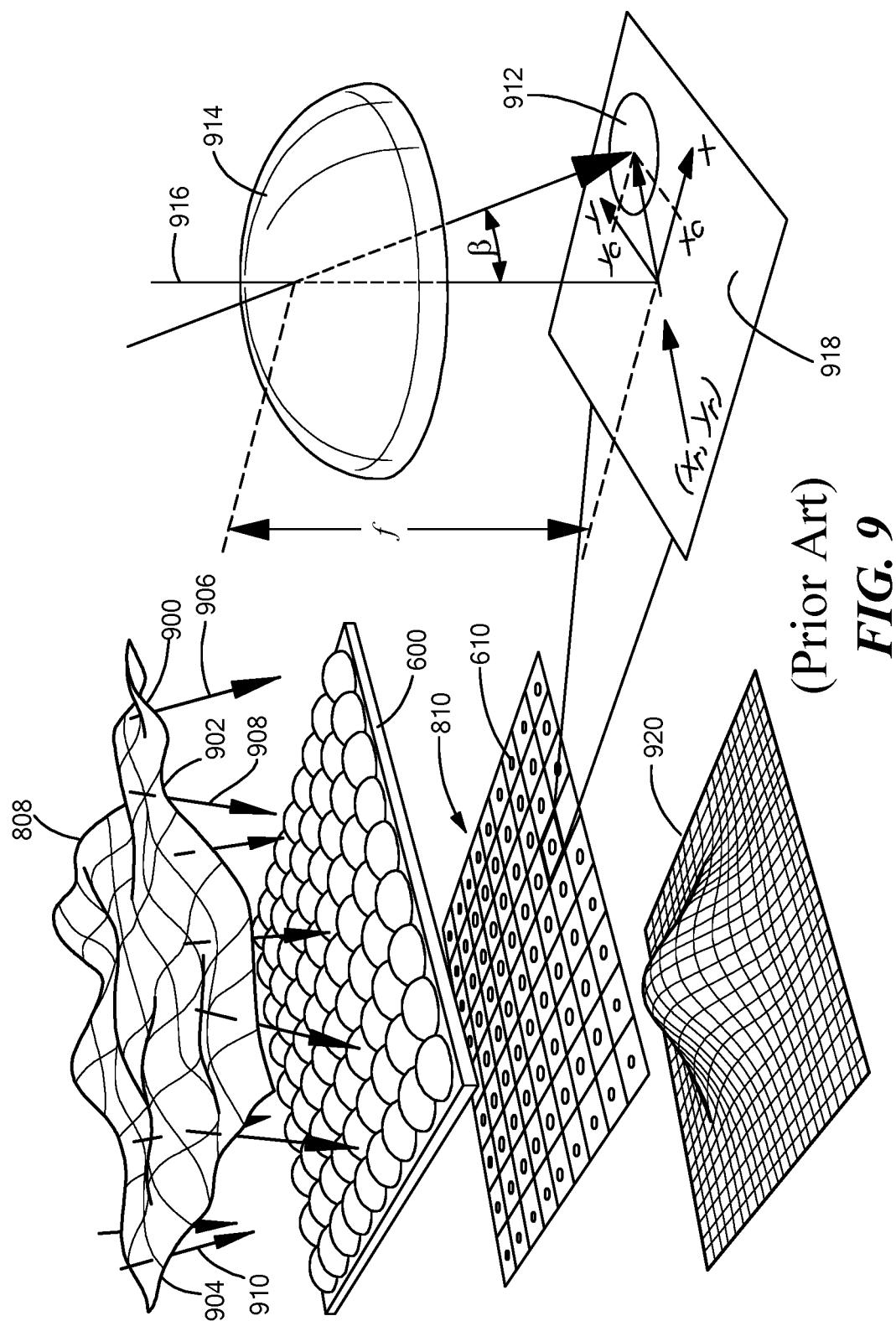
FIG. 9 is schematically illustrates a hypothetical wavefront from a non-emmetropic eye impinging on an array of lenslets of a Hartmann-Shack wavefront aberrometer and resulting illumination of an optical sensor of the aberrometer and a three-dimensional graph representing geographic distribution of intensity of the illumination, as well as an enlarged view of one lens of the array of lenslets, according to the prior art.

However, as schematically illustrated in FIG. 8, if the eye 800 is aberrated, the wavefronts 806-808 exiting the eye 800 are non-planar. The shape of the wavefronts 806-808 is determined by the lower-order and higher-order aberration(s) of the eye 800. FIG. 9 schematically illustrates wavefront 908 conceptually divided into square regions, exemplified by regions 900, 902 and 904. Each region 900-904 impinges on the lenslet array 600 along a direction substantially perpendicular to the region, as indicated by respective arrows 906, 908 and 910. Thus, the spots of the spot diagram 810 (FIG. 8) are displaced from where they would be if the wavefront 808 were planar.

One such displaced spot 912 is shown in an enlarged portion of FIG. 9. Here, if the region of the wavefront 808 contributing the spot 912 had been parallel to the lenslet array 600, the region would have traveled through the lenslet 914 and impinged on the optical sensor 610 along a line 916 normal to the optical sensor 610 and created a spot at location 918. However, due to the tilt of the wavefront region caused by the aberrated eye, the spot 912 is displaced an x and a y distance from the location 918.

Conventional centroid finding methods may be used to analyze data from the optical sensor 610 to calculate the x and y displacements and angles β for each lenslet, often with sub-pixel resolution. Thus, a local tilt of the wavefront 908 across each lenslet can be calculated from the position of the spot on the optical sensor 610 generated by the lenslet. Any phase aberration can be approximated to a set of discrete tilts. By sampling signals from the elements of the optical sensor 610, all these tilts can be measured, and the whole wavefront can be reconstructed and characterized as numerical wavefront data. The wavefront data can then be used to characterize the eye 800 (FIG. 8) as an optical system.

Using the displacements of each spot, it is possible to reconstruct an analytical representation of the wavefront. For example, the shape of the wavefront 808 can be expressed as a weighted sum of a set of pre-determined three-dimensional surface shapes or basis functions. Each shape of the set is usually defined by an independent polynomial function which represents a specific aberration term. Among all the possible sets of basis functions, it is common to use the Zernike polynomials. The Zernike polynomials are appropriate for describing very complex shapes, such as wavefront aberrations, because of they are orthonormal over circular pupils and, more importantly, because they are constructed in such a way that higher-order polynomials are "balanced" by lower-order polynomials so that the image intensity at the focal plane can be optimized when the amount of aberration is low. FIG. 10 illustrates the shapes defined by the 0th through 4th orders (modes) of the Zernike polynomials. The views in FIG. 10 are perspective. However, often these shapes are shown in top view, using color gradients to represent powers of the aberrations. The shapes become increasingly complex with increased order, and these shapes can be combined to precisely describe a surface that fits as well as possible to a measured wavefront.

Each order describes a surface shape that corresponds with an ocular aberration. The 0th order has one term ($Z_0^0$) that represents a constant. The 1st order has two terms ($Z_1^{-1}$ and $Z_1^1$) that represent tilt for the x and y axes. The 2nd order includes three terms that represent defocus and regular astigmatism in two directions. The 3rd order has four terms that represent coma and trefoil. The 4th order has five terms that represent tetrafoil, secondary astigmatism and spherical aberration. The 5th order (not shown) has six terms that represent pentafoil aberration. The polynomials can be expanded up to an arbitrary order, if a sufficient number of measurements are made for the calculations and the optical sensor provides sufficient spatial resolution.

Thus, Zernike analysis describes a wavefront mathematically as a weighted sum of Zernike polynomials. The weight applied to each mode when computing this sum is called a Zernike coefficient and is usually expressed in microns. The weighted sum of the Zernike polynomials equals a description of all the aberrations, i.e., a total refractive error, of an eye. In practice, a Zernike analysis includes a finite number of modes. Once the total refractive error of an eye has been ascertained to a desired accuracy, i.e., using a desired number of Zernike modes, a corrective lens prescription can be calculated to compensate for the refractive error in a well-known manner. Thus, a spot diagram can be used to calculate a prescription.

Because no two eyes yield identical sets of Zernike coefficients (assuming a sufficient number of Zernike modes), the Zernike coefficients can be used somewhat analogously to a fingerprint to uniquely identify an individual eye and, therefore, an individual person.

Optical properties of an eye include: scattering (which may be used to determine if a patient has cataracts), wavefront (which may be used to measure refraction, low-order aberrations, high-order aberrations, accommodation, keratoconus, which is a high-order spherical aberration, and the like) and pupil size.

All prior art methods and apparatus for determining eyeglass prescriptions have associated problems. For example, phoropters required skilled clinicians and rely on subjective reports from patients. Hartmann-Shack wavefront aberrometers require ciliary muscles to be temporarily paralyzed by a cycloplegic agent, the eye to be "fogged" or the patient to be shown a virtual image at infinity, so as to prevent accommodation while the eye is measured.

Accommodation introduces an uncontrolled variable into the measurement process. Fogging refers to temporarily disposing a lens with positive spherical power in front of a patient's eye in an attempt to control accommodation. The goal of fogging is to move the focal point in front of the retina, regardless of the distance to the object. Essentially, the patient is temporarily made artificially myopic. As noted, the eye accommodates by changing the shape of the lens to increase its optical power in order to see close objects more clearly. However, if an eye is fogged, and the eye accommodates, vision becomes blurrier, not clearer, regardless of the distance to the object, thus discouraging accommodation. Some patients do not respond well to fogging.

Virtual images are images created within a diagnostic instrument but that optically are located at least 20 feet (6 meters) from the patient. However, when a patient looks into a relatively small (compared to 20 feet) instrument, the patient intuitively knows the viewed object is not 20 feet away and, therefore, the patient tends to accommodate. This phenomenon is sometimes referred to as "instrument-induced myopia," and it is difficult to avoid, even with fogging techniques.

Most ophthalmological diagnostic equipment is large, heavy and mechanically complex, at least in part because the equipment is designed to hold a patient's head steady and align it, and thereby align the patient's eye, with certain optical elements within the diagnostic equipment. Consequently, this equipment is typically attached to a table and includes heavy-duty structural members, forehead and chin rests and rack and pinion alignment mechanisms.

Lightweight Portable Automatic Hartmann-Shack Wavefront Aberrometer

Figure 12:
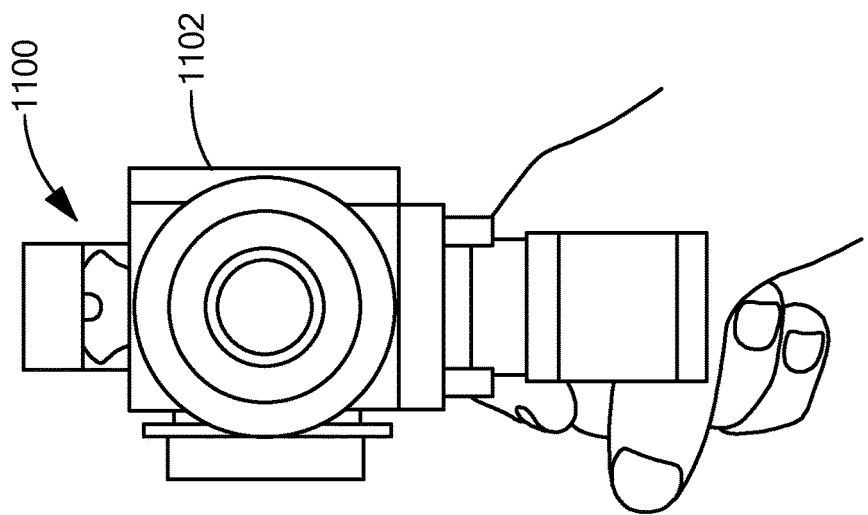
FIGS. 11, 12 and 13 contain right, front and left side views of a lightweight portable hand-held automatic device that includes a Hartmann-Shack wavefront aberrometer, according to an embodiment of the present invention.
Figure 11:
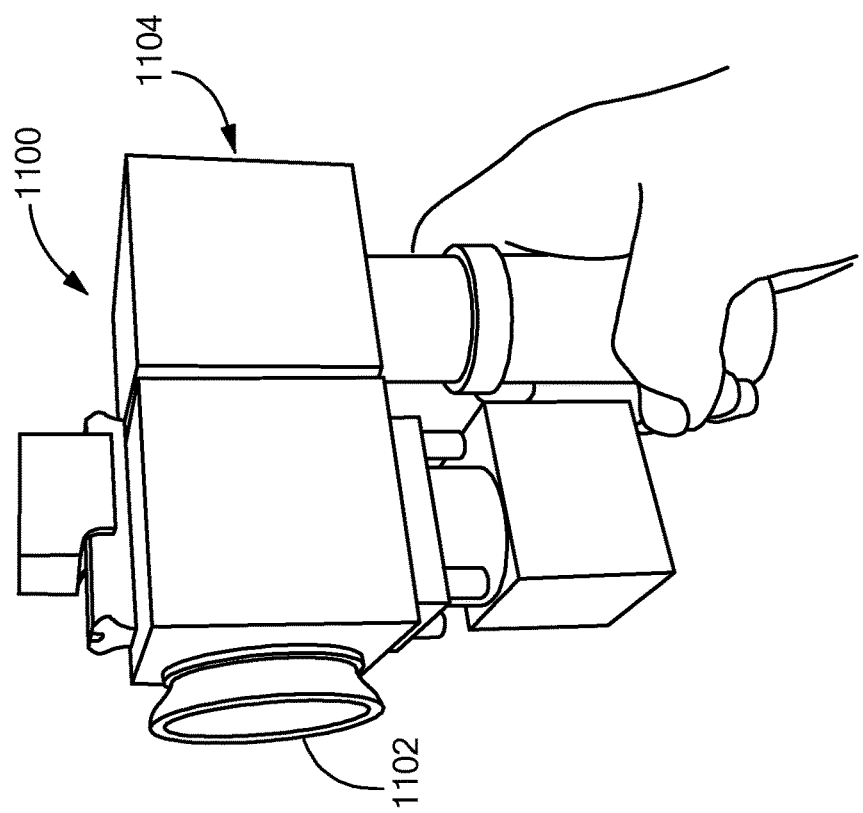
Figures 13, 14:
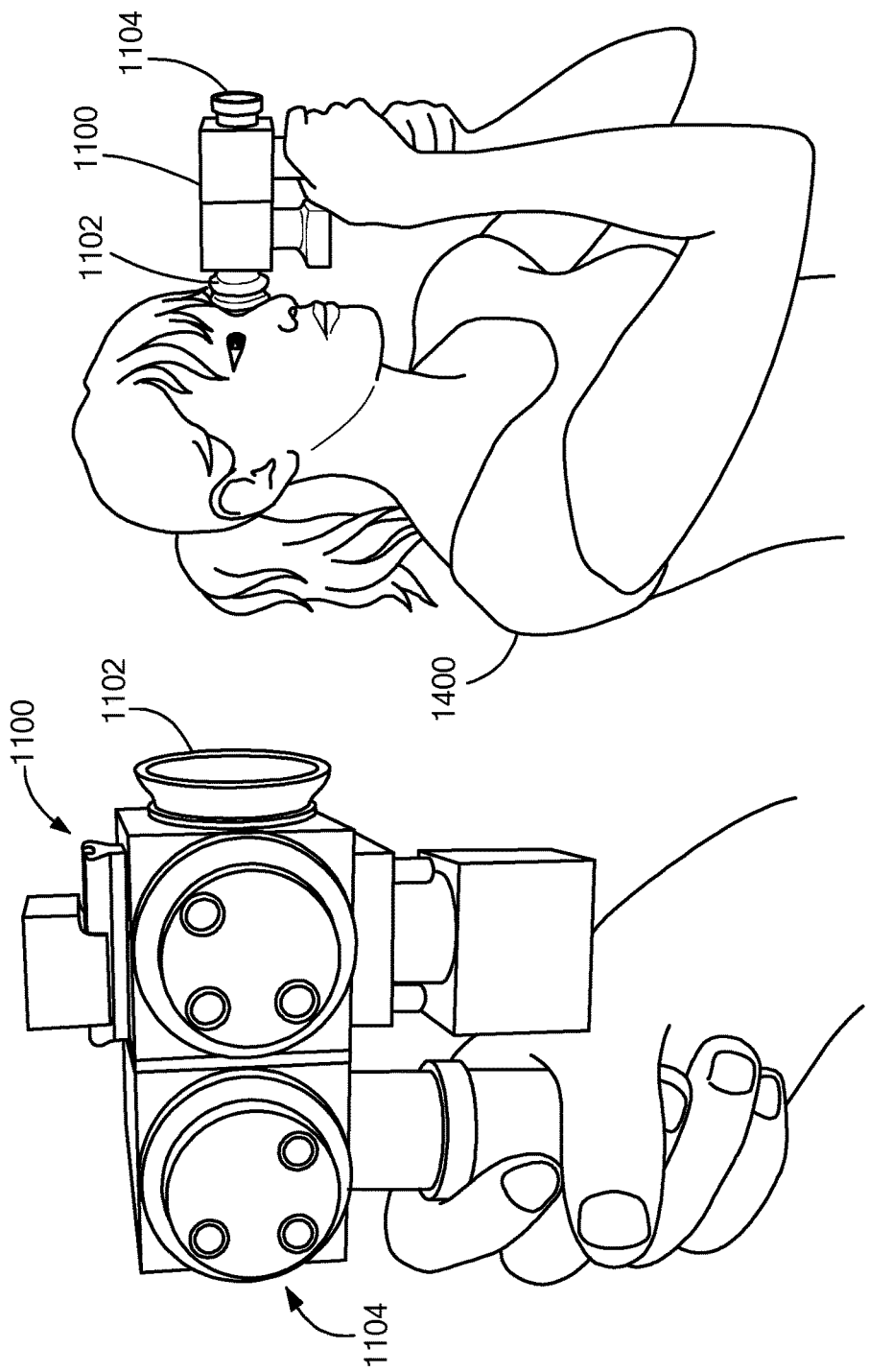
FIG. 14 illustrates the device of FIGS. 11-13 in use by a patient.

FIGS. 11, 12 and 13 contain various views of a lightweight, portable, hand-held, self-contained, automatic optical or ophthalmologic apparatus 1100 that includes a Hartmann-Shack wavefront aberrometer, according to an embodiment of the present invention. FIG. 14 shows the apparatus 1100 in use by a patient 1400. The apparatus 1100 solves many of the problems associated with the prior art. For example, the apparatus 1100 provides feedback to the patient 1400, enabling the patient 1400 to correctly align the apparatus 1100 to the patient's eye, without the cumbersome mechanical paraphernalia required by prior art devices. Furthermore, the apparatus 1100 is of an "open view" design, therefore it is configured to inherently encourage the patient 1400 not to accommodate, without any cycloplegic agents, fogging or virtual images. The apparatus 1100 automatically determines when the patient 1400 is not accommodating, and uses data acquired during a period of non-accommodation to automatically calculate an eyeglass prescription. Alternatively, the apparatus 1100 can measure the optical properties of an eye that is focused at a known, non-infinite distance, and these optical properties can be used to calculate the patient's eye's optical properties if the patient were to focus at infinity.

The apparatus 1100 includes an eyepiece 1102, into which the patient 1400 looks with one eye. The eyepiece 1102 may include an eyecup configured to be pressed against the patient's face, thereby blocking ambient light. The eyecup may be sized and shaped differently to fit well against various facial geometries and anatomical configurations, such as young and old patients. The apparatus 1100 also defines an exit port 1104, through which the patient 1400 can see. Thus, the apparatus 1100 has an "open view" configuration.

Figure 15:
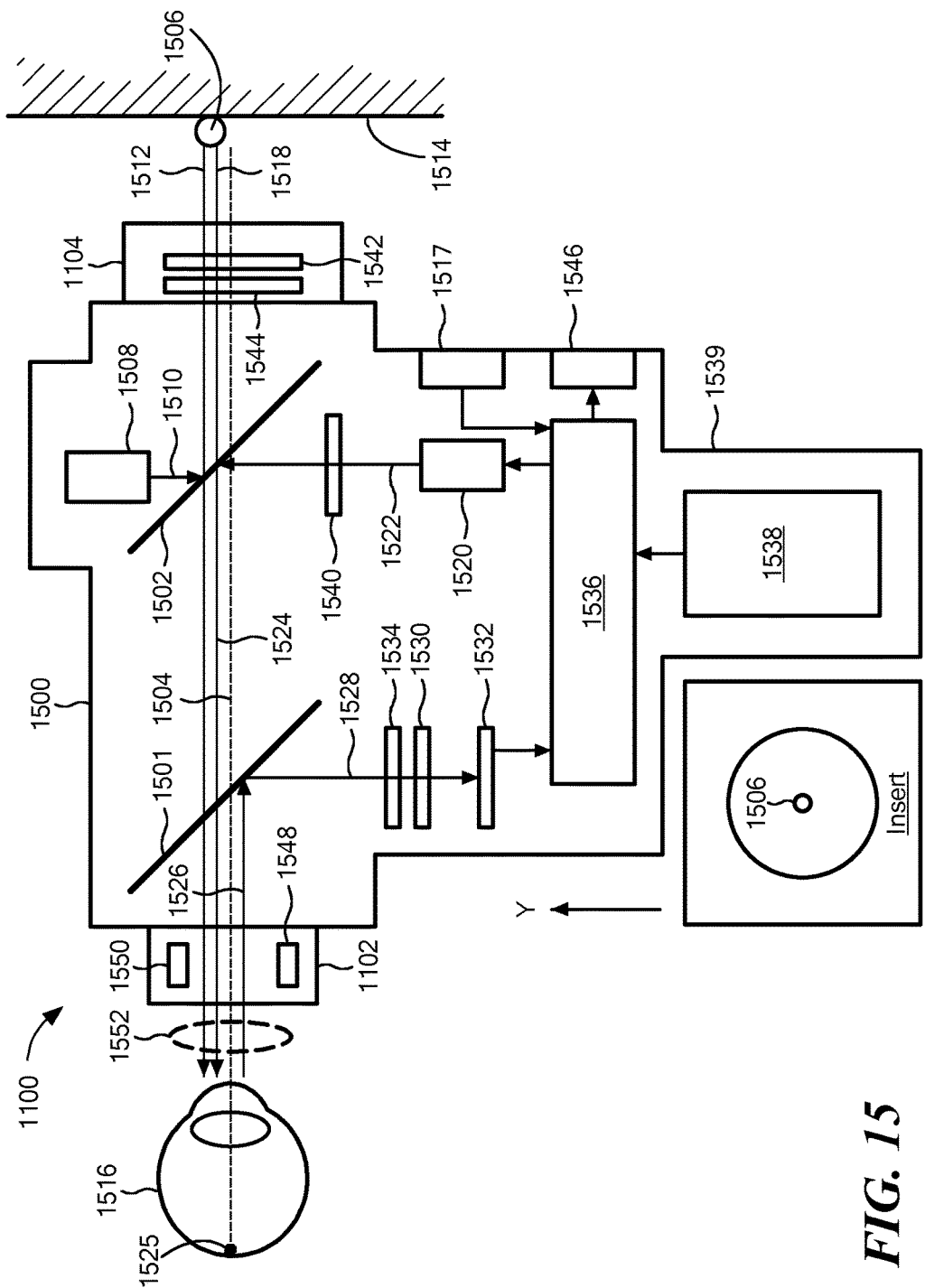
FIG. 15 is a schematic block diagram of the device of FIGS. 11-14, showing its internal components, according to an embodiment of the present invention.
Figures 1, 15:
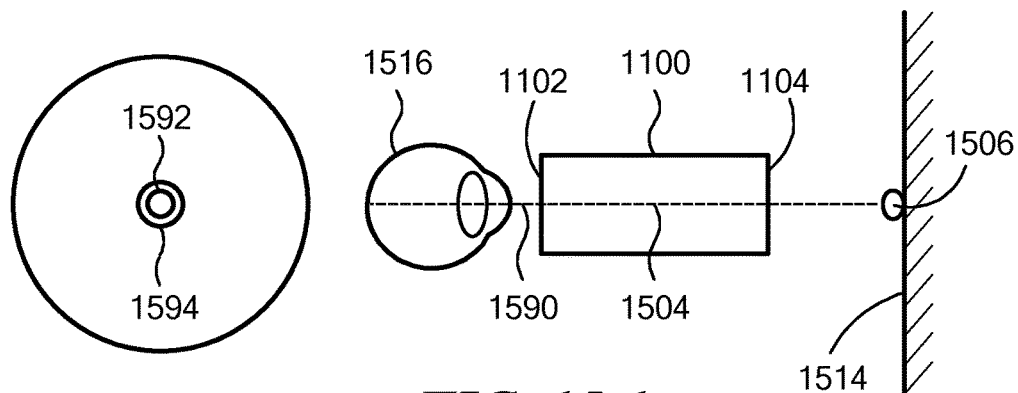
Figures 2, 15:
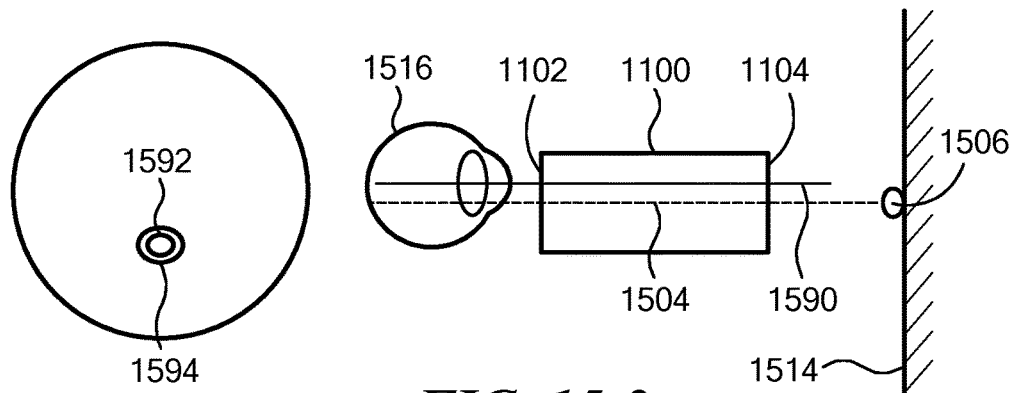
Figures 3, 15:
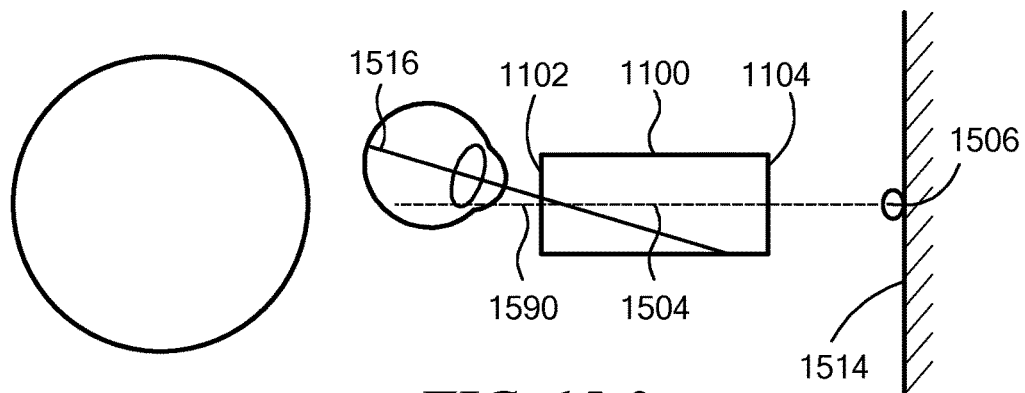

FIG. 15 is a schematic block diagram of the apparatus 1100 showing its internal components, within a body 1500. Two beamsplitters 1501 and 1502 are disposed along an optical axis 1504 between the eyepiece 1102 and the exit port 1104. The patient looking into the eyepiece 1102 along the optical axis 1504 can see an external object 1506 that is aligned with the optical axis 1504. A view, as seen by the patient, is shown in an insert of FIG. 15.

In one embodiment, a visible light source 1508, such as a laser diode or light emitting diode (LED), emits a beam of light 1510, which the beamsplitter 1502 reflects along the optical axis 1504 out the exit port 1104, as indicated by arrow 1512. The beam 1512 can be used to create a spot of light on a distant wall or other object 1514. In this description, the object 1506 is assumed to be the spot of light created on the wall 1514 by the beam 1512. The visible light source 1508 is fixed, relative to the body 1501 and the optical components within the apparatus 1100. Thus, the beam 1512 is always coincident with the optical axis 1504.

The distant wall 1514 should be at least 20 feet (6 meters) from the apparatus 1100, so when the patient looks at the spot 1506, the patient's eye 1516 is substantially unaccommodated. An ultrasonic or other range sensor 1517 may be used to measure the distance between the apparatus 1100 and the wall 1514. The apparatus 1100 may provide an audible, visual, haptic or other warning if the distance is inappropriate. A return beam 1518 from the spot 1506 enters the exit port 1104, passes through the two beamsplitters 1502 and 1501 along the optical axis 1504 and enters the patient's eye 1516 via the eyepiece 1102. This enables the patient to see the spot 1506. For clarity, the optical axis 1504 and the two beams 1512 and 1518 are shown spaced apart; however, the axis and the two beams are coincident.

In another embodiment, the target can be an arbitrary, but known, distance from the patients. For example, if the target is projected 10 feet (3 meters) from the instrument, the amount of accommodation necessary for the patient to focus on the target is calculated, and then a prescription is calculated that compensates for the accommodation.

The eyepiece 1102 may also be referred to as a proximal port, and the exit port 1104 may also be referred to as a distal port. The body 1500 forms a visual channel between the eyepiece 1102 and the exit port 1104. The beam 1512 may also be referred to as a target beam, the wall or other object 1514 may be referred to as a target and the spot 1506 may also be referred to as target indicia.

Optionally, the visual channel between the eyepiece 1102 and the exit port 1104 may have a conic shape, i.e., the shape may be a portion of a cone. In such an embodiment, the visual channel is configured such that a vertex of the conic shape is toward the eyepiece 1102 and a base of the conic shape toward the exit port 1104. A pinhole constrains where a user can position her eye and see through the pinhole. A pinhole does not, however, constrain the angle along which the user can through the pinhole. A tubular or conic visual channel does, however, constrain the view angle. Thus, a conic visual channel, with pinhole, which may be implemented as a small hole at or near the vertex of the cone, constrains both the position of the user's eye and the angle along which the eye sees.

Another light source, such as another laser diode, 1520 projects a beam of light 1522. The beam splitter 1502 reflects the beam 1522 toward the eyepiece 1102 along the optical axis 1504, as indicated by arrow 1524. The beam 1524 illuminates a spot 1525 on the back of the eye 1516, thereby essentially creating a virtual point light source within the eye 1516. This virtual light source 1525 corresponds to the spot 618 described above, with respect to FIG. 8. As discussed above, with respect to Hartmann-Shack wavefront aberrometry, return wavefronts travel along a beam 1526 from the eye 1516. The beamsplitter 1501 reflects the beam 1526, and resulting beam 1528 passes through a lenslet array 1530 and impinges on an optical sensor 1532. Optional optics 1534, such as a relay lens system to make the lenslet array 1530 optically conjugate with the patient's spectacle plane and a band-pass and/or neutral density filter, may be disposed in the path of beam 1528. For clarity, the optical axis 1504 and the two beams 1524 and 1526 are shown spaced apart; however, the axis and the two beams are generally coincident.

Although embodiments using Hartmann-Shack wavefront aberrometry using a lenslet array are described, other methods for wavefront sensing can be used. Other embodiments use pinhole arrays or arrays of sensors for defocus imaging. In some embodiments, time-of-flight cameras, interferometric techniques or partitioned aperture wavefront imaging systems are used. Partitioned aperture wavefront imaging systems are well known to those of skill in the art, as evidenced by information available at http://biomicroscopy.bu.edu/research/partioned-aperture-wavefront-imaging.

An analysis unit 1536 is electronically coupled to the optical sensor 1532. The analysis unit 1536 includes appropriate interface electronics, a processor, memory and associated circuits configured to analyze signals from the optical sensor 1532 to calculate x and y displacements of spots in a spot diagram from where they would be if the eye 1516 were normal. From this data, the analysis unit 1536 calculates a set of Zernike coefficients and calculates a corrective lens prescription. Additional details about these analyses and calculations are provided below.

An internal battery 1538 powers the analysis unit 1536, the two light sources 1508 and 1520, the optical sensor 1532 and other components of the apparatus 1100. A handle portion 1539 of the housing 1500 may house the battery 1538. All electronic components of the apparatus 1100 are powered by the battery 1538, and all calculations necessary to ascertain the prescription are performed by the analysis unit 1536. Thus, the apparatus 1100 is completely self-contained, i.e., all components, apart from the wall 1514 and the eye 1516, necessary to perform its functions are included within the housing 1500. The apparatus 1100 is small and lightweight enough to be held in place long enough to perform the described measurement by a typical patient using one hand.

In one embodiment of the apparatus 1100, the light source 1520 that creates the virtual light source 1525 within the eye 1516 is a near infrared (NIR) light source. The wavelength of the light source 1520 is selected such that the patient perceives a red dot, although the bulk of the energy of the beam 1504 is not within the spectrum visible to the patient. On the other hand, the visible light source 1508 is selected to have a perceptively different color, such as green, than the red perceived by the patient from the NIR light source 1520. The patient may be instructed to orient the apparatus 1100, relative to the patient's eye, so as to maximize the perceived brightness of the red dot.

Thus, as schematically illustrated in FIG. 15-1, if the patient's eye 1516 is properly aligned with the eyepiece 1102, such that the eye's center of vision 1590 is aligned with the optical axis 1504 of the apparatus 1100, the patient perceives two coincident dots 1592 and 1594, one red and the other green, as illustrated on the left side of FIG. 15-1, or a single dot that is both red and green. Thus, the patient can be instructed to reorient the apparatus 1100 until she perceives the two coincident dots or one dual-colored dot. The patient can then easily hold the apparatus 1100 in the proper alignment for the short time required to collect data for generating a prescription.

As schematically illustrated in FIG. 15-2, if the patient's eye 1516 is improperly aligned with the eyepiece 1102, such that the eye's center of vision 1590 is parallel to, but slightly displaced from, the optical axis 1504 of the apparatus 1100, the patient sees the dots 1592 and 1594 off-center within the field of view afforded by the eyepiece, as exemplified on the left side of FIG. 15-2. However, as schematically illustrated in FIG. 15-3, if the patient's eye 1516 is grossly misaligned, the patient does not see any dots within the field of view afforded by the eyepiece, as shown on the left side of FIG. 15-3.

Thus, the simple design of the apparatus 1100 enables easy alignment of a patient's eye with optics of the apparatus 1100, without a chin rest or other complex heavy mechanical alignment apparatus required by the prior art. Furthermore, the open view design of the apparatus 1100 encourages the patient not to accommodate, without any cycloplegic agents, fogging or virtual images.

In other embodiments, other wavelengths may be used by the two light sources 1508 and 1520. In some embodiments, visible wavelengths are used for both of the light sources 1508 and 1520. In some embodiments, identical or similar wavelengths are used by both of the light sources 1508 and 1520, but one or both of the light sources 1508 and 1520 blink, so the patient can distinguish between the two resulting dots. If both light sources 1508 and 1520 blink, they should alternate being on.

The apparatus 1100 may include additional optical elements, such as a diaphragm 1540 to define the beam 1522 and align it with the beamsplitter 1502. An adjustable iris diaphragm 1542 may be used to define the exit port 1104. In one embodiment, the diaphragm 1542 has a maximum diameter of about 7 mm, and the beamsplitter 1500 has a 4:1 ratio of reflectance to transmittance at the operational wavelength of the light source 1520. The light source 1520 may generate an approximately 3 mW beam of about 2 mm in diameter at a wavelength of about 850 nm. The beamsplitter 1502 may include a "hot mirror," which passes visible light entering the exit port 1104, within a range of about 375 nm to about 725 nm, so the patient can see the spot 1506 through the eyepiece 1102. Optionally, the components of the apparatus 1100 may be displaced along a Y axis, so as to offset the beams 1504 and 1527 by about 1-2 mm to reduce specular reflection from the eye 1516. This specular reflection constitutes noise to the optical sensor 1532.

The amount of optical power than can safely be delivered by the light source 1520 to the eye 1516 is limited. Ambient light that enters the apparatus 1100 and impinges on the optical sensor 1532 constitutes noise. Under high ambient light conditions, this noise may reach unacceptably high levels. In addition, the ambient light may overwhelm the light from light source 1520, thereby preventing the patient from seeing a spot from this light source. Optionally, to reduce the level of this noise and reduce the level of ambient light seen by the patient, a neutral density filter 1544 may be disposed along the light path between the exit port 1104 and the beam splitter 1502. The neutral density filter may be selected or adjusted to admit any appropriate amount of light, such as about 1%.

Figure 16:
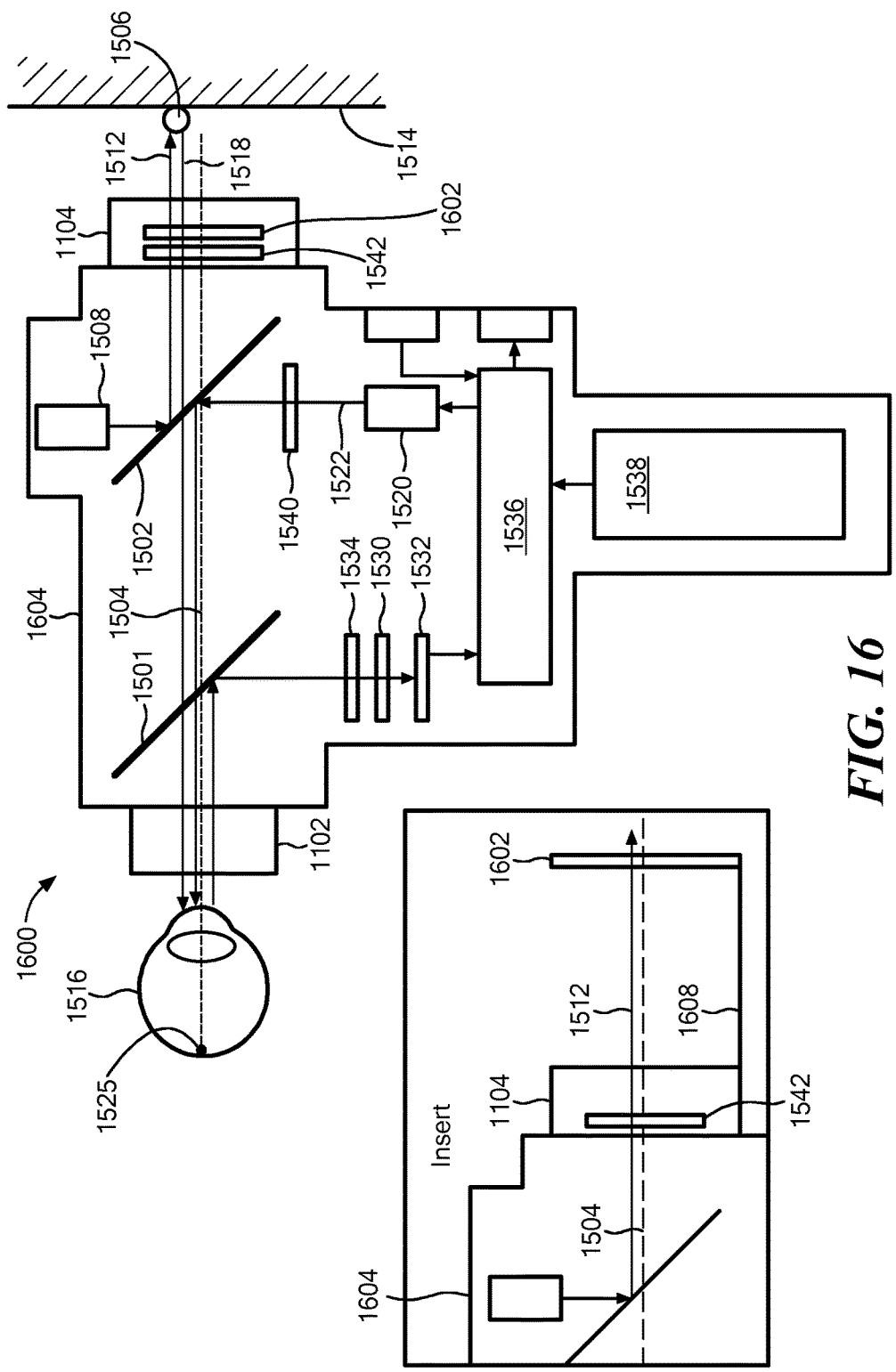
FIG. 16 is a schematic block diagram of the device of FIGS. 11-14, showing its internal components, according to another embodiment of the present invention.
Figure 17:
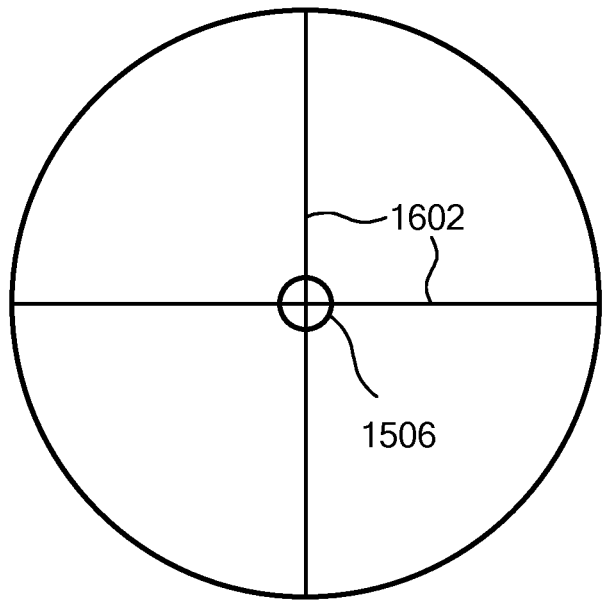
FIG. 17 illustrates a view through the device of FIG. 16, as seen by a patient using the device when the patient's eye is properly aligned with the device.
Figure 18:
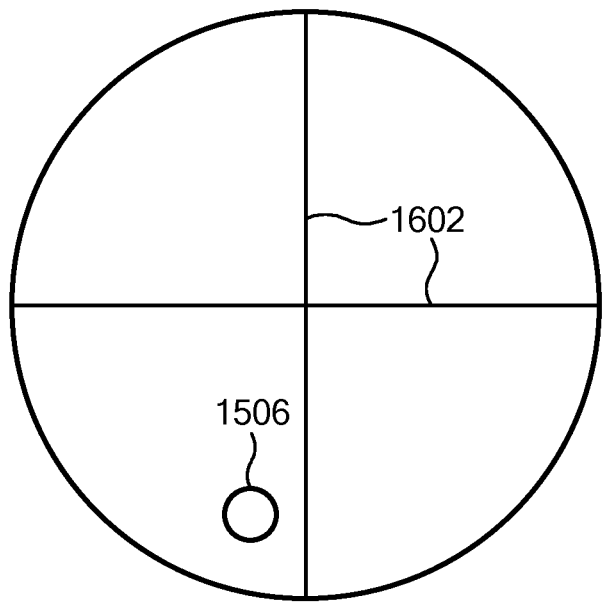
FIG. 18 illustrates a hypothetical view through the device of FIG. 16, as seen by a patient using the device when the patient's eye is not properly aligned with the device.

In another embodiment shown schematically in FIG. 16, an optical or ophthalmologic apparatus 1600 includes components as described above, with respect to FIG. 15, and further includes a cross-hair 1602 disposed along the optical path between the eyepiece 1102 and the exit port 1104, such that the center of the cross-hair 1602 coincides with the optical axis 1504. Thus, the cross-hair 1602 is visible in the field of view of the eye 1516, as shown in FIGS. 17 and 18. If the patient sights down the center of the optical path between the eyepiece 1102 and the exit port 1104, thereby aligning his eye 1516 with the optical axis 1504, the spot 1506 appears at the intersection of the cross-hair 1602, as shown in FIG. 17. However, if the patient does not properly align his eye 1516 with the optical axis 1504, the spot 1506 does not appear at the intersection of the cross-hair 1602, for example as shown in FIG. 18. The patient can be instructed to reorient the apparatus 1600 until he sees the spot 1506 at the center of the cross-hair 1602. In this embodiment, the light source 1520 need not generate a beam 1522 that is perceived at all by the patient.

The cross-hair 1602 should be disposed a distance away from the eye 1516, so as not to require the eye 1516 to accommodate and still have the cross-hair 1602 reasonably well focused. This may require the cross-hair 1602 to be held a distance from most of the housing 1604, such as by an outrigger 1608, as shown in the insert of FIG. 16.

Other aspects of the apparatus 1600 are similar to the apparatus 1100; however, some reference numerals are omitted from FIG. 16 in the interest of clarity.

Figure 19:
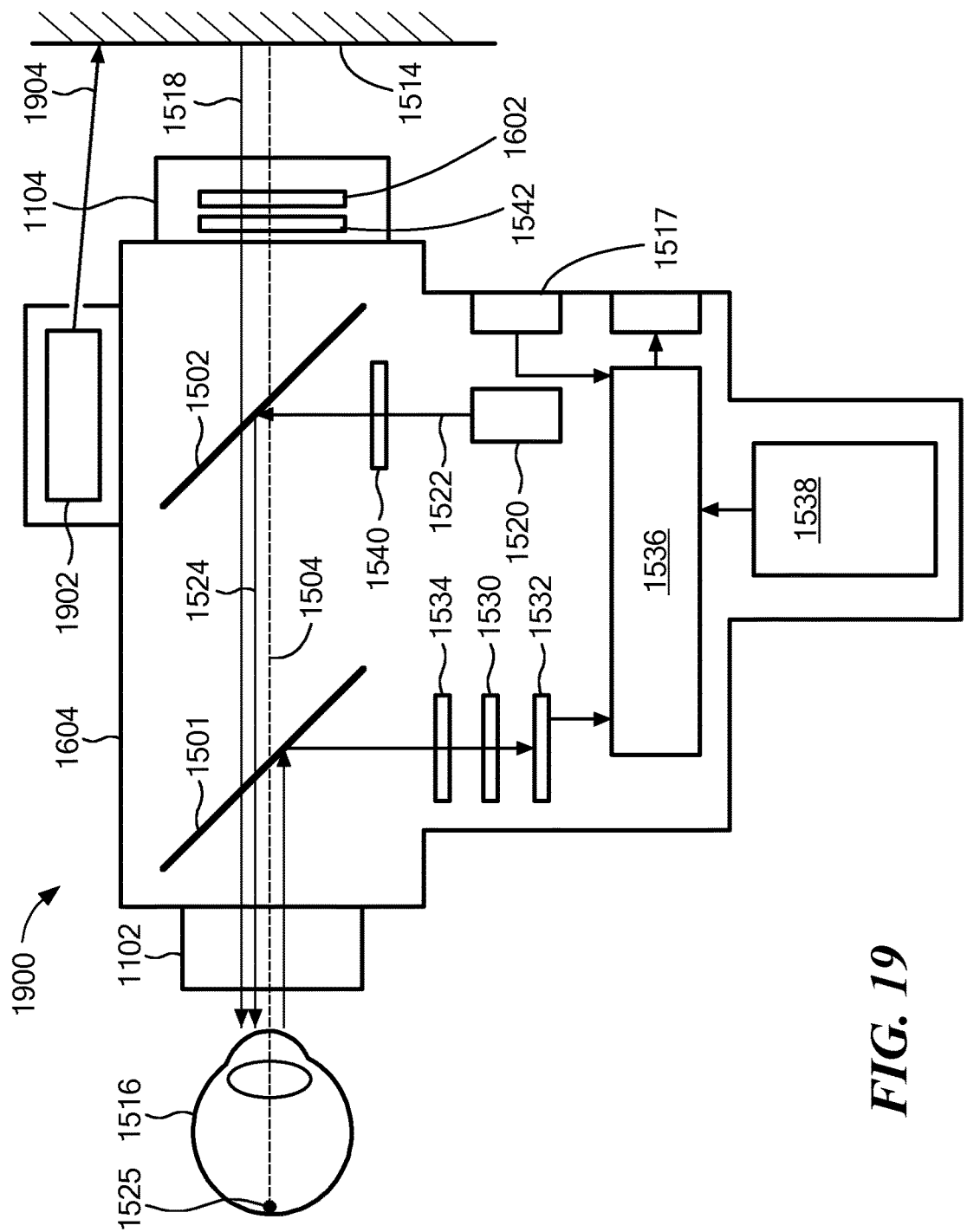
FIG. 19 is a schematic block diagram of the device of FIGS. 11-14, showing its internal components, according to yet another embodiment of the present invention.

In yet another embodiment shown schematically in FIG. 19, an optical or ophthalmologic apparatus 1900 includes components as described above, with respect to FIG. 15, except the visible light source 1902 projects a spot on the wall 1514, without the visible beam 1904 passing through the beamsplitter 1502. As shown schematically in FIG. 20, the beam 1904 is not parallel to the optical axis 1504. Thus, the beam 1904 intersects the optical axis 1504 at a distance 2000 from the apparatus 1900. An angle 2002 of the light source 1902, relative to the optical axis 1504, is selected such that the distance 2000 is at least 20 feet (6 meters). The ultrasonic or other range sensor 1517 or a simple tape measure may be used to selectively dispose the apparatus 1900 at a desired distance from the wall 1514.

Figure 20:
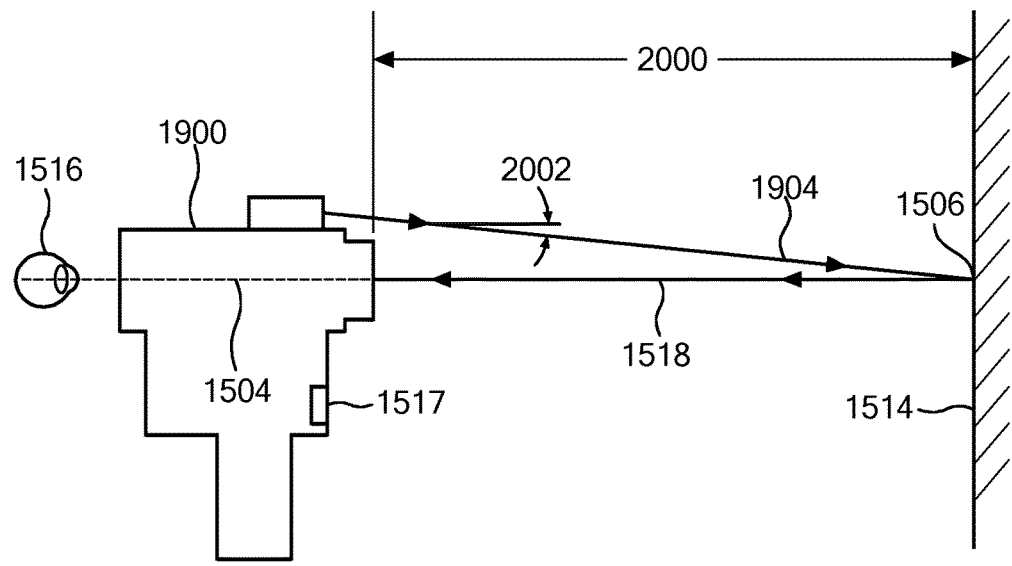
FIG. 20 is a schematic block diagram of the device of FIG. 19 in use.
Figure 21:
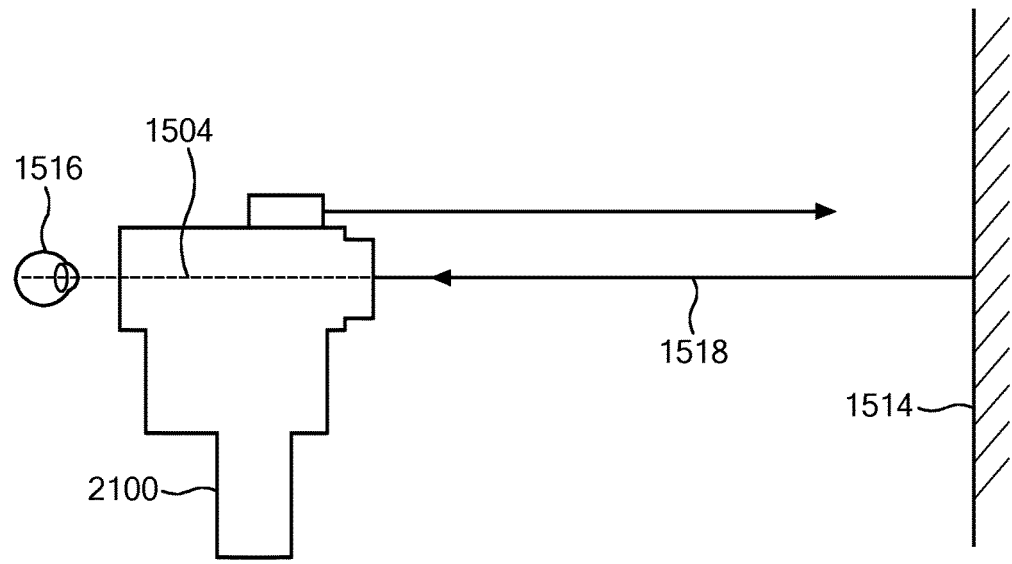
FIG. 21 is a schematic block diagram of an alternative embodiment of the device of FIGS. 19 and 20 in use.

In another embodiment shown schematically in FIG. 21, an apparatus 2100 is similar to the apparatus shown in FIGS. 19 and 20, except the visible light source 1902 is aligned parallel to, but spaced apart from, the optical axis 1504. If the distance between optical axes of the projected light source 1902 and the internal light source 1520 is sufficiently small, then when the patient aligns the device so that images of the two sources are coincident, the eye is sufficiently aligned for an accurate wavefront measurement. In some embodiments, the axis of the visible light source 1902 or 1508 (FIG. 15) is offset about 20 mm from the axis of the internal light source 1520. However, with a target distance of about 20 feet (6 meters), this imperfect alignment does not substantially affect operation of the instrument or prescription or measurements taken by the instrument. Thus, in embodiments in which the visible light source 1902 or 1508, internal light source 1520 and/or optical axis 1504 misalignment is less than about 0.5%, we refer to these components as being "substantially aligned."

Figure 55:
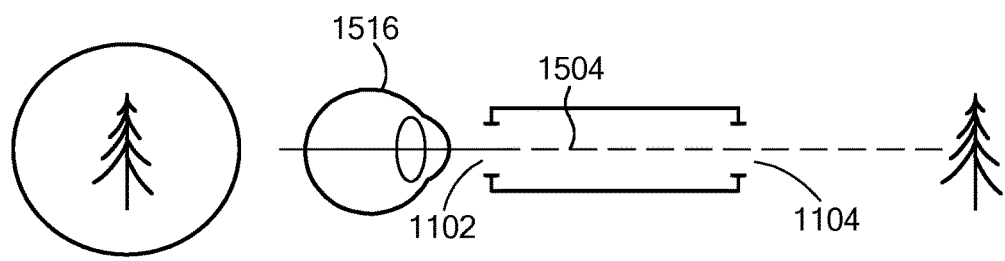
FIG. 55 is a schematic diagram illustrating an eye properly aligned with a device, as well as a view as seen by the eye through the device, according to another embodiment of the present invention.
Figure 56:
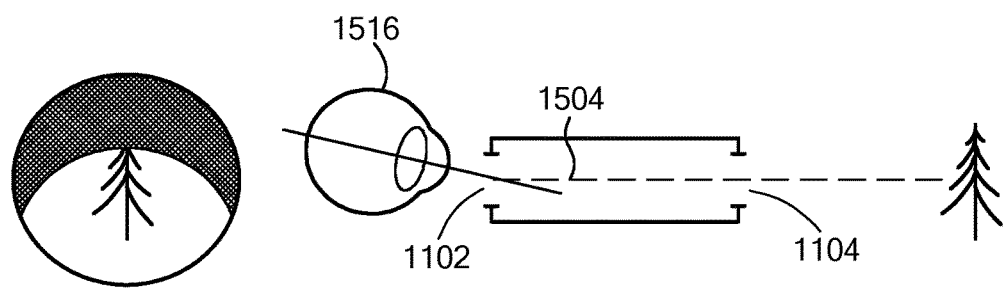
FIG. 56 is a schematic diagram illustrating an eye slightly misaligned with the device of FIG. 55, as well as a hypothetical view as seen by the eye through the device, according to an embodiment of the present invention.
Figure 57:
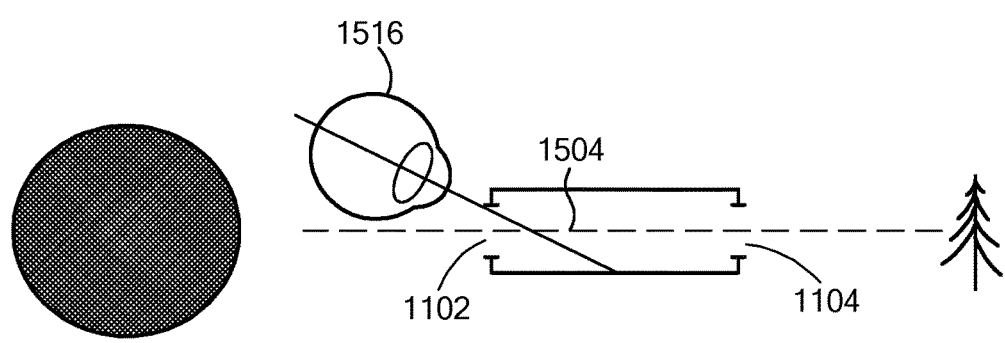
FIG. 57 is a schematic diagram illustrating an eye grossly misaligned with the device of FIG. 55, as well as a view as seen by the eye through the device, according to an embodiment of the present invention.

In another embodiment schematically illustrated in FIGS. 55-57, the apparatus does not include a visible light source, such as light source 1508 or 1902 (FIGS. 15 and 19). Instead, the patient is instructed to look into the apparatus and maintain her gaze in the center of the field of view provided by the eyepiece 1102 and exit port 1104 of the apparatus. In FIG. 55, the eye 1516 is properly aligned with the optical axis 1504 of the device. A hypothetical view, as seen by the eye 1516, is shown on the left in FIG. 55. In FIG. 56, the eye 1516 is slightly misaligned with the optical axis 1504 of the device. A hypothetical view, as seen by the eye 1516, is shown on the left in FIG. 56. In FIG. 57, the eye 1516 is grossly misaligned with the optical axis 1504 of the device. A hypothetical view, as seen by the eye 1516, is shown on the left in FIG. 57.

In such embodiments, it may be advantageous to provide a relatively small field of view, such as by closing the iris diaphragm 1542 (FIG. 15) smaller than in the embodiments described above with respect to FIGS. 15, 16 and 19. Processing of the spot diagram generated from the patient's eye 1516 may be used to ascertain whether the patient's eye 1516 is properly aligned with the optical axis 1504 and, if not, generate a feedback instructional signal to the patient, as described in more detail below.

Binocular Aberrometer

Figure 22:
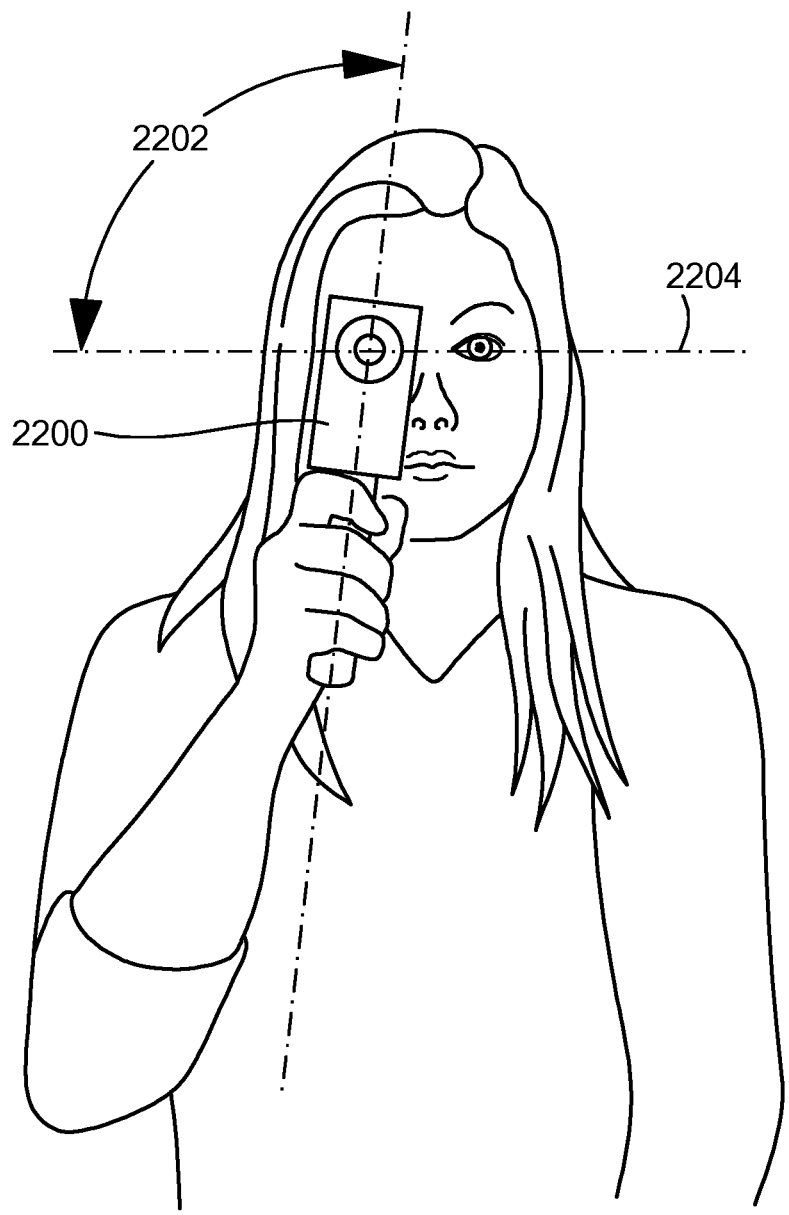
FIG. 22 is a front view of an embodiment of the present invention in use by a patient, in which the device is tilted, with respect to the patient's interpupillary axis.

FIG. 22 illustrates a possible source of error in measurements made by the devices described thus far. If a patient holds the apparatus 2200 at an angle 2202 other than perpendicular to the patient's interpupillary axis 2204, the cylindrical axis components of a prescription generated by the apparatus 2200 may be incorrect. One solution to this problem involves including an accelerometer (not shown) in the apparatus 2200 to detect if the apparatus 2200 is oriented other than vertical and, if so, warn the user. Another solution is to use the measured angle from the accelerator to offset the measured cylindrical axis by the appropriate amount. However, these approaches have limitations. For example, the patient may not be positioned with her head vertical, thereby making a vertical orientation of the apparatus an incorrect orientation.

Figure 23:
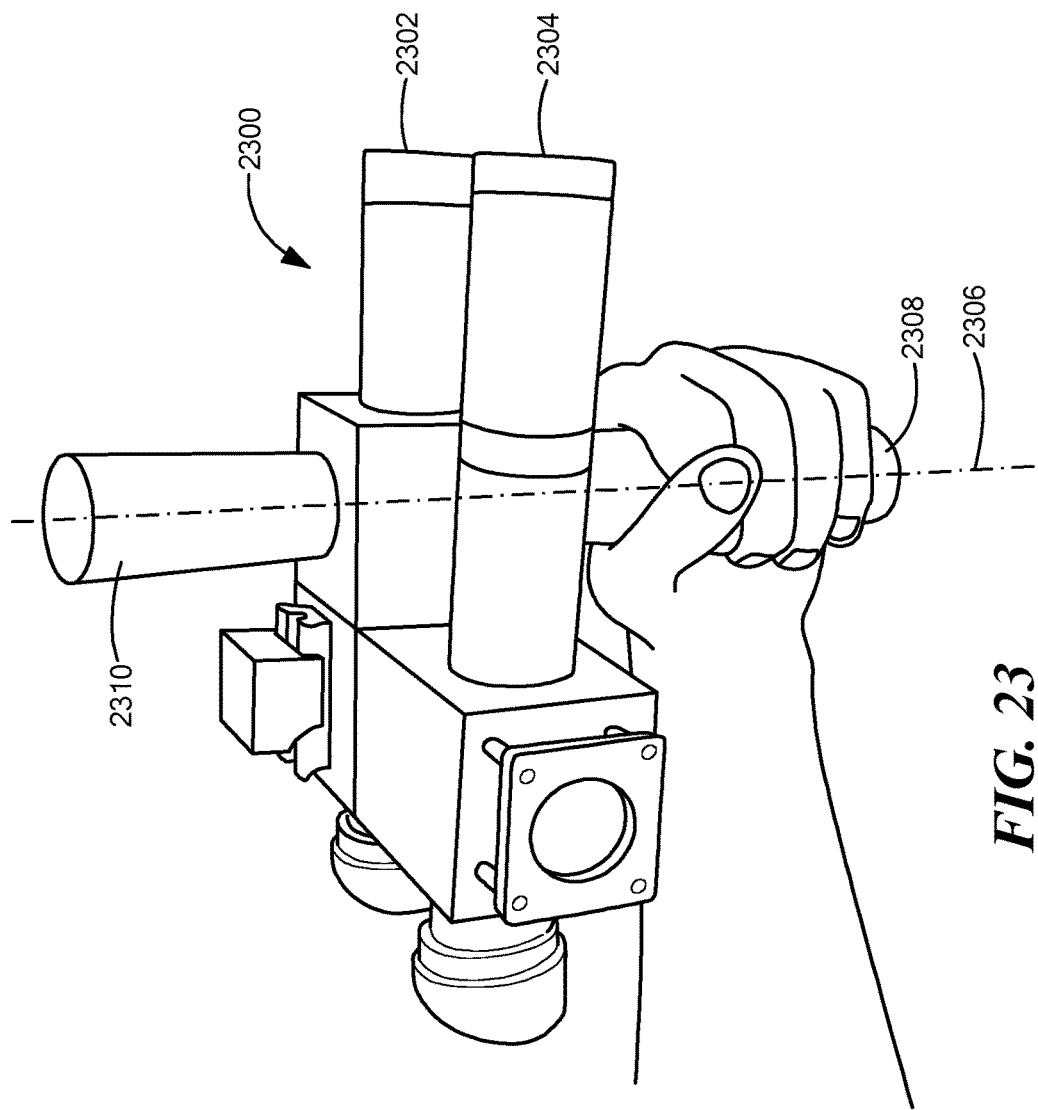
FIG. 23 illustrates a binocular lightweight portable hand-held automatic device that includes a Hartmann-Shack wavefront aberrometer, according to an embodiment of the present invention.
Figures 1, 23:
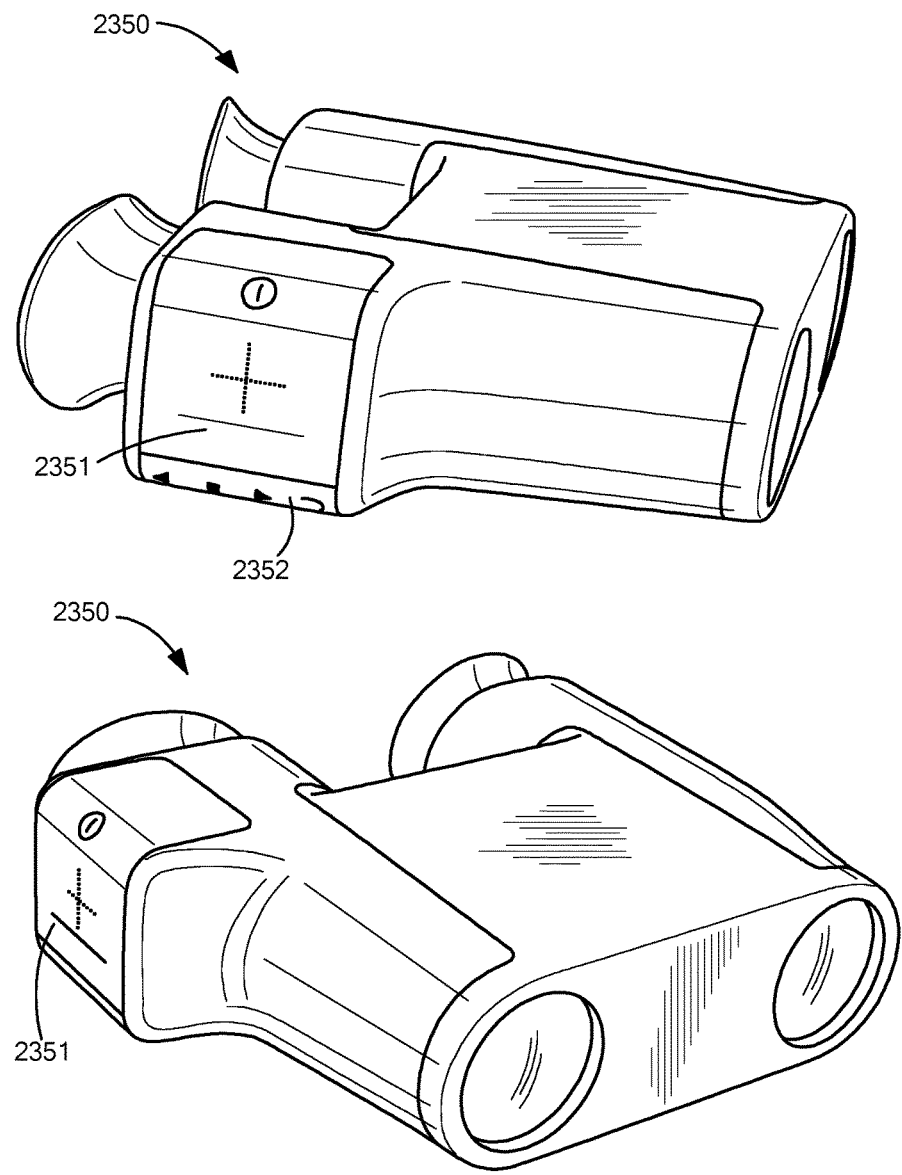

To overcome this problem, optionally, any embodiment described herein may be configured as a binocular instrument, as exemplified by an optical or ophthalmologic apparatus 2300 illustrated in FIG. 23. An alternative binocular instrument 2350 is illustrated in FIG. 23-1. The binocular instrument 2300 may be held by a patient using two hands, thereby providing more stability than one hand holding a monocular instrument, at least in part because using two hands reduces the number of degrees of freedom of movement of the instrument 2300. Because the binocular instrument 2300 is more likely to be held by the patient so the instrument axis between the two eyepieces is parallel to the patient's intraocular axis, prescriptions to correct astigmatism are more likely to include accurate angles of the cylinder axis.

In the binocular instrument 2300, one side 2302 of the instrument 2300 includes the components described above, such as with respect to FIG. 15, and the other side 2304 of the instrument is essentially merely a hollow tube. A patient is very likely to hold a binocular instrument to her face in a manner such that a vertical axis 2306 of the instrument is perpendicular to the patient's interpupillary axis, even if the patient leans her head to one side.

The side 2302 of the binocular instrument 2300 that includes the aberrometer may include a neutral density filter 1544 (FIG. 15) to reduce the amount of ambient light admitted into the instrument, as discussed above. Even without a neutral density filter 1544 in the "business" side 2302 of the binocular instrument 2300, the beamsplitter 1501, band pass filter 1534, etc. attenuate light. Therefore, the other side 2304 of the binocular instrument 2300 should include a neutral density filter, so both eyes receive approximately equal amounts of light.

Once the instrument 2300 has been used to measure one eye, the instrument 2300 can be turned up-side-down to measure the other eye. The binocular instrument 2300 shown in FIG. 23 includes two handles 2308 and 2310, making the instrument equally easy to hold right-side-up and up-side-down. Alternatively, both sides 2302 and 2304 may include most of the components described above, such as with respect to FIG. 15. Such an embodiment can measure both eyes substantially simultaneously, without requiring the device to be turned up-side-down. Alternatively, additional beamsplitters can be incorporated into a secondary channel to route the measuring light and wavefront sensor field of view to simultaneously image spot diagrams from both eyes.

Figure 24:
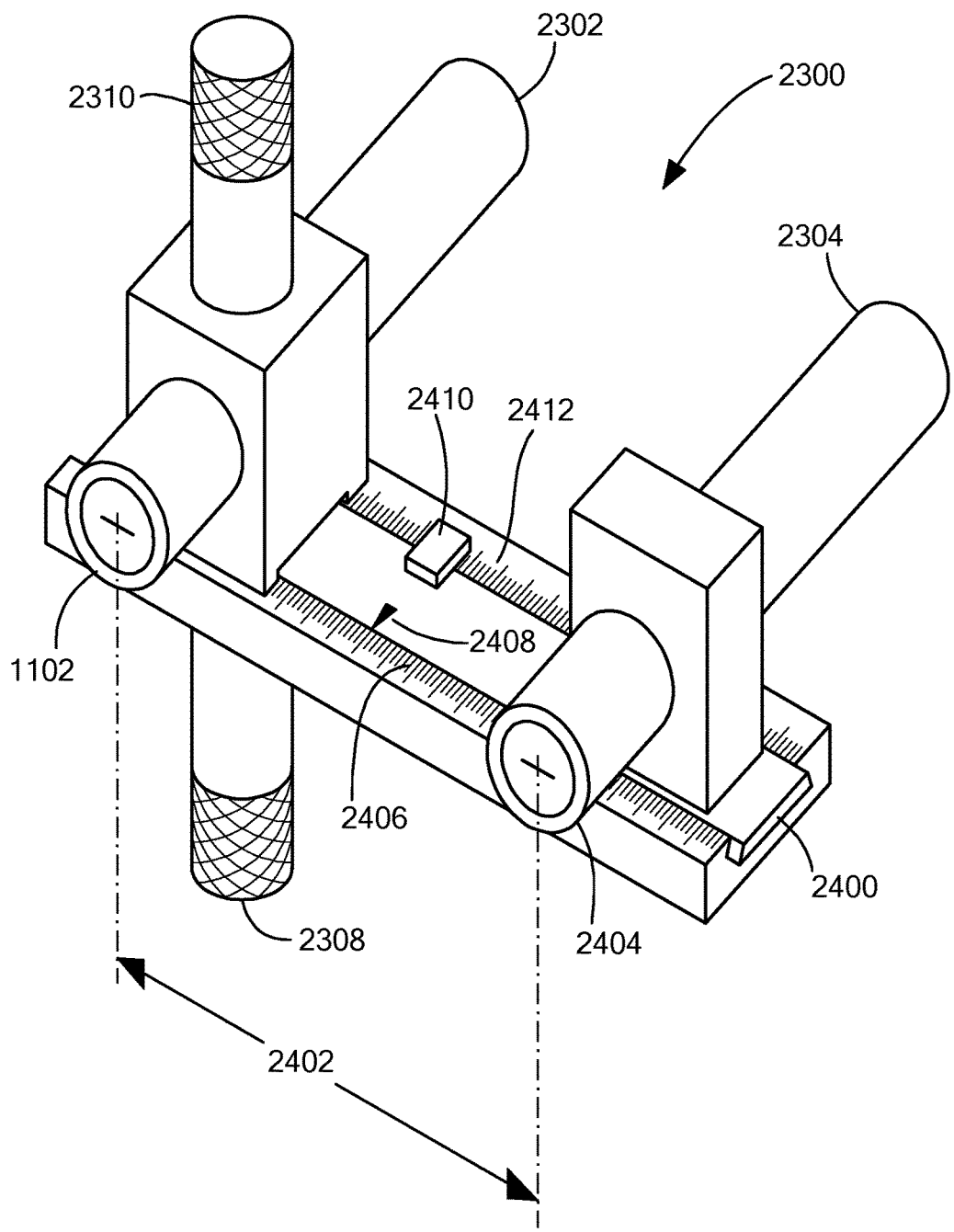
FIG. 24 schematically illustrates a dovetail slide of the device of FIG. 23 for adjusting spacing between two eyepieces of the device, according to an embodiment of the present invention.

As shown schematically in FIG. 24, the two portions 2302 and 2304 of the binocular instrument 2300 may be adjustably attached to each other by a dovetail or other sliding rail 2400, enabling distance 2402 between centers of the two eyepieces 1102 and 2404 to be adjusted to match a patient's interpupillary distance. Once the separation between the two eyepieces 1102 and 2404 has been adjusted so the eyecups comfortably fit contours of the patient's face, the interocular distance can be read from a scale 2406 using a pointer 2408. Optionally or alternatively, a linear encoder 2410 and indicia 2412 are used to electronically measure the distance 2402. The distance 2402 can be used as a parameter for constructing a pair of eyeglasses for the patient.

Figure 25:
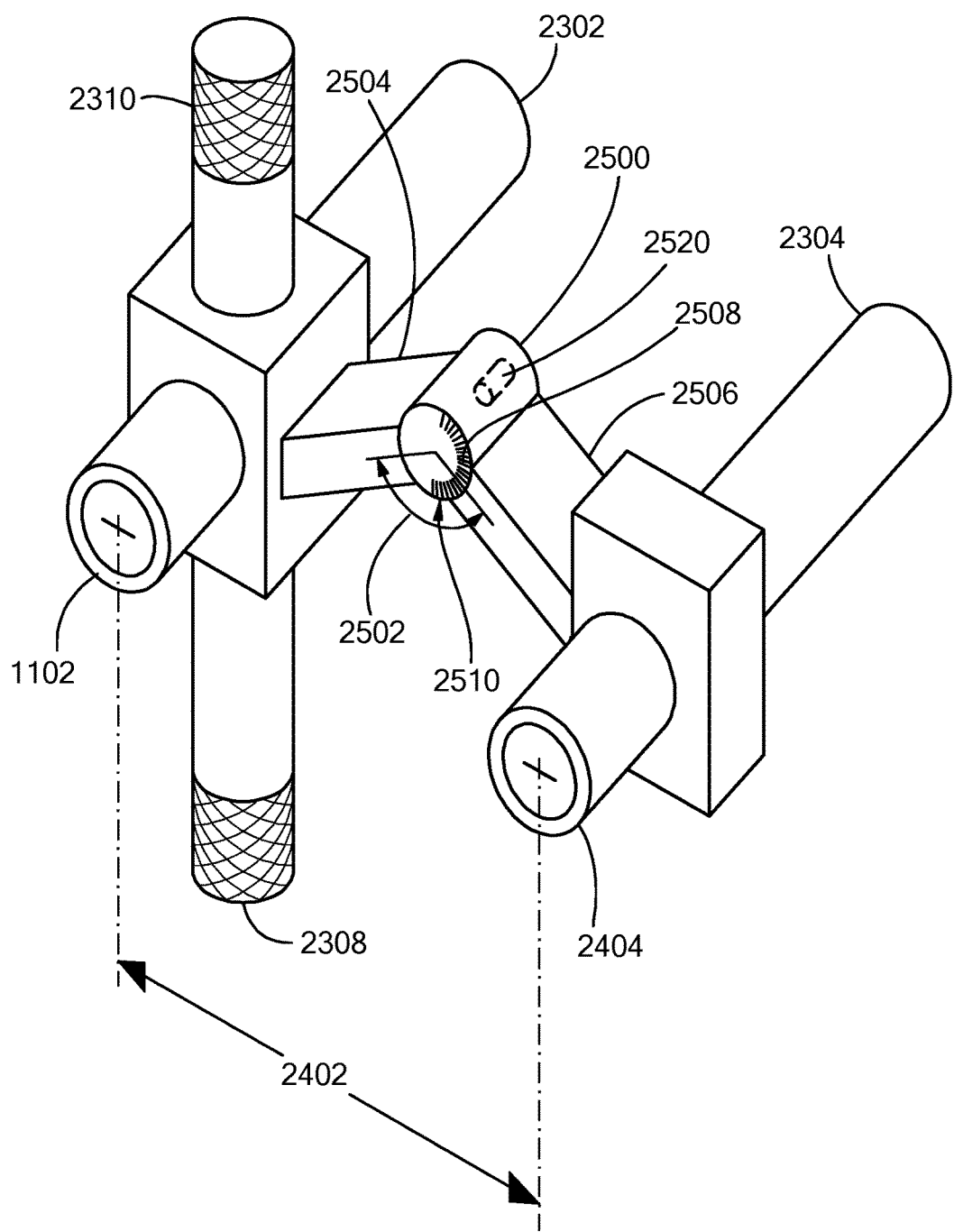
FIG. 25 schematically illustrates a pivot joint of the device of FIG. 23 for adjusting the spacing between two eyepieces of the device, according to another embodiment of the present invention.

Rather than a sliding rail 2400, a worm gear or other suitable linear, angular or other adjustable link may be used. For example, as shown schematically in FIG. 25, the two portions 2302 and 2304 may be adjustably attached to each other by a pivot joint 2500. As an angle 2502 defined by two connecting member 2504 and 2506 changes, the distance 2402 between the centers of the two eyepieces 1102 and 2404 changes. A scale 2508 and pointer 2510 may be calibrated to indicate the distance 2402 or the angle 2502. Of course, the distance 2402 can be calculated from the angle 2502 and known geometry of the instrument. Optionally or alternatively, an angular encoder 2510 (shown in dashed line) is included in the pivot joint 2500.

Analysis Unit

Figure 26:
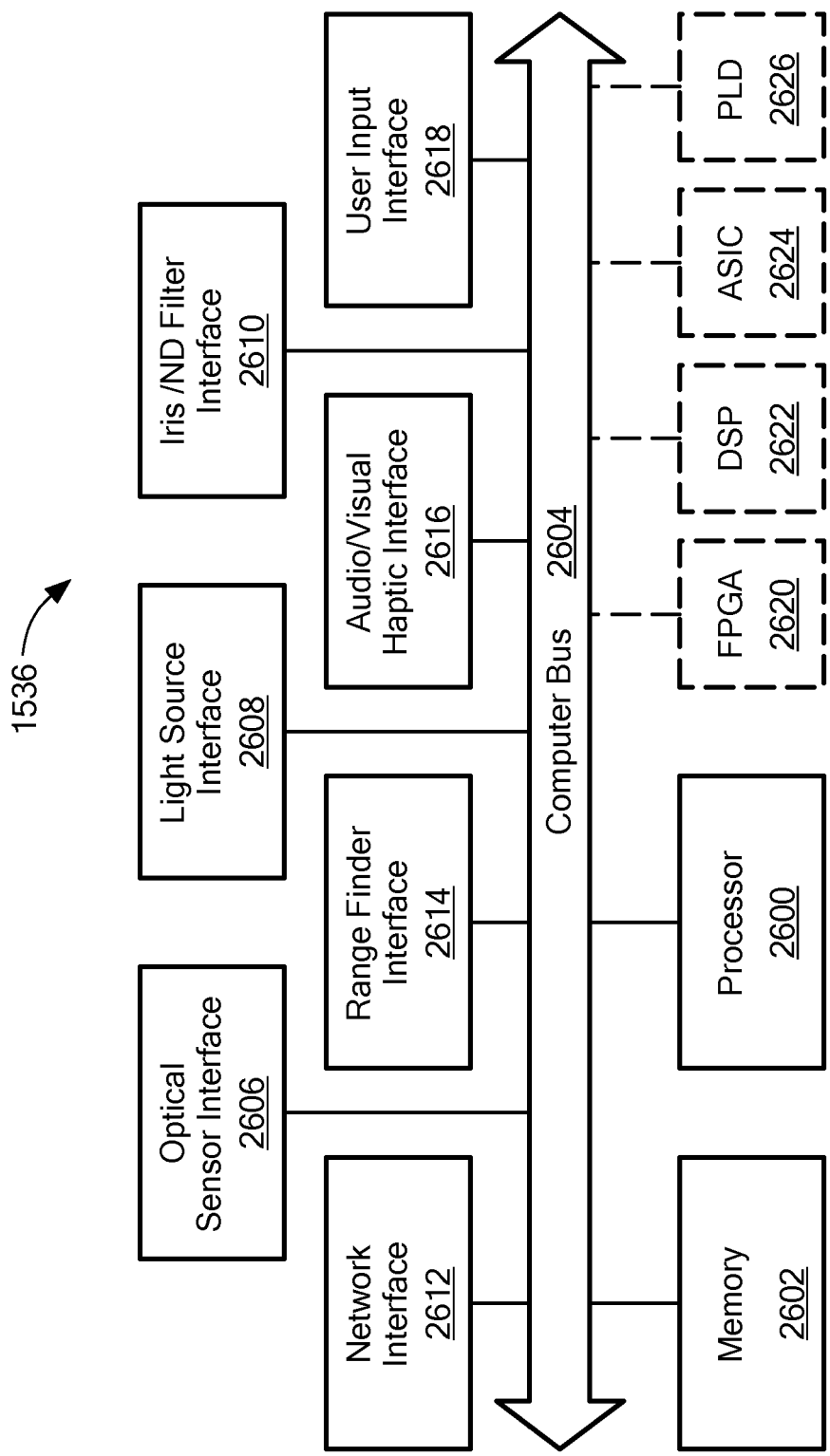
FIG. 26 is a schematic block diagram of hardware components of an analysis unit that may be included in, for example, the device of FIG. 15, according to an embodiment of the present invention.

As noted with respect to FIG. 15, the optical or ophthalmologic apparatus 1100 includes an analysis unit 1536 configured to analyze signals from the optical sensor 1532 to calculate x and y displacements of spots in a spot diagram, calculate a set of Zernike coefficients from the displacements and calculate a corrective lens prescription from the coefficients. The analysis unit 1536 also controls operation of various components of the apparatus 1100. FIG. 26 is a schematic block diagram of the analysis unit 1536. Similar analysis units may be used in other embodiments of the present invention.

The analysis unit 1536 includes a processor 2600 coupled to a memory 2602 via a computer bus 2604. The processor 2600 executes instructions stored in the memory 2602. In so doing, the processor 2600 also fetches and stores data from and to the memory 2602.

Also connected to the computer bus 2604 are: an optical sensor interface 2606, a light source interface 2608, an iris/neutral density filter interface 2610, a computer network interface 2612, a range finder interface 2614, an audio/visual/haptic user interface 2616 and a user input interface 2618. These interfaces 2606-2618 are controlled by the processor 2600 via the computer bus 2604, enabling the processor to send and/or receive data to and/or from respective components coupled to the interfaces 2606-2618, as well as control their operations.

The optical sensor interface 2606 is coupled to the optical sensor 1532 (FIG. 15) to receive data from the pixels, quadrant sectors or other elements of the optical sensor 1532. As noted, in some embodiments, the optical sensor 1532 is pixelated. In some embodiments, the optical sensor 1532 includes a rectangular array of quadrant sensors. In either case, the optical sensor 1532 provides data indicating intensity of illumination impinging on portions of the optical sensor 1532. The processor 2600 uses this information to calculate locations of centroids of spots of a spot diagram and to calculate displacements of the centroids from locations where a perfect eye would cause the centroids to impinge on the optical sensor 1532. Some optical or ophthalmologic apparatus embodiments, described below, include other or additional optical sensors, which are also coupled to the optical sensor interface 2606.

The light source interface 2608 is coupled to the visible light source 1508 (FIG. 15) and to the light source 1520 to control their operations, such as turning the light sources on and off and, in some embodiments, controlling intensities of light emitted by the light sources 1508 and 1520. In some embodiments, described below, one or both of the light sources 1508 and 1520 include a respective array of individual light sources. In these cases, the light source interface 2608 may enable the processor to control each of the individual light sources separately.

The iris/neutral density filter interface 2610 is coupled to the adjustable iris diaphragm 1542 and/or the neutral density filter 1544 (FIG. 15) to enable the processor 2600 to control their operations. For example, the processor 2600 may send signals, via the interface 2610, to command the iris diaphragm 1542 to open or close to a specified size. Similarly, if the neutral density filter 1544 is adjustable, the processor 2600 may send signals, via the interface 2610, to command the neutral density filter 1544 to admit a specified portion of light.

The network interface 2612 includes a wired or wireless interface, such as a universal serial bus (USB) interface, a wired Ethernet interface, a Bluetooth interface, a wireless infrared (IR) interface, a wireless local area network (WLAN) interface or a wireless cellular data interface, by which the processor 2600 may communicate with another suitably equipped external device, such as a printer, a personal computer a cell phone or smartphone, an automated lens grinder or an eyeglass order processing system. In some embodiments, the processor 2600 sends a prescription it has calculated to the external device, either directly or via a network, such as a local area network or a cellular carrier network. In some embodiments, the processor receives patient data, program updates, configuration information, etc. from an external device via the network interface 2612. Although embodiments have been described in which all Zernike and prescription calculations are performed within the apparatus, in other embodiments the processor sends raw data from the optical sensor 1532, calculated spot diagram information, Zernike coefficients or other intermediate information to the external device, and the external device calculates the prescription.

The range finder interface 2614 is coupled to any range sensor 1517 in the ophthalmologic apparatus.

The audio/visual/haptic interface 2616 is coupled to any audio, visual and/or haptic output devices in the ophthalmologic apparatus. For example, as noted, the apparatus 1100 may provide an audible, visual, haptic or other warning if the distance 2000 (FIG. 20) between the apparatus 1900 and the wall 1514 is inappropriate. Alternatively, as indicated below, this interface 2616 can be used to provide feedback about the alignment between the patient's eye and the optical axis of the device. Suitable audio devices include beepers, loudspeakers, piezoelectric devices, etc. Suitable visual devices include lights, liquid crystal display (LCD) screens, etc. Suitable haptic devices include vibrators, refreshable braille displays, etc.

The user input interface 2618 is coupled to any user input devices in the ophthalmologic apparatus. Such input devices may, for example, be used to initiate a measurement of a patient's eye. Suitable user input devices include buttons, keys, triggers, touchscreens, tactile sensors, etc. An exemplary user interface 2352 is shown in FIG. 23-1.

One or more of the interfaces 2606-2618, the processor 2600, the memory 2602 and the computer bus 2604, or any portion thereof, may be replaced or augmented by a suitably programmed device such as a programmable logic device (PLD) 2626, field-programmable gate array (FPGA) 2620, digital signal processor (DSP) 2622, application-specific integrated circuit (ASIC) 2624, discrete logic or suitable circuit. The components connected to the interfaces 2606-2618, the interfaces themselves, the processor 2600, the memory 2602 and computer bus 2604, together with the optical and mechanical elements described herein, collectively perform the functions described herein, under control of the processor 2600 and/or the PLD 2626, FPGA 2620, DSP 2622 and/or ASIC 2624.

Figure 27:
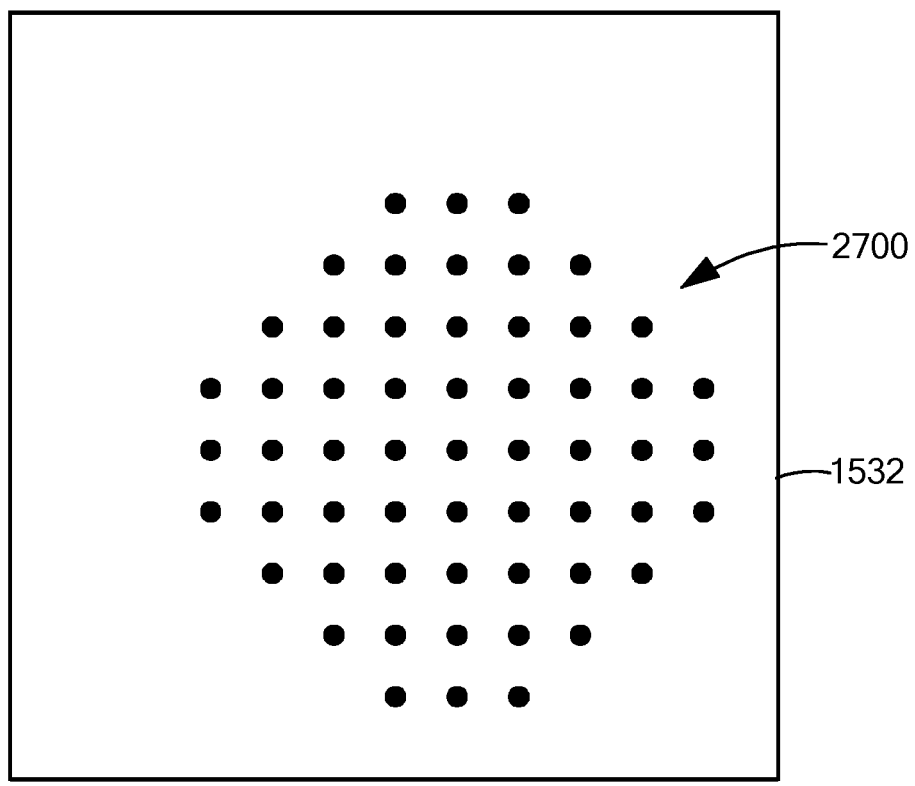
FIG. 27 is a schematic diagram of a hypothetical spot diagram not centered on an optical sensor of the device of FIGS. 11-15.

Automatically Determine Whether Eye is Aligned with Optical Axis and Provide Feedback to Patient As noted with respect to FIG. 7, an array of spots (a spot diagram 710) is projected on the optical sensor 610. If the eye 1516 is aligned with the optical axis 1504 of the device 1100 as shown in FIG. 15, the spot diagram is centered on the optical sensor 1532. However, as schematically exemplified in FIG. 27, if the eye 1516 is slightly misaligned with the optical axis 1504, the spot diagram 2700 is not centered on the optical sensor 1532. It should be noted that, even if the eyecup remains firmly pressed against a patient's face and the device 1100 does not move relative to the patient's head, the patient's eye can move within its eye socket and, therefore, become unaligned with the optical axis 1504.

Various approaches are available for automatically detecting when the patient has not aligned her eye 1516 with the optical axis 1504 and for providing feedback to the patient that notifies the patient of the misalignment. In some embodiments, the feedback indicates to the patient an extent and/or direction of the misalignment to provide guidance for self-correction. Several of these approaches will now be described.

Figure 28:
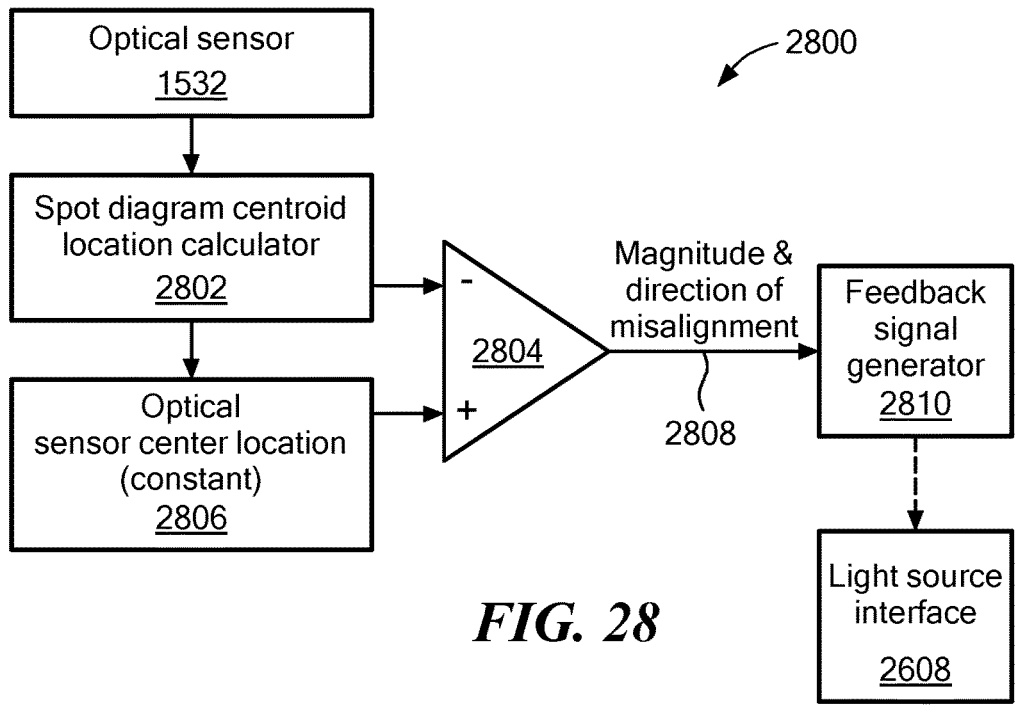
FIG. 28 is a schematic block diagram of an alignment feedback module, according to several embodiments of the present invention.

FIG. 28 is a schematic block diagram of an alignment feedback module 2800, according to several embodiments of the present invention. As used herein, the term "module" refers to one or more interconnected hardware components, one or more interconnected software components or a combination thereof. Thus, the alignment feedback module 2800 may be implemented by any of the components discussed above, with respect to FIG. 26.

In FIG. 9, it can be seen that all the spots of the spot diagram 810 are generally not of equal intensity. On the sensor 610, intensity of each spot is schematically indicated by the diameter of the spot. In general, spot intensity decreases with radial distance from the center of the spot diagram 810. Spot intensity distribution within the spot diagram is represented by a three-dimensional surface graph 920.

Returning to FIG. 28, a spot diagram centroid and size calculator 2802 is coupled to the optical sensor 1532 to receive signals therefrom, such as the intensity of light detected by each pixel or each quadrant. The spot diagram centroid and size calculator 2802 calculates size and location of the centroid of the entire spot diagram, such as its x and y or polar coordinates and the spot diagram diameter, on the optical sensor 1532. The spot diagram centroid calculator 2802 may use any appropriate algorithm or method for determining the centroid and size. Many such algorithms and methods are well known. In some embodiments, a weighted sum of the coordinates of the illuminated pixels is calculated, where each pixel's coordinates are weighted by the illumination level detected by the pixel. This information can be also used to determine the size of the spot diagram, e.g., the diameter of the spot diagram.

Figure 29:
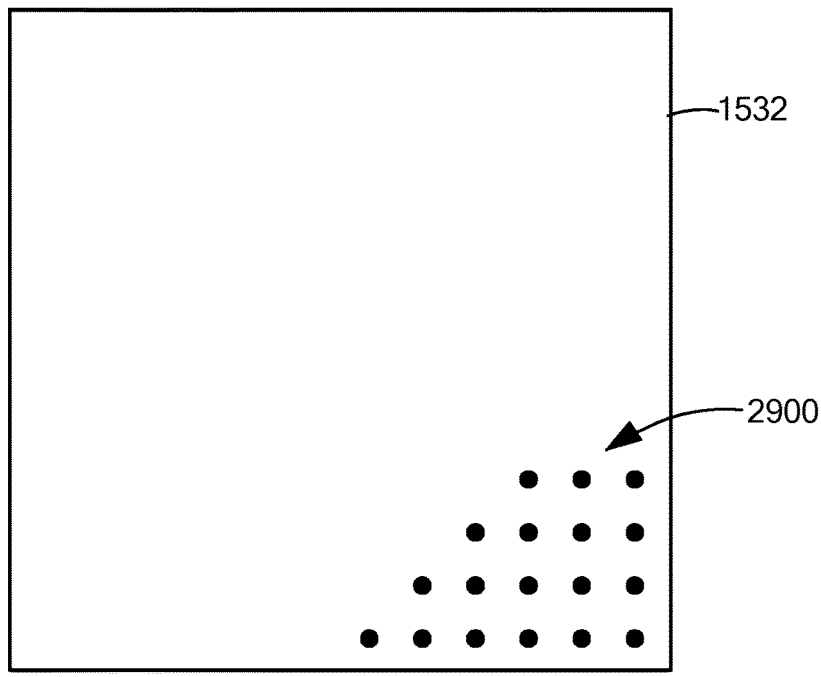
FIG. 29 is a schematic diagram of a hypothetical spot diagram that falls only partially on the optical sensor of the device of FIGS. 11-15.

Even if only a portion 2900 of the spots of a spot diagram fall on the optical sensor 1532, such that the true centroid of the spot diagram falls completely off the optical sensor 1532, as schematically exemplified in FIG. 29, the spot diagram centroid calculator 2802 may use the portion 2900 of the spots to calculate a location within the spots 2900 and provide this location as the centroid of the spot diagram. Furthermore, the shape of the portion of the spot diagram falling on the optical sensor 1532 can be also used to estimate the size of the spot diagram. The curvature of the portion of the spot diagram falling on the optical sensor 1532 may be used to estimate the diameter of the spot diagram. Similarly, the curvature of the portion of the spot diagram falling on the optical sensor 1532 may be used to estimate the true center of the spot diagram, even if the center is not within the optical sensor 1532. Optionally, the spot diagram centroid calculator 2802 may generate an additional signal to indicate the true centroid of the spot diagram is off the optical sensor 1532.

A difference calculator 2804 calculates a difference between the location of the centroid of the spot diagram and the center location 2806 of the optical sensor 1532. An output of the difference calculator 2804 represents a magnitude and direction 2808 of the displacement of the centroid of the spot diagram 2700 (FIG. 27) from the center of the optical sensor 1532. This magnitude and difference 2808 is fed to a feedback signal generator 2810.

The feedback signal generator 2810 generates an audio, visual, haptic and/or other output to the patient and/or an optional operator. Some embodiments include a loudspeaker, as exemplified by a loudspeaker 1546 (FIG. 15), and the feedback signal generator 2810 is coupled to the loudspeaker 1546. In some embodiments, the feedback signal generator 2810 generates audio signals, via the loudspeaker 1546, to indicate to the patient an extent of misalignment and/or a direction of the misalignment. In some such embodiments, a pitch or volume of a sound or a frequency of ticks (somewhat like a sound emitted by a Geiger counter) may represent how closely the eye is aligned to the optical axis. In some embodiments, a particular sound, such as a beep, is played when or whenever the eye is properly aligned. The feedback signal generator 2810 may include a speech synthesizer to generate synthetic speech that instructs the patient how to improve or maintain the alignment of the eye, for example, "Move the instrument up a little," "Look a little to the left" or "Perfect. Don't move your eyes." The loudspeaker may also be used to play instructions for using the device. One important instruction is to ask the patient to blink. A fresh tear film is important for good measurement of the optical properties of the eye.

Figure 30:
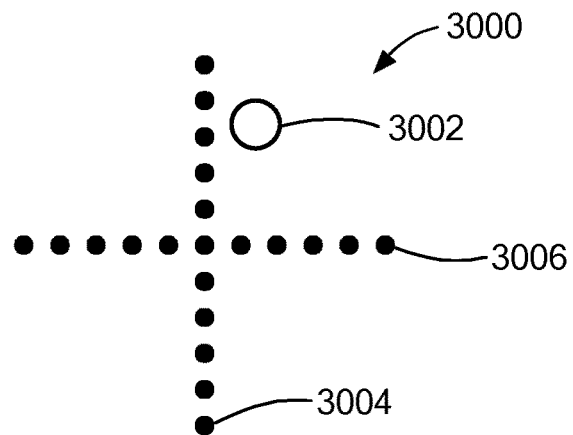
FIG. 30 is a schematic diagram of a display indicating a location of a hypothetical centroid of a spot diagram, relative to vertical and horizontal axes, according to several embodiments of the present invention.

Some embodiments include visual indicators, such as arrows illuminated by LEDs, located in the eyepiece 1102, exit port 1104 or elsewhere in the instrument 1100. Exemplary visual indicators 1548 and 1550 are shown in the eyepiece 1102 in FIG. 15. The feedback signal generator 2810 may selectively illuminate one or more of these indicators 1548 and 1550 to represent a magnitude and direction in which the patient should adjust his gaze to better align his eye with the optical axis. Optionally or alternatively, the housing 1500 (FIG. 15) includes an LCD display, and the feedback signal generator 2810 generates a display, schematically exemplified by display 3000 in FIG. 30, indicating the location of the centroid 3002 of the spot diagram, relative to vertical and horizontal axes 3004 and 3006 that intersect at the center of the optical sensor. Such a display 3000 may be used by an operator who coaches the patient. Another embodiment of the display 3000 is indicated at 2351 in FIG. 23-1. Optionally or alternatively, the housing 1500 may include lights, such as LEDs, coupled to the feedback signal generator 2810 to indicate a relative direction, and optionally a relative distance, in which the instrument 1100 should be moved to improve alignment of the eye with the optical axis.

Some embodiments include haptic output devices that signal a patient with vibration along an axis to indicate the patient should shift his gaze or move the instrument 1100 in a direction along the axis of vibration. The frequency of vibration may indicate an extent to which the patient should shift his gaze or move the instrument 1100.

Thus far, it has been assumed at least a portion of the spot diagram falls on the optical sensor. However, if the eye is grossly misaligned with the optical axis, none of the spot diagram falls on the optical sensor, or an insufficient portion of the spot diagram falls on the optical sensor for the spot diagram centroid calculator 2802 to calculate a centroid location. Some embodiments solve this problem by including an array of light sensors around the optical sensor 1532, as shown schematically in FIG. 31. Here, an array 3100 of light sensors, exemplified by light sensors 3102, 3104 and 3106, are arranged to largely surround the optical sensor 1532. The light sensors 3102-3106 are shown the same size as the optical sensor 1532. However, the light sensors 3102-3106 may be smaller or larger than the optical sensor 1532. Each light sensor 3102-3106 has a single light-sensitive area. Thus, the light sensors 3102-3104 may be less expensive than the optical sensor 1532.

The light sensors 3102-3106 are coupled to the spot diagram centroid calculator 2802. If the spot diagram, here exemplified by a spot diagram 3108, falls off the optical sensor 1532, a signal from one or more of the light sensors 3102-3106 indicates to the spot diagram centroid calculator 2802 at least a direction from the center of the optical sensor 1532 to the spot diagram 3108. As in the case where only a portion of the spot diagram falls on the optical sensor 1532, the spot diagram centroid calculator 2802 may use signals from the array of light sensors 3100 to calculate at least an approximate location of the spot diagram 3108 and provide this as a simulated location of the centroid of the spot diagram.

Optionally or alternatively, the spot diagram centroid calculator 2802 simply returns one of several directions from the center of the optical sensor 1532, in which the spot diagram 3108 has fallen. The number of possible directions may be equal to the number of light sensors 3102-3106 in the array 3100. The number of possible directions may be greater than the number of light sensors 3102-3106. For example, with three or more light sensors, the spot diagram centroid calculator 2802 may calculate a direction by taking a weighted sum of the signals from the light sensors. Optionally, the spot diagram centroid calculator 2802 may generate an additional signal to indicate the true centroid of the spot diagram is off the optical sensor 1532.

Figure 31:
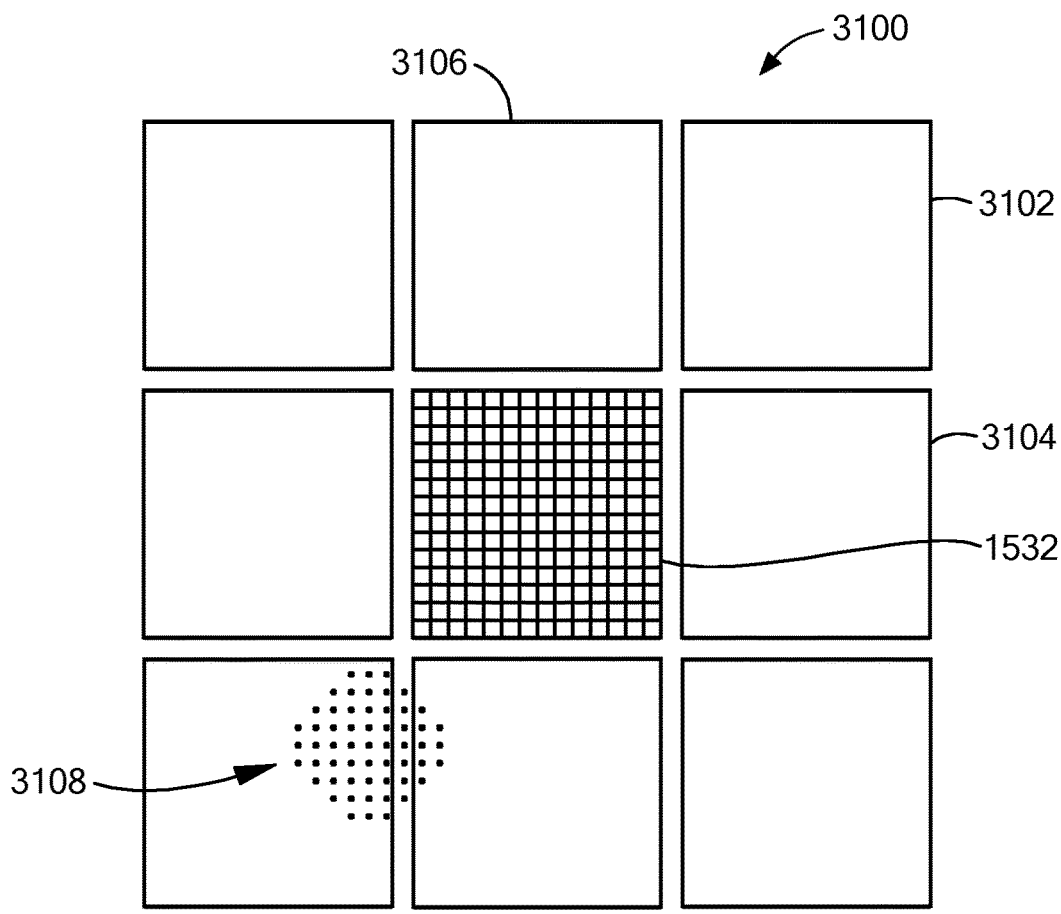
FIG. 31 is a plan view of an array of light sensors around the optical sensor of the device of FIGS. 11-15, according to several embodiments of the present invention.

In the embodiment shown in FIG. 31, eight light sensors 3102-3106 are used in one square ring around the optical sensor 1532. However, in other embodiments, other numbers of light sensors and/or other number of concentric rings and/or other shaped rings may be used. The number of light sensors and/or rings may be selected based on a desired resolution of the direction and/or distance to the spot diagram.

Figure 32:
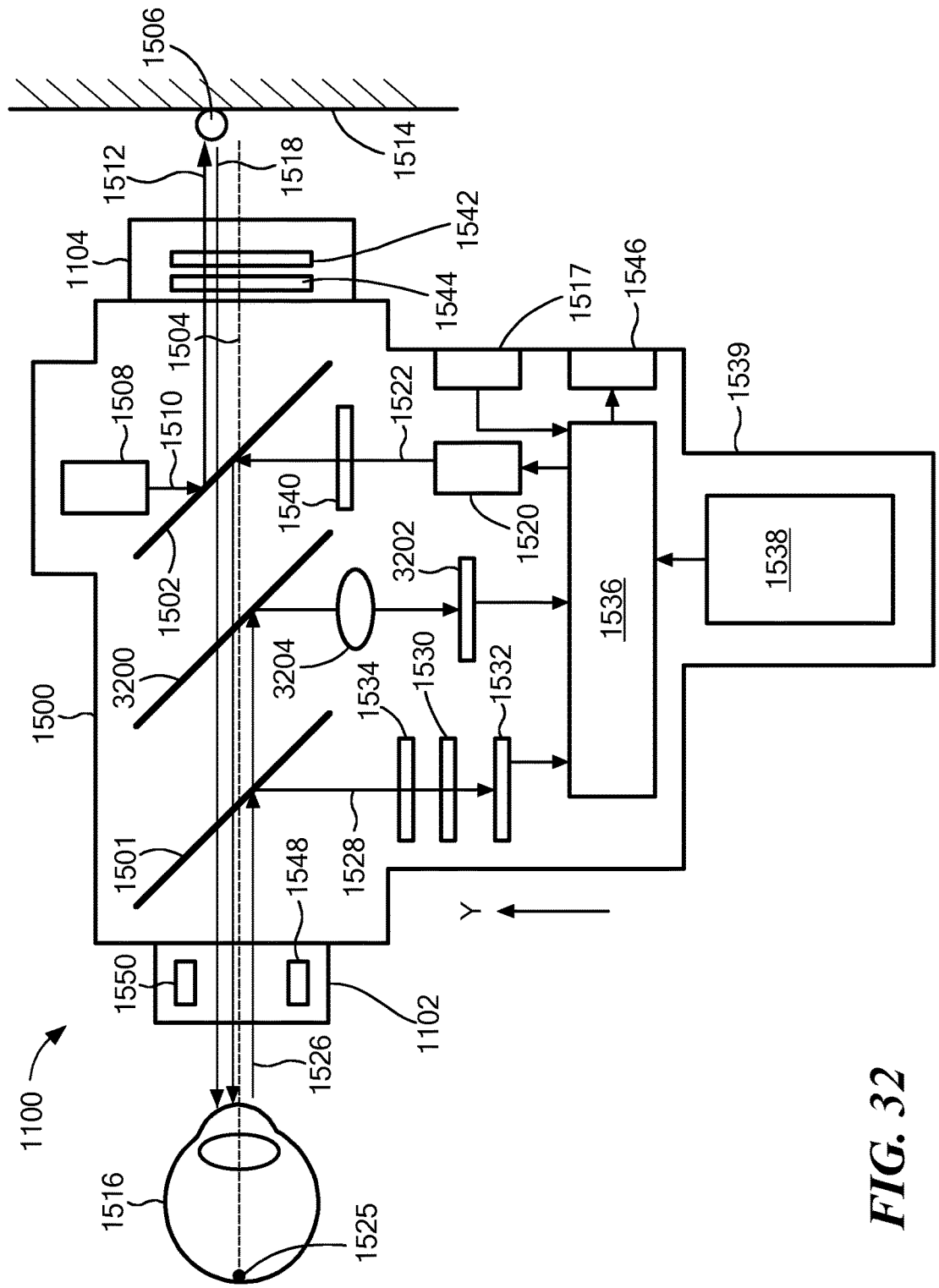
FIG. 32 is a schematic block diagram of the device of FIGS. 11-14, showing its internal components, according to another embodiment of the present invention.
Figure 33:
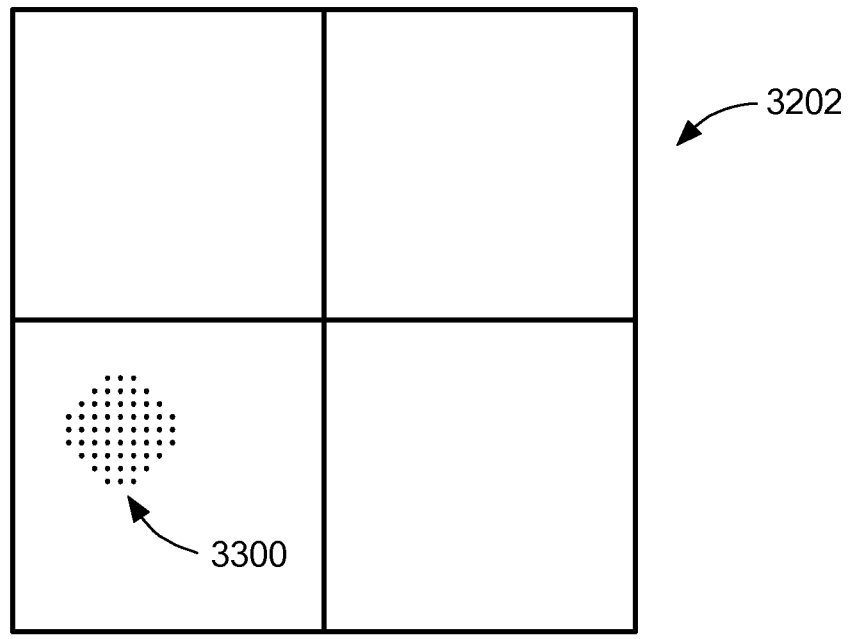
FIG. 33 is a plan view of a quadrant photodiode detector of the device of FIG. 32, including a hypothetical spot diagram projected thereon, according to an embodiment of the present invention.

In yet another embodiment shown schematically in FIG. 32, an additional beamsplitter 3200 directs a portion of the optical signal 1526 from the eye 1516 to a quadrant photodiode detector 3202. The quadrant photodiode detector 3202 is coupled to the spot diagram centroid calculator 2802. FIG. 33 is a plan view of the quadrant photodiode detector 3202, including a hypothetical spot diagram 3300 projected thereon. The quadrant photodiode detector 3202 can be any size, relative to the optical sensor 1532. However, a demagnifying lens 3204 interposed between the beamsplitter 3200 and the quadrant photodiode detector 3202 enables using a relatively small and inexpensive detector to detect locations of the spot diagrams over a relatively large area. Operation of the spot diagram centroid calculator 2802 in such embodiments is similar to the operation described above, with respect to FIG. 31. Alternatively, instead of a quadrant photodiode detector 3202, any other suitable sensor may be used, such as a position-sensitive detector (PSD) or a multi-element camera array. Alternatively, instead of a quadrant detector, a detector with another number of sectors may be used. The number of sectors may be selected based on a desired resolution with which the location of the spot diagram is to be ascertained.

Optionally or alternatively, feedback to the patient about misalignment of the patient's eye to the optical axis is provided by changing the location where the spot 1506 (FIG. 15) is projected on the wall 1514. In such embodiments, the visible light source 1508 is steerable, such as by a pan and tilt head (not shown) driven by the light source interface 2608 (FIG. 26) or by an array of visible light sources driven by the light source interface 2608. If the patient's eye is not properly aligned with the optical axis 1504 of the instrument 1100, the location of the spot 1506 is changed in a direction and by a distance that correspond to the direction and magnitude of the misalignment. Note that consequently the spot 1506 may no longer be along the optical axis 1504. As a result, the patient is subtly directed to redirect her gaze toward the new location of the spot 1506, thereby improving alignment of her eye with the optical axis 1504. The optical axis 1504 of the instrument 1100 is not changed. Only the location where the spot 1506 is projected changes.

Figure 34:
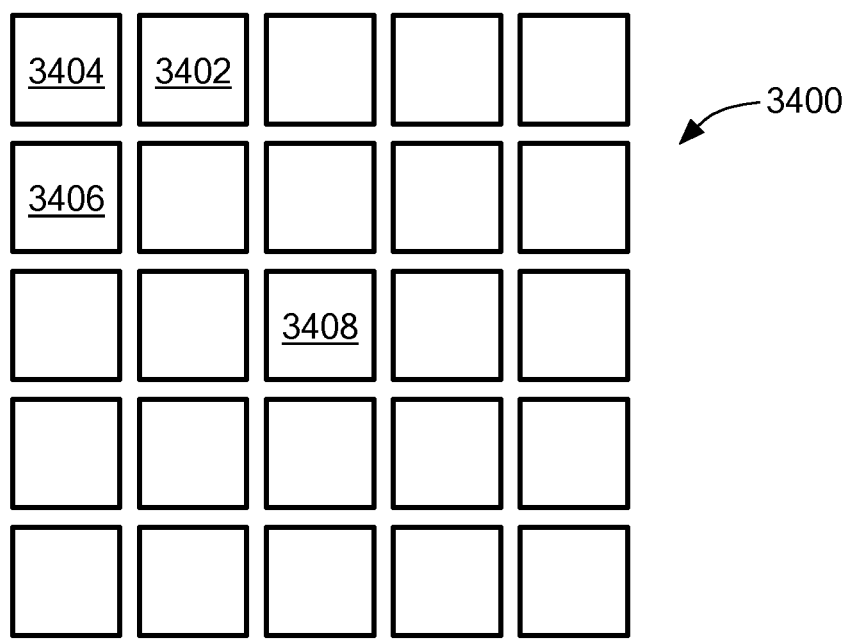
FIG. 34 is a schematic plan view of an exemplary array of visible light sources for projecting a visible spot on a distant object, according to an embodiment of the present invention.

FIG. 34 is a schematic plan view of an exemplary array 3400 of visible light sources exemplified by visible light sources 3402, 3404 and 3406. Each of the visible light sources 3402-3406 is disposed so as to project the beam of light 1510 (FIG. 15) along a slightly different axis, thereby illuminating the spot 1506 on a slightly different location on the wall 1514. The embodiment shown in FIG. 34 includes 25 visible light sources 3402-3406. However, other numbers of visible light sources and their spacings may be used, depending on a desired granularity and range of control over location of the spot 1506 on the wall 1514.

As shown in FIG. 28, the feedback signal generator 2810 sends a signal to the light source interface 2608 to control which of the individual visible light sources 3402-3406 projects the spot 1506. A central visible light source 3408 is disposed where a single visible light source 1508 would otherwise be disposed, so as to project the spot 1506 along the optical axis 1504. This light source 3408 is used to initially illuminate the spot 1506 on the wall 1514. However, if the spot diagram centroid location calculator 2802 ascertains that the patient's eye is not aligned with the optical axis 1504, the magnitude and direction of misalignment signal 2808 causes the feedback signal generator 2810 to extinguish the visible light source 3408 and illuminate a different light source of the array of visible light sources 3400. The feedback signal generator 2810 selects one of the visible light sources 3402-3406 located a direction and distance from the central visible light source 3408 corresponding to the direction and magnitude signal 2808.

Automatically Adjust Location of Virtual Light Source to Better Center Spot Diagram on Optical Sensor Optionally or alternatively, if the patient's eye is not properly aligned with the optical axis 1504 of the instrument 1100, the location of the virtual light source 1525 (FIG. 15) within the patient's eye is changed so as to automatically generate a spot diagram that is better centered on the optical sensor 1532. In such embodiments, the light source 1520 is steerable, such as by a pan and tilt head (not shown) driven by the light source interface 2608 (FIG. 26) or by an array of light sources driven by the light source interface 2608. If the patient's eye is not properly aligned with the optical axis 1504 of the instrument 1100, the location of the virtual light source 1525 is changed in a direction and by a distance that correspond to the direction and magnitude of the misalignment. Note that consequently the virtual light source 1525 may no longer be along the optical axis 1504. As a result, the spot diagram falls on a different location on the optical sensor 1532, closer to the center of the optical sensor 1532, without any action by the patient. The optical axis 1504 of the instrument 1100 is not changed. Only the location where the spot diagram falls on the optical sensor 1532 changes.

Figure 35:
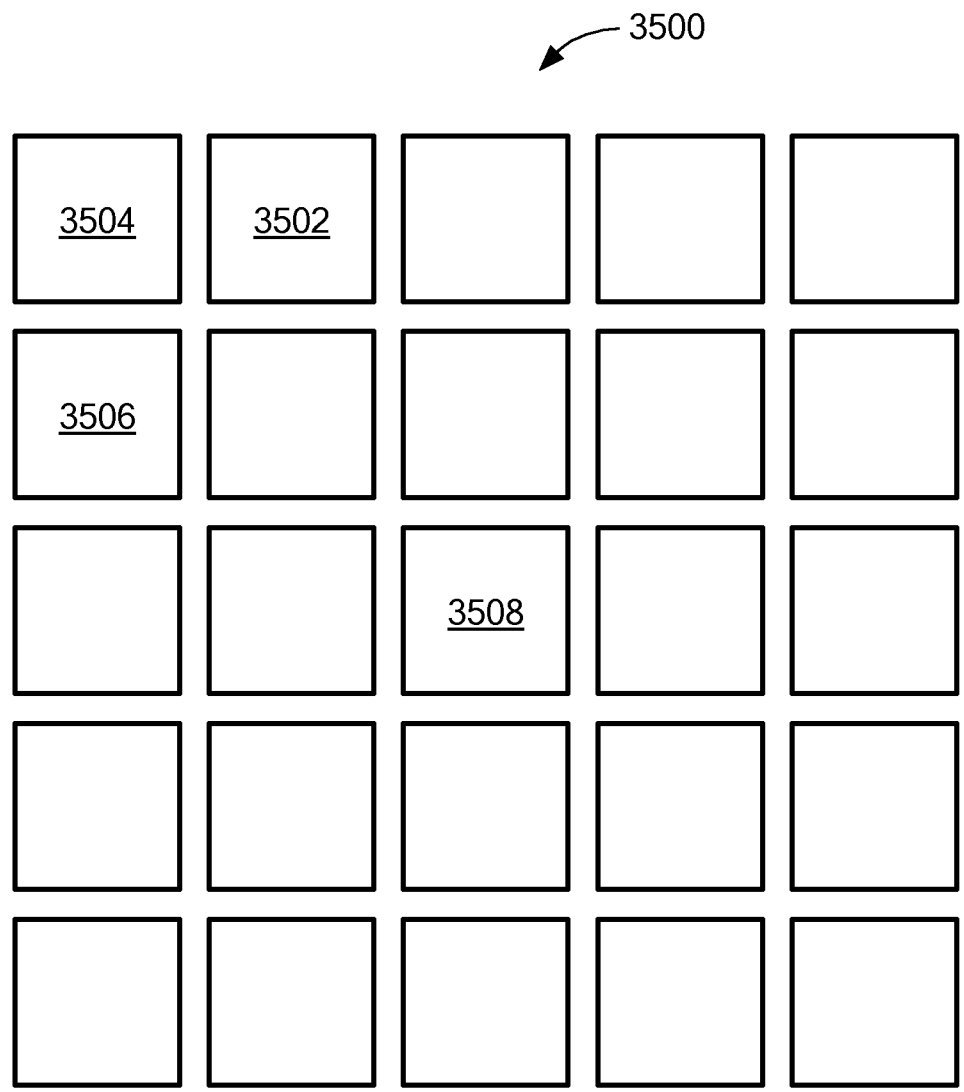
FIG. 35 is a schematic plan view of an exemplary array of light sources for projecting a virtual light source onto a retina of a patient's eye, according to an embodiment of the present invention.

FIG. 35 is a schematic plan view of an exemplary array 3500 of light sources exemplified by light sources 3502, 3504 and 3506. Each of the light sources 3502-3506 is disposed so as to project the beam of light 1522 (FIG. 15) along a slightly different axis, thereby creating the virtual light source 1525 at a slightly different location on the retina of the eye 1516. The embodiment shown in FIG. 35 includes 25 light sources 3502-3506. However, other numbers of light sources and their spacings may be used, depending on a desired granularity and range of control over location of the virtual light source 1525 on the retina of the eye 1516.

As shown in FIG. 28, the feedback signal generator 2810 sends a signal to the light source interface 2608 to control which of the individual visible light sources 3502-3506 projects the virtual light source 1525. A central light source 3508 is disposed where a single light source 1520 would otherwise be disposed, so as to project the virtual light source 1525 along the optical axis 1504. This light source 3508 is used to initially illuminate the virtual light source 1525 on the wall retina of the eye 1516. However, if the spot diagram centroid location calculator 2802 ascertains that the patient's eye is not aligned with the optical axis 1504, the magnitude and direction of misalignment signal 2808 causes the feedback signal generator 2810 to extinguish the light source 3508 and illuminate a different light source of the array of light sources 3500. The feedback signal generator 2810 selects one of the light sources 3502-3506 located a direction and distance from the central light source 3508 corresponding to the direction and magnitude signal 2808.

Automatically Determine Whether an Eye is Accommodating and Provide Feedback to Patient The open view design described herein encourage patients not to accommodate, at least in part because the patients know a spot begin projected on a wall is far away. Nevertheless, a patient may at times accommodate while her eye is being measured. Accommodation introduces an uncontrolled variable into the prescription measurement process, because a corrective eyeglass prescription should be calculated based on wavefronts emanating from an unaccommodated eye. To avoid this problem, embodiments of the present invention automatically ascertain when a patient is not accommodating and use wavefront data from such periods to calculate a prescription.

As noted, a spot diagram generated by wavefront aberrometry can be used to calculate a corrective lens prescription. However, unlike the prior art, embodiments of the present invention capture video data, i.e., a series of time spaced-apart frames, rather than one or a small number of single arbitrarily-timed images. The video frame rate may be constant or variable. The frame rate may be adjusted in real time, from frame to frame, based on characteristics of the spot diagram imaged by the optical sensor 1532 (FIG. 15), such as overall illumination and percent of saturated pixels in a given frame. In some embodiments, the frame rate may vary from about 6 frames per second to more than 15 frames per second. Nevertheless, the inter-frame time is relative short, on the order of about $1/10$ second, thus we refer to the video frames as being "continuous." The video data is captured from the optical sensor 1532 (FIG. 15) and stored in the memory 2602 (FIG. 26) for processing. Each frame of the video includes an image captured by the optical sensor 1532, an associated frame number and, if the frame rate is not constant, an associated time at which the frame was captured. Thus, a prescription can be calculated from each frame. An aberration profile, which may be described by a refractive prescription, a set of Zernike coefficients, or some other representation calculated from a frame is referred to herein as a "candidate prescription," because some frames include noise, incomplete spot diagrams, no spot diagram or are otherwise undesirable for prescription calculation.

A candidate prescription is calculated for each frame and stored in the memory 2602. The candidate prescription calculations may be performed after the last frame of the video has been captured, or the calculations may overlap in time with the video capture and storage. If sufficient computing power is available, a candidate prescription may be calculated for each frame, after the frame has been captured, but before the successive frame is captured. In the latter case, in some embodiments, the raw video data is not stored in the memory 2602.

Figure 36:
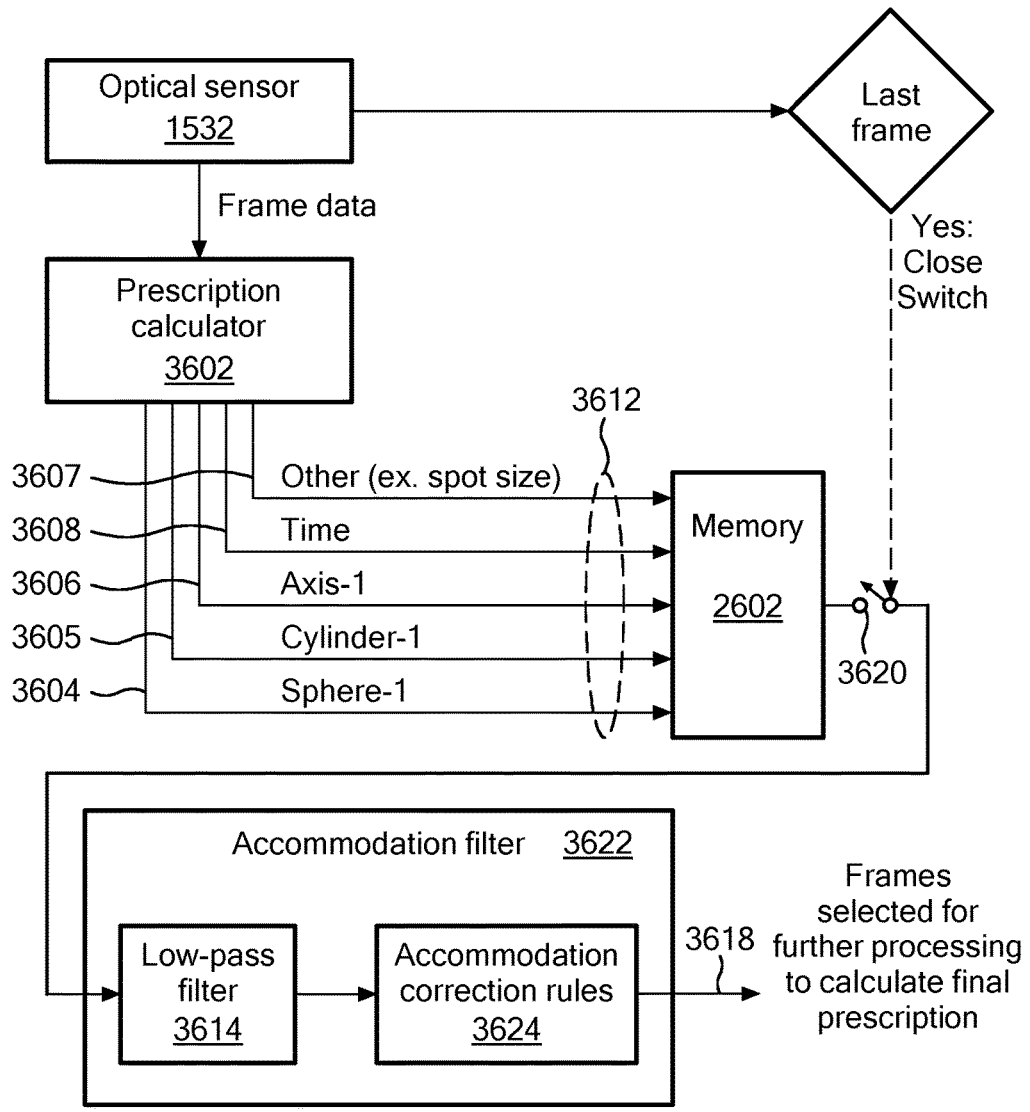
FIG. 36 is a schematic block diagram of an unaccommodation detector, according to an embodiment of the present invention.

FIG. 36 is a schematic block diagram of an unaccommodation detector module 3600, according to an embodiment of the present invention. A prescription calculator 3602 receives signals from the optical sensor 1532 and calculates a candidate prescription from the signals, as described herein. As noted, a prescription typically includes at least a spherical component and one or two cylindrical components. The spherical component is described in terms of the optical power, positive or negative, and the cylindrical component is described in terms of powers and axes or equivalent terms (e. g. power vector notation). A prescription may also include additional lens specifications to correct higher order aberrations.

The prescription calculator 3602 outputs a set of individual lens specifications, such as sphere 3604, cylinder-1 3605, axis-1 3606, etc. Optionally, other information 3607, such as spot size, is also output. The outputs are collectively referred to as a candidate prescription 3612. Each candidate prescription 3612 is stored in the memory 2602 (FIG. 26), along with an identification of from which video frame the candidate prescription was calculated or the relative time 3608 at which the frame was taken by the optical sensor 1532. The as sphere 3604, cylinder-1 3605, axis-1 3606, etc. can be prescription data calculated using various Zernike modes, such as M, J0 and J45, obtained using various order Zernike information.

A normally-open switch 3620 closes after all the frames have been acquired.

The spot diagram size is related to a quality metric, and it gives some information about the prescription. Assuming a constant pupil size, if the eye is emmetropic, the spot diagram size is equal to pupil size. However, if the eye myopic, the spot diagram is smaller than the pupil size. The higher the myopia, the smaller the pupil size. On the other hand, if the eye is hyperopic, the spot diagram diameter is bigger than the pupil size. The more hyperopic, the bigger the spot diagram.

The spot diagram size also change with accommodation. Thus, if the patient is accommodating, the instrument can detect changes in spot diagram size.

The spot diagram size is related to pupil size, and pupil size is related to amount of light received by the eye. In darker environments, the pupil automatically becomes larger. Thus, the instrument can use pupil size, as estimated from spot diagram size, to track external conditions, such as a change in ambient light in the room while the patient was being measured.

In addition, the size of the spot diagram can be related to a quality metric. Using the defocus aberration and propagation algorithms, spot diagram size can be used to calculate the pupil size. The pupil size is important to measure the aberrations, because the aberration profile is associated with a specific aperture diameter.

Figure 37:
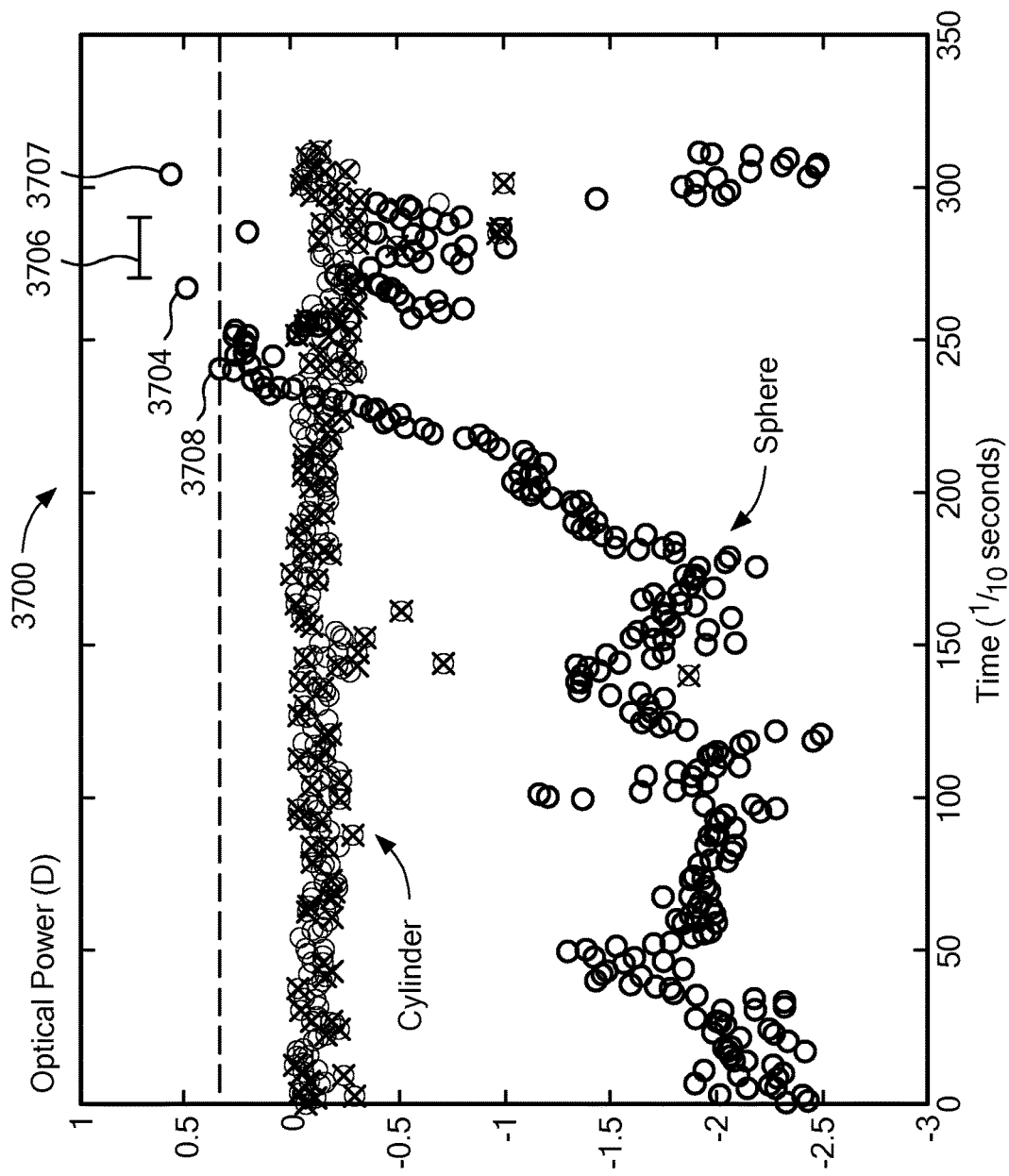
FIG. 37 contains a graph of spherical and cylindrical power candidate prescriptions calculated from a hypothetical patient, according to an embodiment of the present invention.

FIG. 37 contains a graph 3700 of spherical and cylindrical power candidate prescriptions calculated from a hypothetical patient. Open circles represent spherical candidate prescriptions, and crossed circles represent cylindrical candidate prescriptions. The vertical axis indicates power in diopters (D), and the horizontal axis indicates time at which the candidate prescriptions were calculated. The frames were captured at approximately 10 frames per second.

FIG. 37 shows the patient's candidate spherical prescription varying over time, starting at about −2.25 D at time 1. Starting at about time 175, the candidate spherical prescription increases from about −1.7 D to about +0.4 D at about time 240. After about time 240, the candidate spherical prescription decreases.

When an eye is unaccommodated, the candidate spherical prescription should be different than any candidate spherical prescription calculated while the eye is accommodated, because an unaccommodated crystalline lens provides different optical power than an accommodated crystalline lens and, therefore, requires a different correction than an accommodated lens. On the other hand, cylindrical correction does not vary significantly with amount of accommodation, so if variations in the cylindrical components of the prescriptions are found, these are in general indicatives of undesirable movements of the patient during the test. Thus, from the graph in FIG. 37, it would appear as though candidate spherical prescription around 0 D (such as 3702) should be closer to the correct prescription for the patient, because those are the greatest candidate spherical prescriptions calculated.

However, embodiments of the present invention do not necessarily accept the greatest candidate spherical prescription as the correct prescription, because a candidate prescription may be a result of noise and the magnitude and direction of the accommodation may depend on or other factors such as the actual refractive error of the patient. For example, in the case illustrated by FIG. 37, neither candidate spherical prescription 3702 nor 3704 is accepted, because we realize an eye cannot change accommodation quickly enough to have yielded either candidate spherical prescription 3702 or 3704. The literature reports a maximum accommodation rate of about 1-2 diopters per second in a human eye. A bar 3706 indicates an approximate amount of time required by an eye to change accommodation from a close to a distant object. In contrast, candidate spherical prescriptions 3702 and 3704 would have required the eye to change accommodations much more quickly than is physiologically common. Furthermore, an eye changes accommodation continuously, as the crystalline lens changes shape. Thus, candidate prescriptions with no nearby candidate prescriptions are very likely a result of noise. For instance, in the case of a myopic eye with a small pupil, there will be very few spots composing the spot diagram. The errors in determining the centroids of these spots from specular noise can then cause large errors in the calculation of the Zernike coefficients corresponding to the defocus of the eye.

Returning to FIG. 36, after all the frames have been acquired, the normally-open switch 3620 is closed, and the candidate spherical prescription 3604 is fed to a low-pass filter 3614 in an accommodation filter 3622 (accommodation filter 3810 in FIG. 38) to remove candidate spherical prescriptions that are radically different than surrounding candidate spherical prescriptions, i.e., where the absolute slope of the candidate spherical prescription is greater than a predetermined value. In some embodiments, an instantaneous slope in the candidate spherical prescription signal 3604 greater than about +1 diopter per second triggers rejection of a candidate spherical prescription. Smoothed candidate spherical prescriptions, i.e., candidate spherical prescriptions that pass through the low-pass filter 3614, are processed according to accommodation correction rules 3624. In some embodiments, the rules 3624 select the greatest candidate spherical prescription. In the graph of FIG. 37, candidate spherical prescription 3708 would be selected by the rules 3624. However, in other embodiments, other selection criteria, machine learning or other mechanism may be used to process the candidate prescriptions to arrive at a prescription. In some embodiments, other portions of the candidate prescription 3612 or other information, such as spot diagram size as a function of time, may also be used.

The frame number or time associated with the candidate spherical prescription selected by the rules 3624 is used to select a candidate prescription stored in the memory 2602, i.e., the other candidate prescription parameters calculated from the same frame as the candidate spherical prescription detected by the rules 3624. The selected candidate prescription 3618 is reported as a prescription for the patient or fed to another module. Thus, embodiments of the present invention automatically ascertain when a patient is not accommodating and use wavefront data from such periods to calculate a prescription.

In some embodiments, more than one candidate spherical prescription may be deemed to have been calculated from frames captured while the patient's eye was not accommodated. For example, all candidate spherical prescriptions within a predetermined range of the candidate spherical prescription detected by the rules 3634, as described above, may be deemed to have been calculated from unaccommodated eye data. The rules 3634 store information in the memory 2602 identifying candidate prescriptions that were calculated from unaccommodated eye data.

Some embodiments provide feedback to the patient when a peak candidate spherical prescription has been detected or when no such peak has been detected within a predetermined amount of time after commencing collecting data from the optical sensor 1532. This feedback may be in the form of audio, visual, haptic or other feedback, along the lines described above, with respect to FIG. 28.

Combining Multiple Frames to Improve Signal-to-Noise Ratio

Although individual frames from the optical sensor 1532 that include a spot diagrams may be used to calculate prescriptions, in some embodiments multiple frames are combined to calculate a single prescription. Combining multiple frames can improve signal-to-noise (S/N) ratios, such as by averaging noise. Several embodiments that combine frames will now be described, along with additional details that pertain to these embodiments and to some embodiments that do not combine frames. Several processing modules will be described. The processing modules and interconnections among these modules are summarized in FIG. 38.

In module 3800, data is acquired from the image sensor 1532 (FIG. 15). Each frame is acquired according to image sensor settings, including exposure time and frame rate. These settings may be adjusted on a frame-by-frame basis, with a goal of acquiring frames with good signal-to-noise ratios. In general, frames with bright spots in their spot diagrams have better signal-to-noise than frames with dim spots, although a large number of spots that are saturated is undesirable. "Saturated" means a brightness value of a pixel is equal to the maximum value possible for the pixel. Alternatively, module 3800 may process frames that were acquired earlier and are stored in memory 2602.

In one embodiment, if more than a first predetermined fraction of pixels of a frame are saturated, the exposure time of the next frame is reduced. The fraction may be expressed as a percentage, for instance 0.1% of all the pixels in the sensor should be saturated. This fraction can vary based on the size of the pupil and the average size of the spots comprising the spot diagram. In addition, this fraction may be set based on characteristics of the image sensor 1532 and the light source 1520. Conversely, if fewer than a second predetermined fraction of the pixels of the frame are saturated, the exposure time of the next frame is increased. However, the exposure time should not be increased to a value that might cause motion blur as a result of the eye moving. Thus, a maximum exposure time can be ascertained, based on the size of the optical sensor 1532 and the number of pixels or quadrants it contains. Outputs from the data acquisition module 3800 are summarized in Table 1.

TABLE 1

Outputs from data acquisition module

A set of frames
A timestamp for each of the frames
Image sensor settings (exposure time and frame rate) for each frame
Fraction of pixels that are saturated in each frame
How well aligned the spot diagram is on the image sensor 1532, such as based on information from the array of light sensors 3100 (optional)

As noted, the patient may be instructed to adjust the position of the instrument 1100, relative to the patient's eye, so the patient perceives a red dot at maximum brightness. At this position, the instrument 1100 (FIG. 15) is well oriented, relative to the patient's eye socket. However, the patient's eye can still move within the eye socket. That is, the patient can look up, down, left and right. Thus, the center of the eye's field of view may not be aligned with the optical axis 1504 of the instrument 1100, and the spot diagram may not be centered on the optical sensor 1532, or the spot diagram may be completely off the optical sensor 1532. In addition, the patient might blink. Furthermore, in some frames, the signal reaching the optical sensor 1532 may be from a reflection from the eye's cornea, rather than from the virtual light source on the eye's retina. Thus, some frame may not contain useful information.

A frame selector 3802 retains only frames that may contain useful information. An objective of the frame selector 3802 is to ensure raw data used to calculate a prescription is as good as possible. The frame selector 3802 may discard frames, as summarized in Table 2. For example, successive frames in which the diameter of the spot diagram varies from frame to frame by more than a predetermined amount may be discarded.

The frame selector 3802 tags the frames, such as "valid," "incomplete" or possibly "discarded." The tags may be represented by codes stored in the memory 2602 in association with data representing brightness values of the pixels of the frames or prescriptions calculated from the frames.

TABLE 2

Frames discarded by frame selector module

Patient blinked (no spot diagram)
Eye grossly misaligned with optical axis (no spot diagram)
Corneal reflection (too many spots in spot diagram and of high intensity)
Rapidly changing spot diagram diameter
Too much time has passed since the last patient blink; tear film may be compromised, so the frame should be discarded (optional)
Partial spot diagram (optional)

Figure 39:
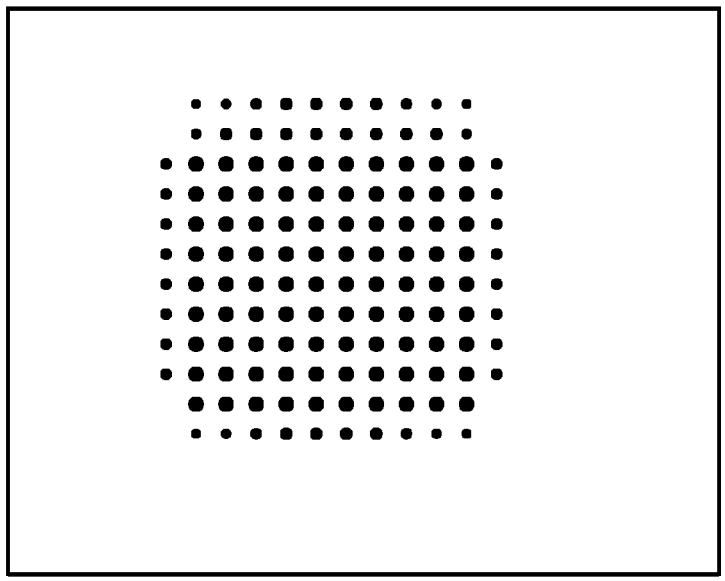
FIG. 39 is schematic diagram of a complete spot diagram captured by a prototype instrument as described herein and according to an embodiment of the present invention.
Figure 40:
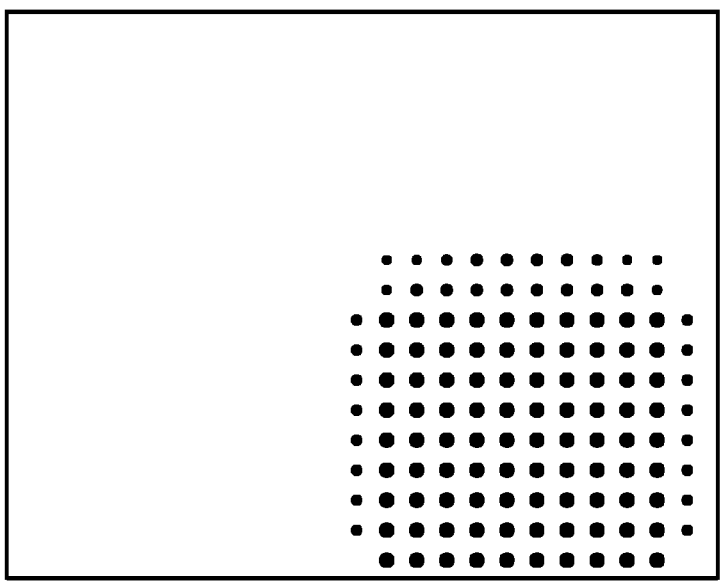
FIG. 40 is a schematic diagram of a partial spot diagram, i.e., a spot diagram in which a portion of the spot diagram falls off the optical sensor, captured by a prototype instrument as described herein and according to an embodiment of the present invention.

FIG. 39 is schematic diagram of a complete spot diagram, and FIG. 40 is a schematic diagram of a partial spot diagram, i.e., a spot diagram in which a portion of the spot diagram falls off the optical sensor 1532. The spot diagrams were captured by a prototype instrument as described herein. The frame selector 3802 may distinguish these two types of frames from each other by various techniques. For example, the frame selector 3802 may ascertain a shape of the spot diagram. If the spot diagram is approximately circular or elliptical and complete, the frame may deemed to contain a complete spot diagram, and the frame may be accepted and tagged as "valid." The frame selector 3802 may also calculate the location of the center of the spot diagram. On the other hand, if only a portion of the shape is circular, and spots of the spot diagram are adjacent edges of the optical sensor 1532, the frame may be deemed to contain a partial spot diagram and tagged "incomplete." For frames tagged as incomplete, the frame selector 3802 may also calculate or estimate what fraction of the spot diagram falls on the optical sensor 1532. As will be discussed below, incomplete spot diagrams may be used in some prescription calculations.

Figure 41:
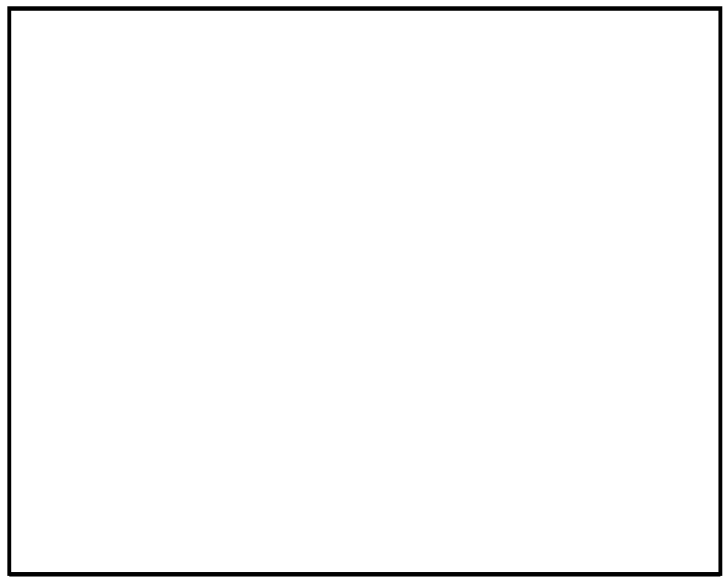
FIG. 41 is a schematic diagram of a frame from the optical sensor of FIG. 15, with no spot diagram.

FIG. 41 is a schematic diagram of a frame from the optical sensor 1532 with no spot diagram, such as a result of a patient blink or gross misalignment of the patient's eye with the optical axis 1504 of the instrument 1100. The frame selector 3802 may detect this type of frame by summing or integrating all the pixels of the frame. If the sum or integral is less than a predetermined value, indicating few or no spots of a spot diagram are present in the frame, the frame selector 3802 may discard the frame.

Figure 42:
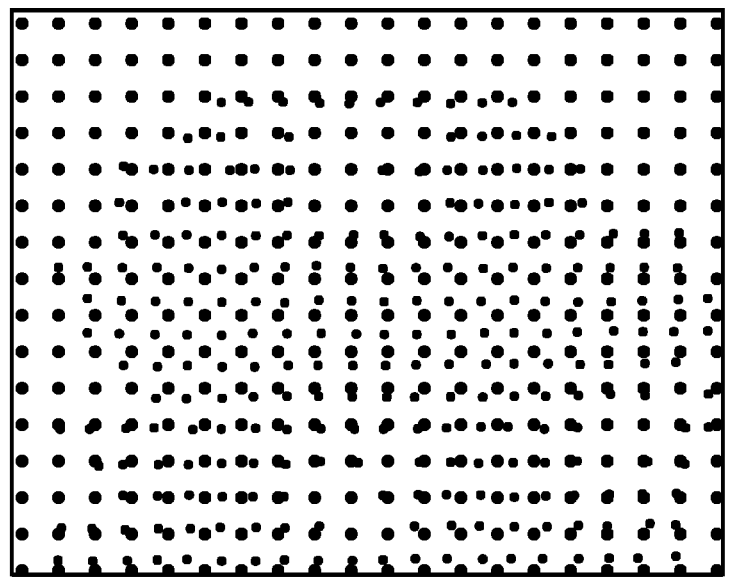
FIG. 42 is a schematic diagram of a frame from the optical sensor 1532 containing a corneal reflection, captured by a prototype instrument as described herein and according to an embodiment of the present invention.

FIG. 42 is a schematic diagram of a frame from the optical sensor 1532 containing a corneal reflection. The frame was captured by a prototype instrument as described herein. The frame selector 3802 may identify such a frame, based on several factors. For example, if the image contains more spots than lenses in the lenslet array 1530, the frame selector 3802 may discard the frame. The frame selector 3802 may sum or integrate all the pixels of the frame. If the sum or integral is greater than a predetermined value, indicating too many spots for a spot diagram are present in the frame, the frame selector 3802 may discard the frame. Frames discarded by the frame selector 3802 may be stored in the memory, but tagged "discarded."

Table 3 summarizes outputs from the frame selector 3802 module.

TABLE 3

Outputs from frame selector module

A set of consecutive frames, each containing a spot diagram (Note that some intermediate frames may have been discarded. Nevertheless, the remaining frames are referred to herein as being "consecutive.")
A timestamp for each frame
A tag for each frame, ex. "valid" or "incomplete"
Coordinates for each spot diagram's center
A diameter of each spot diagram (projected pupil size)
Image sensor settings (exposure time and frame rate) for each frame
A fraction of the pixels in each frame, or alternatively each spot diagram, that are saturated Optionally, several consecutive frames may be combined to obtain a single frame with a better signal-to-noise ratio than each of the consecutive frames. If a low-cost light source 1520 (FIG. 15) is used to create the virtual light source 1525 in the patient's eye 1516, the images acquired by the optical sensor 1532 may include significant speckle noise. Speckle noise may result from path length differences between points within the virtual light source 1525 and the optical sensor 1532. These path length differences cause random variations in intensity due to mutual interference from several wavefronts emanating from the points within the virtual light source 1525. Furthermore, even if the patient's eye does not move, intraocular fluid, such as vitreous humor, may flow, causing optical interference. On the other hand, flow of the vitreous human may randomize path lengths on the time scale of the frames and, therefore, reduce speckle noise. In any case, combining several frames can improve the signal-to-noise by averaging the speckle noise.

A frame combiner 3804 receives output from the frame selector module 3802, and optionally from the prescription calculator 3806, and outputs a single combined frame. The frame combiner 3804 may combine only consecutive frames that are tagged "valid." Optionally or alternatively, the frame combiner 3804 may combine consecutive frames that are tagged "valid" or "incomplete." Optionally, the frame combiner 3804 may combine non-consecutive frames, based on the prescription information provided by the prescription calculator 3806.

In combining frames, the frame combiner 3804 registers the frames that are to be combined, so corresponding spots of the spot diagram register with each other. A non-deforming (rigid) registration process should be used, so as not to alter the shape of the spot diagram. Once the frames are registered, they may be summed or averaged. That is, the intensities recorded by corresponding pixels in each summed frame are added or averaged. In addition, the exposure time for the spot diagram should be revised by summing the exposure times of the frames that were combined. It is also to take into account at this stage that only frames which are close in time (i.e. consecutive frames in which the eye had no time to accommodate) may be combined, since accommodation can cause the combination of frames with different prescriptions leading to incorrect results.

Figure 43:
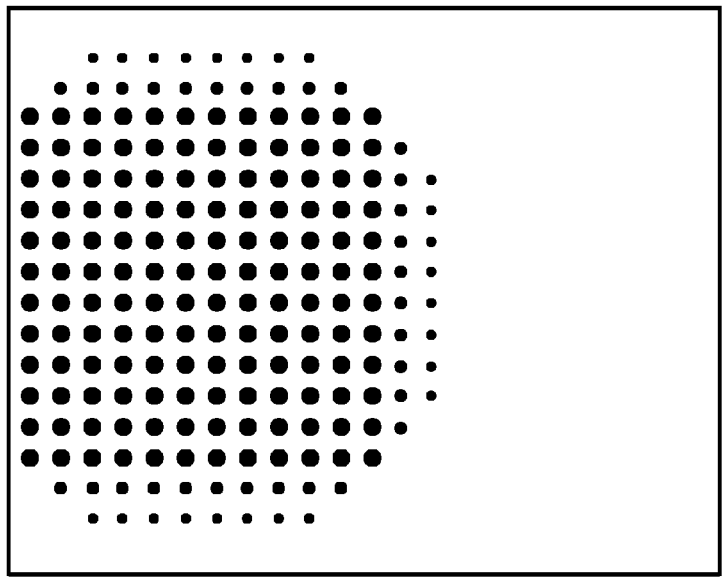
FIGS. 43-46 are schematic diagrams of a set of frames from the optical sensor of FIG. 15 containing a sequence of images acquired as an eye moves, creating a set of spot diagrams that move from left to right, captured by a prototype instrument as described herein and according to an embodiment of the present invention.
Figure 44:
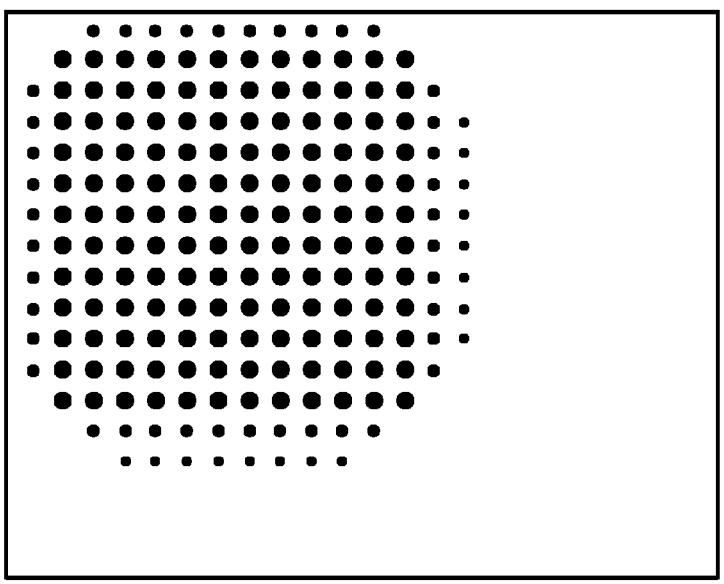
Figure 45:
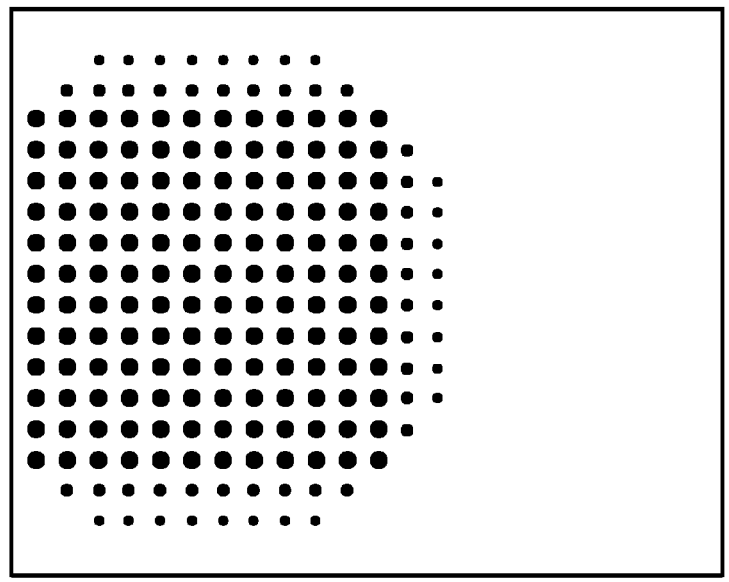
Figure 46:
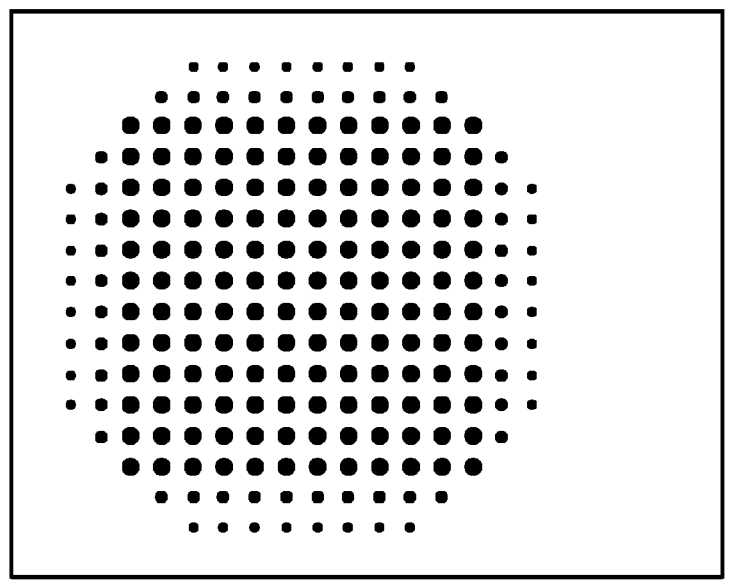

In some embodiments, only frames tagged as "valid" are combined. In some embodiments, frames tagged as "valid" and frames tagged as "incomplete" are combined. FIGS. 43-46 are schematic diagrams of a set of frames from the optical sensor 1532 containing a sequence of images acquired as an eye slowly moved, creating a set of spot diagrams that move from left to right. The frames were captured by a prototype instrument as described herein. The spot diagrams in FIGS. 43-45 are tagged incomplete, and the spot diagram in FIG. 46 is tagged valid. Essentially the same procedure as described above for combining frames may be used for combining the frames represented by FIGS. 43-46. However, some spots in the resulting combined spot diagram result from adding or averaging a different number of spots than other resulting combined spots. For example, some spots are not included in the spot diagram of FIG. 43, because these spots fall off the left side of the optical sensor 1532. These spots appear in subsequent frames, as the spot diagram moves to the right. Therefore, these spots have fewer contributions to their sum or average. Thus, these spots likely have worse signal-to-noise ratios than spots that appear in each of FIGS. 43-46.

In either case, a low-pass filter may be used to smooth each frame that is to be combined, in order to calculate registration parameters, such as displacements to apply to the frame images to register them to a target reference. The low-pass filter is used to calculate the registration parameters. Once the registration parameters have been calculated, the registration displacements are applied to the original frames, not to the filtered frames. Characteristics of the low-pass filter may be determined empirically, given characteristics of the light source 1520 (FIG. 15) and characteristics of the lenslet array 1530. Characteristics of the low-pass filter relate to size of the speckle, which is related to the diffraction limit of the lenslet array 1530. Calibrations related to misalignment of different components within the device 1100 should be applied before the registration process. Outputs from the frame combiner 3804 are summarized in Table 4.

TABLE 4

Outputs from frame combiner module

Figure 47:
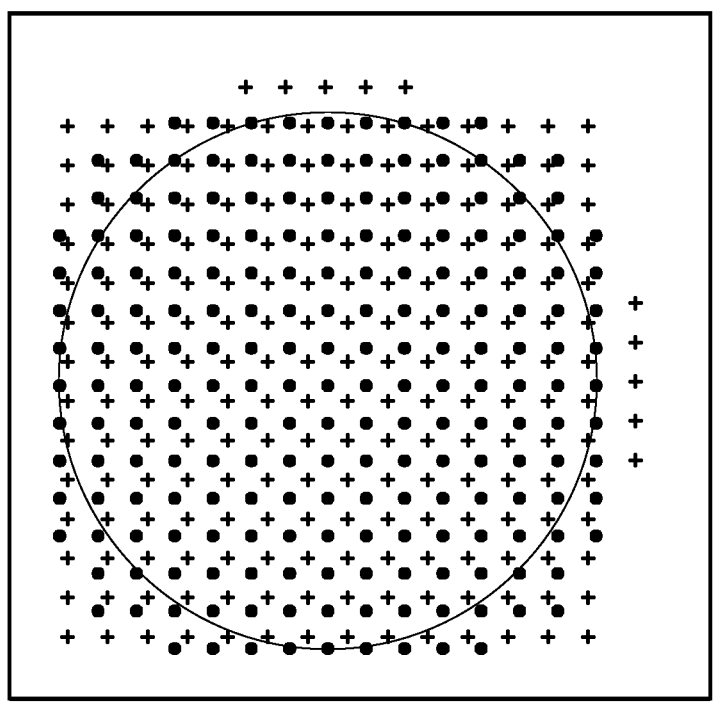
FIG. 47 is a schematic diagram of a hypothetical frame from the optical sensor of FIG. 15 containing a complete spot diagram, according to an embodiment of the present invention.

A set of consecutive frames, each containing a spot diagram
A timestamp for each frame
A tag for each frame, ex. "valid" or "incomplete"
Coordinates for each spot diagram's center
A diameter of each spot diagram (projected pupil size)
Revised image sensor settings (exposure time and frame rate) for each frame
A fraction of the pixels in each frame, or alternatively each spot diagram, that are saturated A prescription calculator module 3806 calculates a prescription from each frame. For each frame, the prescription calculator 3806 calculates centroid coordinates for each spot of the spot diagram. FIG. 47 is a schematic diagram of a hypothetical frame from the optical sensor 1532 containing a complete spot diagram. An "X" indicates the centroid of the spot diagram. Crosses indicate centroid locations for spots, where they would appear for a perfect eye. As evident from the figure, many spots of the spot diagram are displaced from these crosses.

Figure 48:
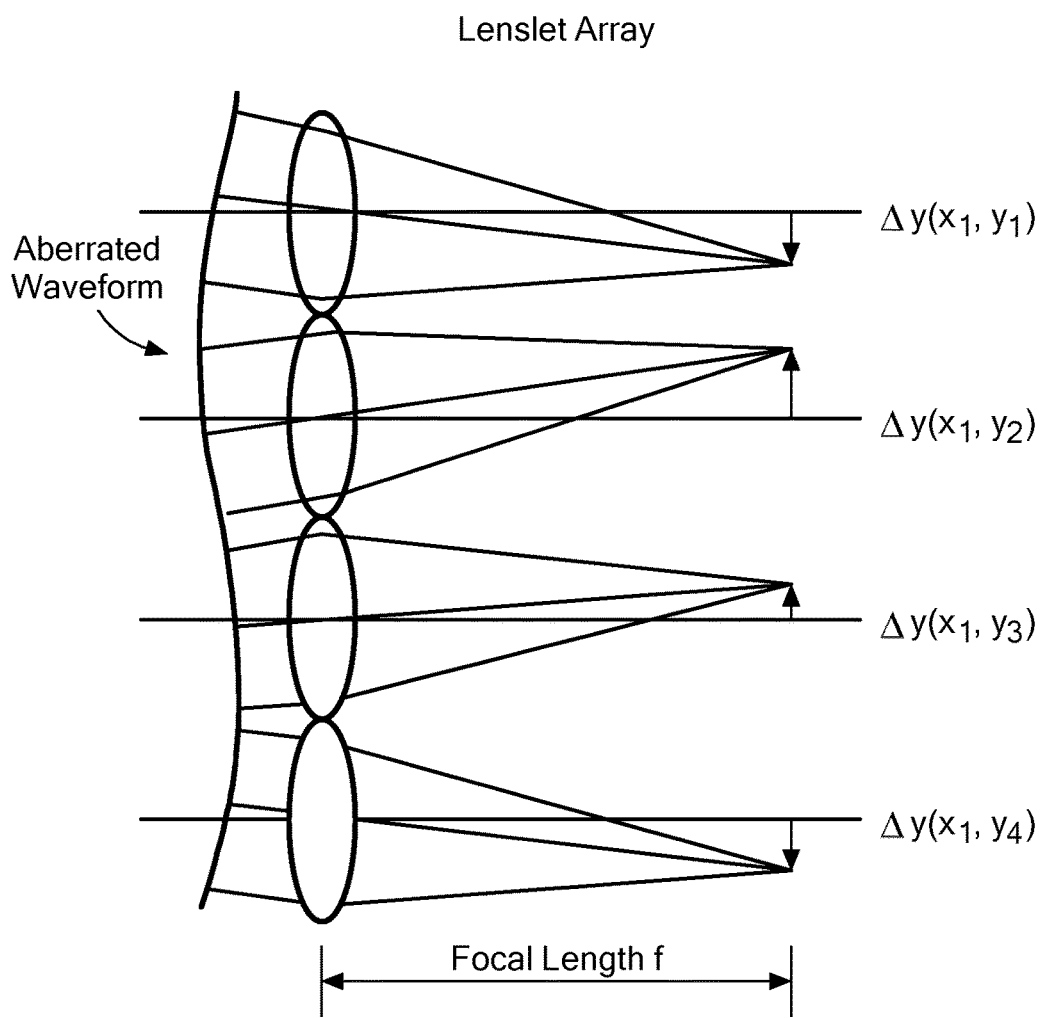
FIG. 48 is a schematic illustration of a portion of a lenslet array and a portion of a hypothetical aberrated wavefront, showing displacement calculations.

As noted, the spot diagram is generated when a wavefront impinges on an array of lenslets. A slope of the wavefront at each sample point (lens of the lenslet array) is calculated. A displacement ($\Delta x$ and $\Delta y$) of each spot of the spot diagram is calculated, relative to the location of a spot from a perfect eye, as exemplified in FIG. 48. Given the focal length of the lenslet array, the slopes can be calculated from the displacements.

The displacement data is fitted to a Zernike polynomial expansion, where the expansion coefficients are determined using least-squares estimation, as summarized in the following equations:

$$\frac{\delta W(x, y)}{\delta x} = \frac{\Delta x(x, y)}{f}$$

$$\frac{\delta W(x, y)}{\delta y} = \frac{\Delta y(x, y)}{f}$$

$$W(x, y) = \sum_k W_j Z_j(x, y)$$

$W_j$ is the coefficient of the $Z_j$ mode in the expansion.
$W_j$ is equal to the RMS wavefront error for that mode.

The Zernike coefficients are used to calculate a prescription. Because the Zernike expansion employs an orthonormal set of basis functions, the least-squares solution is given by the second order Zernike coefficients, regardless of the value of the other coefficients. These second-order Zernike coefficients can be converted to a sphero-cylindrical prescription in power vector notation using the following or other well-known equations:

$$M = \frac{-c_2^0 4\sqrt{3}}{r^2}$$

$$J_0 = \frac{-c_2^2 2\sqrt{6}}{r^2}$$

$$J_{45} = \frac{-c_2^{-2} 2\sqrt{6}}{r^2}$$

Where $C_n^m$ is the nth order Zernike coefficient, and r is pupil radius. It is also possible to compute a prescription using more Zernike coefficients, i.e., for higher order aberrations, as indicated, for example, in the following equations:

$$M = \frac{-c_2^0 4\sqrt{3} + c_4^0 12\sqrt{5} - c_6^0 24\sqrt{7} + \dots}{r^2}$$

$$J_0 = \frac{-c_2^2 2\sqrt{6} + c_4^2 6\sqrt{10} - c_6^2 12\sqrt{14} + \dots}{r^2}$$

$$J_{45} = \frac{-c_2^{-2} 2\sqrt{6} + c_4^{-2} 6\sqrt{10} - c_6^{-2} 12\sqrt{14} + \dots}{r^2}$$

The power vector notation is a cross-cylinder convention that is easily transposed into conventional formats used by clinicians.

While or after the Zernike coefficients are used to calculate a prescription, calibrations can be applied to the Zernike coefficients or to the power vectors to eliminate errors of the device 1100, such as gain, offset, non-linearity or misalignments among the optical components of the system. In the equations shown above, M relates to spherical error (Myopia or hyperopia), and J0 and J45 represent astigmatism. As noted, the pupil radius is estimated, based on the size of the spot diagram. Outputs from the prescription calculator 3806 are summarized in Table 5.

TABLE 5

Outputs from prescription calculator module

A set of consecutive frames, each containing a spot diagram
A timestamp for each frame
A tag for each frame, ex. "valid" or "incomplete"
Coordinates for each spot diagram's center
A diameter of each spot diagram (projected pupil size)
Image sensor settings (exposure time and frame rate) for each frame
Zernike coefficients for each spot diagram (frame)
One or several prescriptions in the power vector domain (PWV) (M, J0 and J45), or in another domain such as optometric, for each spot diagram (frame) (The system can provide more than one prescription. For example, one prescription may be calculated with Two Zernike orders, i.e., with no high-order aberrations, and other prescriptions may be calculated using high-order aberrations, such as Zernike orders 4 or 6.)

Optionally, information about the prescription may be provided by the prescription calculator 3806 to the frame combiner 3804. In this case, the frame combiner 3804 may use this information to determine how to combine frames.

Optionally, quality metrics may be calculated for each calculated prescription by a quality metric calculator 3808. In a subsequent module, the quality metrics may be used to weight the prescription calculated from each frame or frame combination to calculate a final prescription. The quality metrics may be as simple as a binary value, for example "0" for "bad" and "1" for "good." More complex quality metrics may fall within a range, such as a real number between 0.0 and 1.0. The quality metrics may be based on, for example, the number of frames, signal-to-noise ratio of the spot diagram, number of spots in the spot diagram, sharpness of the points in the spot diagram and absence, or small values, of high-order Zernike coefficients, or combinations thereof. The signal-to-noise ratio of a frame may, for example, be calculated by dividing the mean pixel value of spots in the spot diagram by the mean pixel value of background, i.e., an area outside the spot diagram.

Outputs from the quality metric calculator 3808 are summarized in Table 6.

TABLE 6

Outputs from quality metrics module

A set of consecutive frames, each containing a spot diagram
A timestamp for each frame
A tag for each frame, ex. "valid" or "incomplete"
Coordinates for each spot diagram's center
A diameter of each spot diagram (projected pupil size)
Image sensor settings (exposure time and frame rate) for each frame
Zernike coefficients for each spot diagram (frame)
One or several prescription in the PWV (M, J0 and J45) domain for each spot diagram (frame)
Quality metrics for each frame

TABLE 7

Outputs from accommodation filter module

A set of consecutive frames, each containing a spot diagram
A timestamp for each frame
A tag for each frame, ex. "valid" or "incomplete"
Coordinates for each spot diagram's center
A diameter of each spot diagram (projected pupil size)
Image sensor settings (exposure time and frame rate) for each frame
Zernike coefficients for each spot diagram (frame)
A prescription in the PWV (M, J0 and J45) domain for each spot diagram (frame) Quality metrics for each frame
A set of not necessarily consecutive frames, each frame containing a spot diagram from which a spherical term may be calculated As noted, accommodation introduces an uncontrolled variable into the measurement process. Therefore, prescriptions calculated from spot diagrams captured while a patient is accommodating are unlikely to be accurate. Optionally, an accommodation filter module 3810 selects frames captured when the patient is not accommodating.

Figure 49:
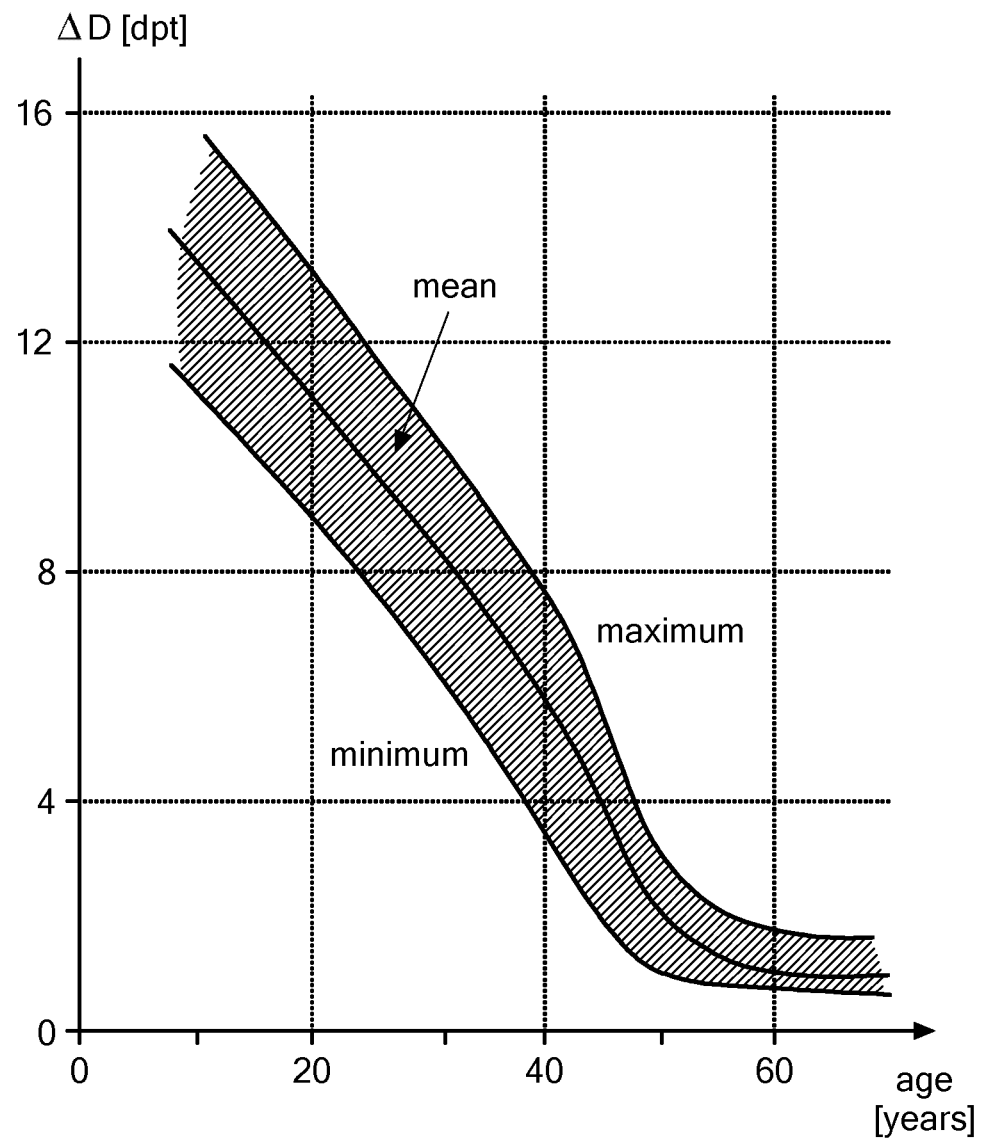
FIG. 49 is a graph showing mean, maximum and minimum amounts by which a normal human eye can accommodate, plotted against age.

The amount by which a human eye can accommodate varies with age of a patient, as summarized in a graph in FIG. 49. Embodiments of the present invention input the age of each patient, such as via a numeric keyboard or up/down arrow buttons coupled to a numeric display that increase or decrease a displayed age value as the arrow buttons are pressed. Using the age of the patient and physiological data existing in the literature about accommodation speed, the accommodation filter 3810 discards frames that evidence changes in accommodation faster than the patient should be able to accommodate, given the patient's age. In one embodiment, the accommodation filter 3810 includes a variable low-pass filter whose characteristics are controlled by the expected maximum accommodation rate. The low-pass filter operates on the M (spherical error) portion of the prescription. Other embodiments employ fixed accommodation rate limits, such as about 1 to 2 diopter per second, independent of the patient's age. In such an embodiment, a change in the calculated defocus term (or M in PWV notation) that occurs faster than the fixed accommodation rate limit is considered noise and is not included in determining the final prescription.

Figure 50:
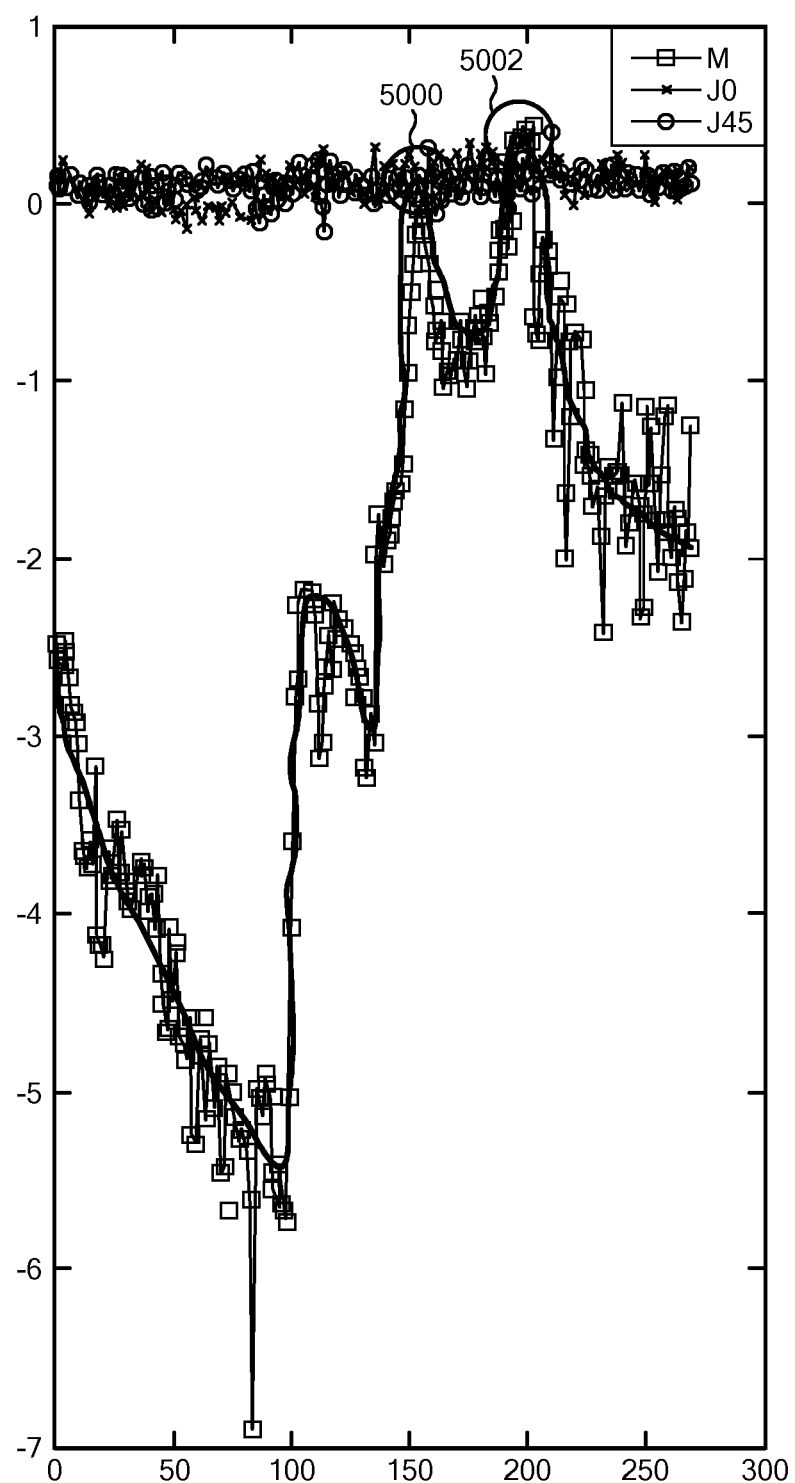
FIGS. 50 and 51 are graphs of sets of M, J0 and J45 prescriptions for two different patients, calculated by a prototype instrument as described herein and according to an embodiment of the present invention.

FIG. 50 is a graph of a set of M, J0 and J45 prescriptions calculated by a prototype instrument, as described herein. A dark line is added to show M values after processing by the accommodation filter 3810. As can be seen from variations of the M value, the patient's accommodation varied. Peaks in the M value, indicated by circles 5000 and 5002, indicate times at which the patient did not accommodate. Therefore, the accommodation filter 3810 selects frames acquired during these times and discards other frames, for the purpose of calculating spherical terms for the prescription. Because astigmatism and other terms of the prescription do not vary with accommodation, the frames discarded by the accommodation filter 3810 may be used to calculate these other terms. If variations in astigmatism as a function of time are found, this can be used as indicators of patient movements during the test, and thus used to tag frames as invalid.

Figure 51:
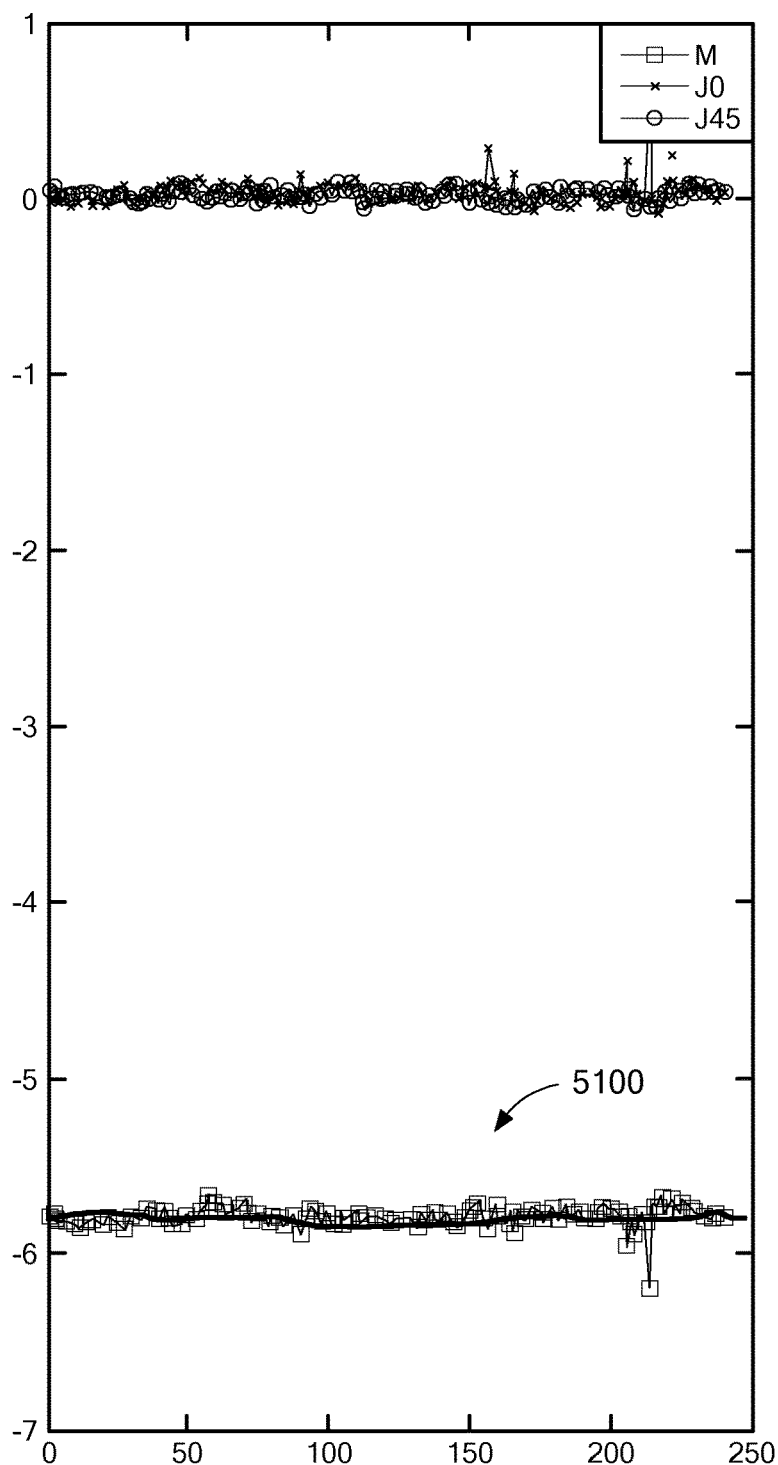

FIG. 51 is a graph of a set of M, J0 and J45 prescriptions calculated by a prototype instrument for a different patient. As can be seen, the M values 5100 do not vary significantly throughout the graph. It can, therefore, be assumed that the patient did not accommodate throughout the time period represented by the graph. In this case, the accommodation filter 3810 selects all frames represented by the graph; no frames are discarded.

Outputs of the accommodation filter are summarized in Table 7.

Figure 38:
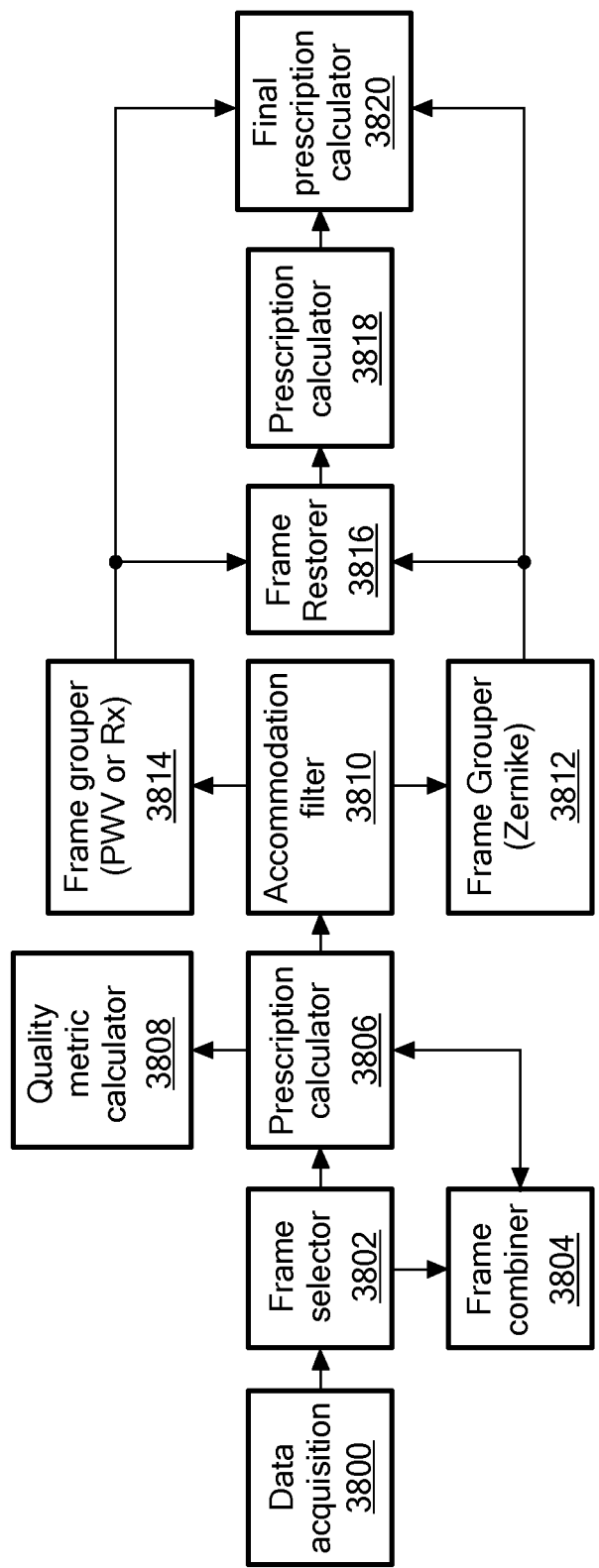
FIG. 38 is a schematic block diagram of processing modules and interconnections among these modules, according to an embodiment of the present invention.

Groups of frames may yield similar prescriptions. For example, as shown in the graph of FIG. 50, two groups of frames 5000 and 5002 yield similar J (spherical) prescriptions. Optionally, a frame grouper module identifies groups of frames that yield similar prescriptions, such as prescriptions within a predetermined range of values. Two such frame grouper modules 3812 and 3814 are shown in FIG. 38.

One frame grouper 3812 groups frames that yield similar, such as within about a 5% difference, Zernike coefficients. In some embodiments, the prescription grouper 3812 considers only the first six Zernike coefficients, although other numbers of coefficients may be used. The other frame grouper 3814 groups frames that yield similar prescriptions, for example, values of M, J0 and/or J45 that fall within about ±0.125 diopters or within about ±0.25 diopters. Frame groupers that group frames based on other similarities may also be used.

Separate groups of frames may be defined for each term of the prescription. Thus, one group of frames may be selected for having similar M values, and a different, possibly overlapping, group of frames may be selected for having similar J0 values. If some frames were discarded by the accommodation filter 3810, a different pool of frames may be available to the frame grouper 3814 for selecting frames based on similarity of M values than for selecting frames based on similarity of J0 values. Similarly, different pools of frames may be available to the other frame grouper 3812.

Figure 52:
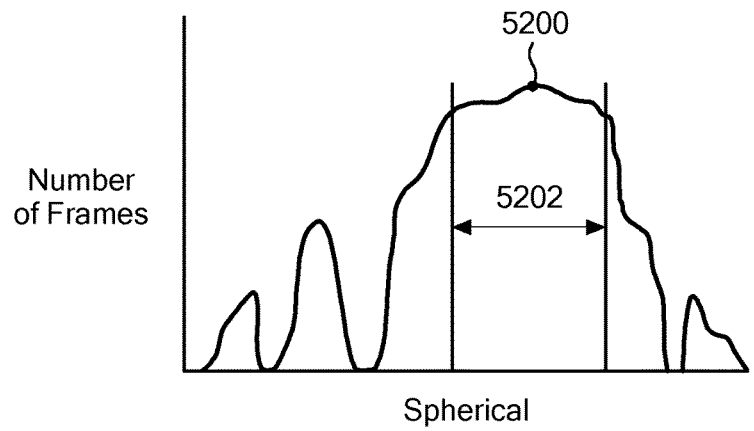
FIG. 52 is a hypothetical histogram of spherical prescriptions calculated according to an embodiment of the present invention.

The frame grouper 3814 may operate by generating a histogram for each term of the prescription. A hypothetical histogram for spherical prescriptions is shown in FIG. 52. The horizontal axis represents spherical prescription values or M values in the power vector domain, and the vertical axis represents the number of frames that yielded a given spherical prescription. Note that frames containing low-quality raw data, such as due to low signal-to-noise, were discarded by other modules. Thus, some prescription values may not have been calculated from any accepted frames. The prescription value 5200 yielded from the greatest number of frames, and a range 5202 of prescription values around this value, are selected by the frame grouper 3814. The frame grouper 3814 operates similarly for the other prescription terms. The other frame grouper 3812 operates similarly, generating a histogram for each Zernike coefficient it considers. Alternatively, instead of the histogram representing the number of frames on the vertical axis, the frame grouper 3814 may use the sum of the quality metrics for the frames. Thus, if the quality metric values are between 0.0 and 1.0, instead of the histogram indicating the number of frames that yielded a given prescription, the histogram represents the sum of the quality metrics for the frames that yielded that prescription. Optionally or alternatively, the frame groupers 3812 and 3814 may use other selection operations, other than or in addition to, histograms.

Outputs from the frame groupers 3812 and 3814 are summarized in Table 8.

TABLE 8

Outputs from each frame grouper module

A set of consecutive frames, each containing a spot diagram
A timestamp for each frame
A tag for each frame, ex. "valid" or "incomplete"
Coordinates for each spot diagram's center
A diameter of each spot diagram (projected pupil size)
Image sensor settings (exposure time and frame rate) for each frame
Zernike coefficients for each spot diagram (frame)
A prescription in the PWV (M, J0 and J45) domain for each spot diagram (frame) Quality metrics for each frame
A set of not necessarily consecutive frames, each frame containing a spot diagram from which a spherical term may be calculated
A set of frames yielding similar prescriptions or Zernike coefficients, as the case may be Optionally, frames that yield similar prescriptions or Zernike coefficients may be combined to yield frames with better signal-to-noise, and prescriptions can be calculated from the combined frames. A frame restorer 3816 combines the frames output by one or both of the frame groupers 3812 and/or 3814. The frame restorer 3816 combines these frames in a manner similar to that described above, with respect to the frame combiner 3804. All frames available from the frame grouper(s) 3812 and/or 3814 may be combined into a single frame. Alternatively, all the frames may be combined on a per prescription term basis. That is, all frames with similar M and J values may be combined to generate a single combined frame.

Figure 53:
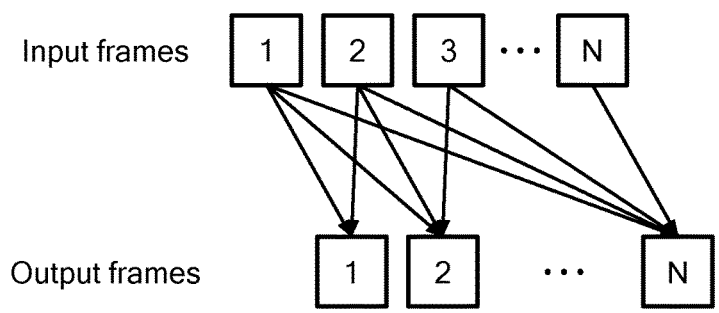
FIG. 53 is a schematic diagram illustrating combining frames to yield a second set of frames, according to an embodiment of the present invention.

Alternatively, the frames may be combined so as to yield a new set of frames in which each frame is a combination of all preceding frames in the input set of frames, as graphically illustrated in FIG. 53. Output frame 1 is generated by registering and summing or averaging input frames 1 and 2. Output frame 2 is generated by registering and summing or averaging input frames 1, 2 and 3. Output frame N is generated by registering and summing or averaging input frames 1, 2, 3, . . . N. Optionally, the quality metrics of each generated frame may be adjusted. In general, combining frames improves signal-to-noise.

Outputs of the frame restorer 3816 are summarized in Table 9.

TABLE 9

Outputs from frame restorer module

A set of consecutive frames, each containing a spot diagram
A timestamp for each frame
A tag for each frame, ex. "valid" or "incomplete"
Coordinates for each spot diagram's center
A diameter of each spot diagram (projected pupil size)
Image sensor settings (exposure time and frame rate) for each frame
Zernike coefficients for each spot diagram (frame)
A prescription in the PWV (M, J0 and J45) domain for each spot diagram (frame) Quality metrics for each frame
A set of not necessarily consecutive frames, each frame containing a spot diagram from which a spherical term may be calculated
A set of frames yielding similar prescriptions or Zernike coefficients, as the case may be A set of combined frames Optionally, a second prescription calculator 3818 calculates prescriptions from the frames generated by the frame restorer 3816. The second prescription calculator 3818 operates largely as described above, with respect to the first prescription calculator 3806, except the input dataset is different. Outputs from the second prescription calculator 3816 are essentially the same as described in Table 5.

A final prescription calculator 3820 accepts inputs from the frame grouper 3812, the frame grouper 3814 and/or the second prescription calculator 3818. The final prescription calculator 3820 calculates a single final prescription from its inputs using one or more statistical calculations. In some embodiments, the final prescription calculator 3820 calculates the final M, J0 and J45 prescriptions as a mean, mode or median of its input M, J0 and J45 prescriptions, after weighting each frame's prescriptions by the frame's quality metrics. In the final prescription calculator 3820, and in other modules described herein, higher-order prescription terms are calculated in the same manner as the M, J0 and J45 prescriptions are calculated.

Optionally, the final prescription calculator 3820 also calculates estimated error value for each final calculated prescription. In some embodiments, the M error is estimated to be the standard deviation of the final calculated M prescription, within the M input data to the final prescription calculator 3820. In some embodiments, the error is estimated to be twice the standard deviation, according to preferences of some clinicians (95% confidence interval). Other embodiments may estimate the error using other statistical formulas. This error may be communicated to the user of the device by a confidence value in the prescription, for instance, indicating a strong confidence in the measured prescription, or a weak confidence in the measured prescription and suggesting to run the test again.

Figure 54:
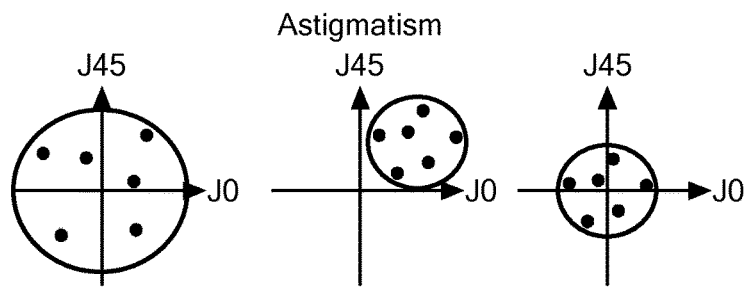
FIG. 54 is a schematic diagram illustrating calculation of an estimated confidence region for a final astigmatism prescription, according to an embodiment of the present invention.

Some embodiments estimate a confidence region for the final astigmatism prescription. This confidence region may be an ellipse computed for the bivariate distribution of J0 and J45. In these embodiments, the precision of the astigmatism prescription is deemed to be the geometric mean of the major and minor axes of the 95% confidence ellipse, as exemplified in FIG. 54.

Embodiments of the present invention are not necessarily limited to calculating prescriptions for living beings. Some embodiments may be used on a model eye ball to evaluate a person's spectacle prescription. For example, these embodiments may be used to evaluate a person's spectacles and automatically determine if they are appropriate for the person by checking the person without his spectacles and either checking the person with his spectacles on (as indicated in phantom at 1552 in FIG. 15) or checking the spectacles on a model eye. Optionally or alternatively, embodiments may be used to evaluate a person's spectacles and automatically determine if they are appropriate for the person by checking the person with his spectacles on and determining if the returned wavefronts indicate correct vision, at least within a predetermined range.

If a patient is known to be able to accommodate well, the patient's aberrations may be measured when the patient is looking through an embodiment at a target located closer than 20 feet (6 meters) away, and an accommodative offset is then calculated, so as to estimate a prescription for the patient at infinity.

In another embodiment, a monocular aberrometer includes an accelerometer in it to enable the device to ascertain which direction is up and, therefore, automatically ascertain which eye (left or right) is being measured. The device is turned upside down to measure the opposite eye.

Some embodiments also track undesired movements of a patient by tracking how astigmatism components of the prescription change, as a function of time.

While the invention is described through the above-described exemplary embodiments, modifications to, and variations of, the illustrated embodiments may be made without departing from the inventive concepts disclosed herein. For example, embodiments of the present invention may find utility in virtual reality goggles or adaptive correction displays. Furthermore, disclosed aspects, or portions thereof, may be combined in ways not listed above and/or not explicitly claimed. Accordingly, the invention should not be viewed as being limited to the disclosed embodiments.

Although aspects of embodiments may be described with reference to flowcharts and/or block diagrams, functions, operations, decisions, etc. of all or a portion of each block, or a combination of blocks, may be combined, separated into separate operations or performed in other orders. All or a portion of each block, or a combination of blocks, may be implemented as computer program instructions (such as software), hardware (such as combinatorial logic, Application Specific Integrated Circuits (ASICs), Field-Programmable Gate Arrays (FPGAs) or other hardware), firmware or combinations thereof. Embodiments may be implemented by a processor executing, or controlled by, instructions stored in a memory. The memory may be random access memory (RAM), read-only memory (ROM), flash memory or any other memory, or combination thereof, suitable for storing control software or other instructions and data. Instructions defining the functions of the present invention may be delivered to a processor in many forms, including, but not limited to, information permanently stored on tangible non-writable storage media (e.g., read-only memory devices within a computer, such as ROM, or devices readable by a computer I/O attachment, such as CD-ROM or DVD disks), information alterably stored on tangible writable storage media (e.g., floppy disks, removable flash memory and hard drives) or information conveyed to a computer through a communication medium, including wired or wireless computer networks. Moreover, while embodiments may be described in connection with various illustrative data structures, systems may be embodied using a variety of data structures.

What is claimed is:

1. A method of determining an optical property of an eye of a living human patient having two eyes and at least one hand, the method comprising:
    providing an optical apparatus having a non-stationary body, wherein:
        the body defines two proximal ports and two distal ports;
        each proximal port is configured to receive a respective eye of the two eyes of the patient; and
        the body defines two visual channels therethrough, wherein each of the two visual channels: (a) extends from a respective one of the two proximal ports to a respective one of the two distal ports and (b) is open view, thereby enabling the respective eye to see, via the visual channel, a target external to, and spaced away from, the body;
    fully supporting the body by at least one hand of the patient, such that the patient has full physical control of all degrees of freedom of movement of the body;
    aligning the two eyes of the patient with the two proximal ports;
    directing light from a light source disposed within the body, via one of the two proximal ports, into the respective eye to produce a wavefront while the respective eye focuses on the target;
    receiving, by an image sensor, the wavefront, via one of the two proximal ports;
    capturing an image of the wavefront, as the respective eye focuses on the target; and
    automatically calculating, by determining logic, a refractive error of the respective eye, based on the image of the wavefront; and
    powering the light source, the image sensor and the determining logic by a battery disposed within the body.

2. The method as defined by claim 1, further comprising automatically calculating, by the determining logic, the refractive error when refractive status of the eye is less negative than a threshold refractive value.

3. The method as defined by claim 2, automatically calculating, by the determining logic, the threshold refractive value based on a plurality of previously captured images of wavefronts.

4. The method as defined by claim 1, further comprising automatically measuring, by the determining logic, accommodation of the respective eye, as the eye views the target.

5. The method as defined by claim 4, further comprising automatically calculating, by the determining logic, the refractive error as a function of the accommodation of the respective eye.

6. The method as defined by claim 5, further comprising automatically tracking, by the determining logic, changes in the refractive status of the eye, as the eye views the target.

7. The method as defined by claim 6, further comprising automatically calculating, by the determining logic, the refractive error only when changes in refractive status of the eye during measurement are smaller than a predetermined value.

8. The method as defined by claim 1, wherein providing the optical apparatus comprises providing an optical apparatus, wherein at least one of the each proximal port comprises an eyecup.

9. The method as defined by claim 1, wherein providing the optical apparatus comprises providing an optical apparatus, wherein at each proximal port comprises a respective eyecup.

10. An ophthalmic apparatus for use by a human patient having two eyes and at least one hand, the apparatus comprising:
    a non-stationary body configured to be fully supported by the at least one hand of the patient, such that the patient has full physical control of all degrees of freedom of movement of the body, wherein:
        the body defines two proximal ports and two distal ports;
        each proximal port is configured to receive a respective eye of the two eyes of the patient; and
        the body defines two visual channels therethrough, wherein each of the two visual channels: (a) extends from a respective one of the two proximal ports to a respective one of the two distal ports and (b) is open view, thereby enabling the respective eye to see, via the visual channel, a target external to, and spaced away from, the body;
    a light source disposed within the body and configured to direct light, via one of the two proximal ports, into the respective eye and there produce a wavefront while the respective eye focuses on the target;
    an image sensor disposed within the body and configured to: (a) receive the wavefront via the one of the two proximal ports and (b) capture an image of the wavefront as the respective eye focuses on the target;

determining logic disposed within the body, coupled to the image sensor and configured to automatically calculate a refractive error of the respective eye based on the image of the wavefront; and a battery disposed within the body for powering the light source, the image sensor and the determining logic.

11. The ophthalmic apparatus of claim 10, wherein the determining logic is configured to automatically measure accommodation of the respective eye, as the eye views the target.

12. The ophthalmic apparatus of claim 11, wherein the determining logic is configured to automatically calculate the refractive error as a function of the accommodation of the respective eye.

13. The ophthalmic apparatus of claim 12, wherein the determining logic is configured to automatically track changes in the refractive status of the eye, as the eye views the target.

14. The ophthalmic apparatus of claim 13, wherein the determining logic is configured to automatically calculate the refractive error only when changes in refractive status of the eye during measurement are smaller than a predetermined value.

15. The optical apparatus as defined by claim 10, wherein the determining logic is configured to automatically calculate the refractive error using the image of the wavefront when refractive status of the eye is less negative than a threshold refractive value.

16. The optical apparatus as defined by claim 15, wherein the determining logic is configured to automatically calculate the threshold refractive value based on a plurality of previously captured images of wavefronts.

17. The optical apparatus as defined by claim 10, wherein at least one of the each proximal port comprises an eyecup.

18. The optical apparatus as defined by claim 10, wherein each proximal port comprises a respective eyecup.

* * * * *